US012122789B2

(12) United States Patent
Meier et al.

(10) Patent No.: US 12,122,789 B2
(45) Date of Patent: Oct. 22, 2024

(54) FORMS OF PYRIDO[1,2-a]PYRIMIDIN-4-ONE DERIVATIVES, ITS FORMULATION AND ITS PROCESS OF MAKING

(71) Applicant: Hoffmann-La Roche Inc., Little Falls, NJ (US)

(72) Inventors: Roland Meier, Basel (CH); Urs Schwitter, Basel (CH); Anne De Paepe, Basel (CH); Juergen Thun, Basel (CH); Frank Stowasser, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 606 days.

(21) Appl. No.: 17/233,368

(22) Filed: Apr. 16, 2021

(65) Prior Publication Data

US 2021/0403487 A1   Dec. 30, 2021

Related U.S. Application Data

(63) Continuation of application No. PCT/EP2019/078313, filed on Oct. 18, 2019.

(30) Foreign Application Priority Data

Oct. 19, 2018  (EP) .................................... 18201564

(51) Int. Cl.
*C07D 519/00*  (2006.01)

(52) U.S. Cl.
CPC ........ *C07D 519/00* (2013.01); *C07B 2200/13* (2013.01)

(58) Field of Classification Search
CPC .................................................. C07D 519/00
See application file for complete search history.

(56) References Cited

U.S. PATENT DOCUMENTS

| | | | |
|---|---|---|---|
| 9,969,754 B2 | 5/2018 | Ratni et al. | |
| 10,882,868 B2 | 1/2021 | Ranti et al. | |
| 11,827,646 B2 | 11/2023 | Ratni et al. | |
| 11,938,136 B2 | 3/2024 | Alsenz et al. | |
| 2022/0315607 A1* | 10/2022 | Matecic Musanic | C07D 519/00 |

FOREIGN PATENT DOCUMENTS

| | | |
|---|---|---|
| CN | 108289959 A | 7/2018 |
| CN | 111132981 A | 5/2020 |
| EP | 3 143 025 B1 | 10/2019 |
| JP | 2003-519698 A | 6/2003 |
| KR | 2018-0080317 A | 7/2018 |
| WO | 01/051919 A2 | 7/2001 |
| WO | 2015/173181 A1 | 11/2015 |
| WO | 2017/080967 A1 | 5/2017 |
| WO | 2019/057740 A1 | 3/2019 |
| WO | 2021/021775 A1 | 2/2021 |

OTHER PUBLICATIONS

"Assessment report: Evrysdi; International non-proprietary name: risdiplam; Procedure No. EMEA/H/C/005145/0000" EMA; Science Medicines Health: 1 (Feb. 25, 2021).
Byrn, S., et al., "Pharmaceutical Solids: A Strategic Approach to Regulatory Considerations" Pharmaceutical Res 12(7):945-954 (Jul. 1, 1995).
Enamine LLC et al., CAS Registry Database, 2344679-41-8, (Imidazo [1, 2-b] pyridazine-6-carboxylic acid, 2,8-dimethyl-C9H9N3O2), pp. 1 Creation Date Jun. 24, 2019.
Griffin, W., et al., "Classification of Surface-Active Agents by 'HLB'" J Soc Cosmet Chem 1:311-326 (1949).
International Preliminary Report on Patentability for PCT/EP2019/078313 issued Apr. 14, 2021, pp. 1-10.
International Search Report with Written Opinion for PCT/EP2019/078313 mailed Dec. 19, 2019, pp. 1-17.
Iyakushinhatsu et al., "Guideline for Standards on New pharmaceuticals and Establishment of Test Methods" The Ministry of Health, Labor and Welfare, Japan No. 568:2-46 (2001) (including English translation).
Kawaguchi, Y., et al., "Drug and Crystal Polymorphism" J Human Environ Eng—Japan 4(2):310-317 (2002) (including English translation).
"NPL3-Risdiplam reproduced XRD_WO2015173181A1 by Opponent" Mart Specialities Lab LLP:1-3 (Mar. 5, 2023).
Ooshima, H., et al., "Crystallization of Polymorphs and Pseudopolymorphs and its Control" Pharm Stage—Japan 6(10):48-53 (2007) (including English translation).
Takata, N., et al., "API Form Screening and selection in drug discovery stage" Pharm Stage-Japan 6(10):20-25 (2007) (including English translation).
U.S. Appl. No. 18/428,289, filed Jan. 31, 2024.
Yamano, M., et al., "Addressing crystal polymorphism in pharmaceutical process research" J Synthetic Org Chem—Japan 65(9):907-913 (Sep. 1, 2007) (including English translation).
"Third Party Observations filed in EP Application No. 19786617.1", 417 pages (Jun. 5, 2023).
Matecic Musanic et al., Solid State Forms of Risdiplam and Process for Preparation Thereof U.S. Appl. No. 62/880,734, filed Jul. 31, 2019, 33 pages, published Feb. 4, 2021, WIPO Patentscope URL https://patentscope.wipo.int/search/en/detail.jsf?docId=WO2021021775&_cid=P11-LBP9XD-84213-1.†

\* cited by examiner
† cited by third party

*Primary Examiner* — Niloofar Rahmani
(74) *Attorney, Agent, or Firm* — Katherine J. Mackenzie

(57) ABSTRACT

The present invention relates to a process for the preparation of 7-(4,7-diazaspiro[2.5]octan-7-yl)-2-(2,8-dimethylimidazo[1,2-b]pyridazin-6-yl)pyrido[1,2-a]pyrimidin-4-one useful as pharmaceutically active compounds.

31 Claims, 14 Drawing Sheets

FORMS OF PYRIDO[1,2-a]PYRIMIDIN-4-ONE DERIVATIVES, ITS FORMULATION AND ITS PROCESS OF MAKING

CROSS-REFERENCE TO RELATED APPLICATIONS

This application is a continuation of International Application No. PCT/EP2019/078313 having an International filing date of Oct. 18, 2019, which claims priority to European Patent Application No. 18201564.4 filed on Oct. 19, 2018, the contents of which are each incorporated by reference herein in their entirety.

FIELD OF INVENTION

The present invention relates to crystalline forms of compound of formula (I)

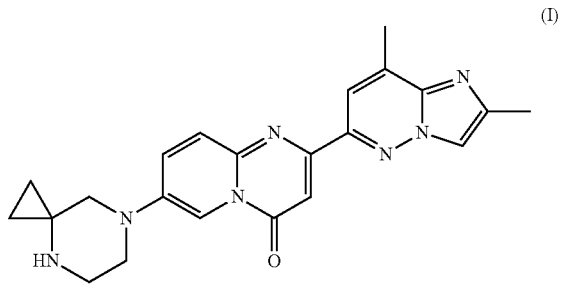 [SMILES: Cc1cn2nc(-c3cc(=O)n4cc(N5CCNC6(CC6)C5)ccc4n3)cc(C)c2n1]

(I)

7-(4,7-diazaspiro[2.5]octan-7-yl)-2-(2,8-dimethylimidazo[1,2-b]pyridazin-6-yl)pyrido[1,2-a]pyrimidin-4-one, their process of making, their composition and their use as pharmaceutically active compounds.

Figure 1:
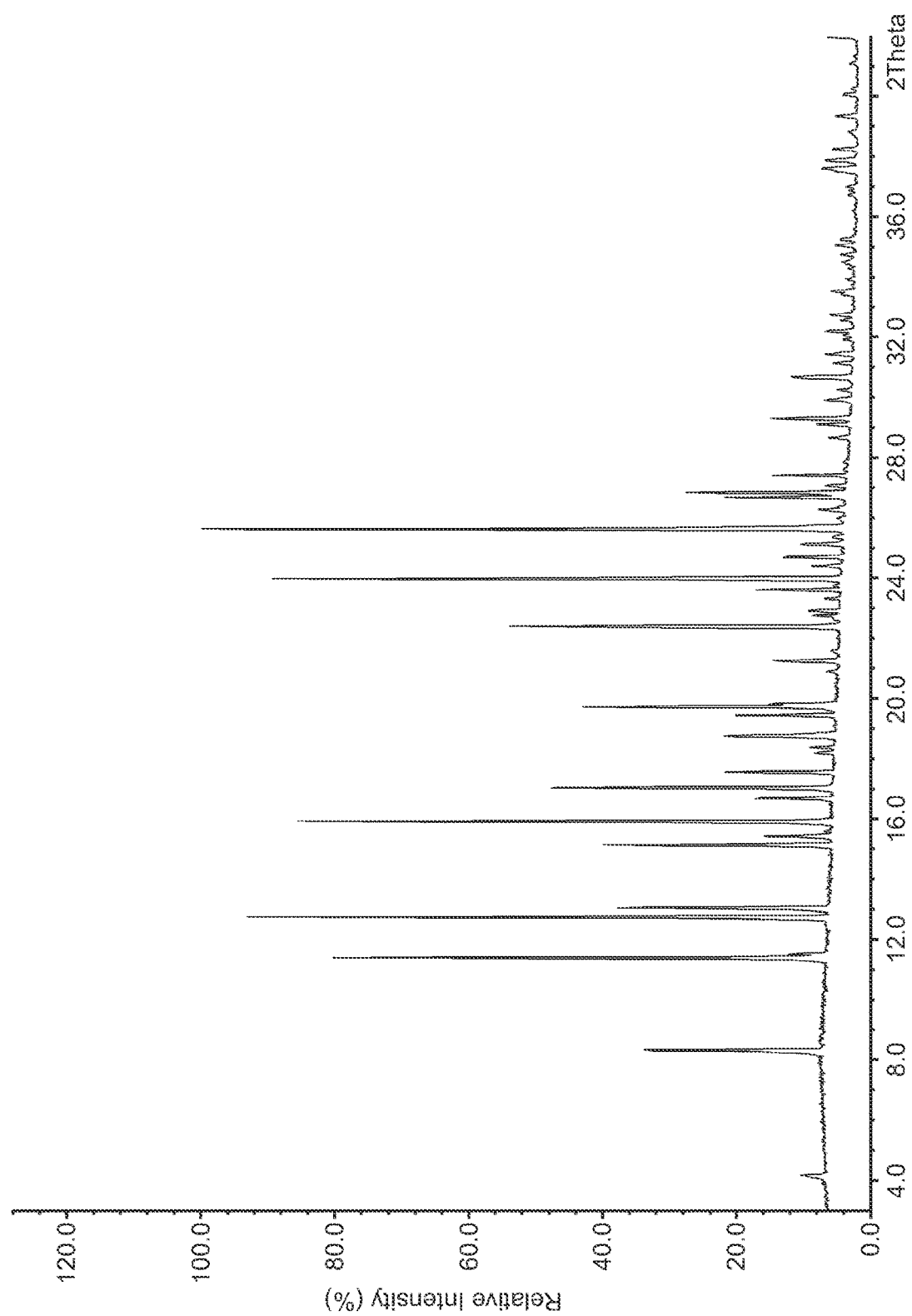
FIG. 1 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form A.

The present invention relates to the crystalline polymorphic Form A and a crystalline hydrate Form D of compound of formula (I):

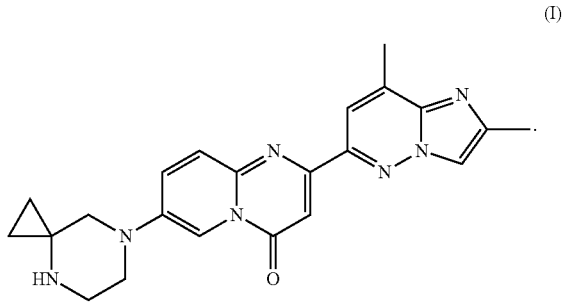 [SMILES: Cc1cn2nc(-c3cc(=O)n4cc(N5CCNC6(CC6)C5)ccc4n3)cc(C)c2n1]

(I)

Crystalline polymorphic Form A of compound of formula (I) is the thermodynamic stable polymorph.

Crystalline hydrate Form D of compound of formula (I) is the crystalline form obtained under conditions with high water activity.

In another aspect, the present invention relates also to a composition or medicament containing crystalline polymorphic Form A. Also described are uses thereof. Such new polymorphic form has properties which may be advantageous in ease of manufacturing (formulation), and dosage form stability which improves storage and/or ease of packaging.

In particular, Form A has improved chemical stability compared to Form D.

In particular, Form A has improved processability with respect to its filtration compared to Form D. This improvement allows a faster isolation of the compound of interest resulting in saving of solvents which may have a great impact on the environment.

In one embodiment, crystalline polymorphic Form A of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one, is characterized by: an X-ray powder diffraction pattern which comprises characteristic peaks at one or more of about 11.4 degrees two-theta, about 12.7 degrees two-theta, about 15.9 degrees two-theta, about 24.0 degrees two-theta, or about 25.6 degrees two-theta. In one embodiment, Form A contains two or more, three or more, four or more, or all five of these characteristic peaks. For example, Form A may contain a combination of X-ray powder diffraction pattern characteristic peaks at about 8.3 degrees two-theta, about 11.4 degrees two-theta, about 12.7 degrees two-theta, about 13.0 degrees two-theta, about 15.1 degrees two-theta, about 15.9 degrees two-theta, about 17.0 degrees two-theta, about 19.7 degrees two-theta, about 22.4 degrees two-theta, about 24.0 degrees two-theta, about 25.6 degrees two-theta and/or about 26.8 degrees two-theta. In another example, there may be three characteristic peaks at about 12.7 degrees two-theta, about 24.0 degrees two-theta, and about 25.6 degrees two-theta, which may be in further combination with a fourth peak. Optionally, all five peaks may be present. For example, crystalline polymorphic Form A of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one is characterized by: an X-ray powder diffraction pattern which comprises characteristic peaks at one or more of 11.4±0.2 degrees two-theta, 12.7±0.2 degrees two-theta, 15.9±0.2 degrees two-theta, 24.0±0.2 degrees two-theta, or 25.6±0.2 degrees two-theta. In one embodiment, Form A contains two or more, three or more, four or more, or all five of these peaks. For example, Form A may contain a combination of X-ray powder diffraction pattern characteristic peaks at 8.3±0.2 degrees two-theta and 11.4±0.2 degrees two-theta, 12.7±0.2 degrees two-theta, 13.0±0.2 degrees two-theta, 15.1±0.2 degrees two-theta 15.9±0.2 degrees two-theta, 17.0±0.2 degrees two-theta, 19.7±0.2 degrees two-theta, 22.4±0.2 and 24.0±0.2 degrees two-theta, or 25.6±0.2 degrees two-theta and 26.8±0.2 degrees two-theta. In another example, there may be three characteristic peaks at 12.7±0.2 degrees two-theta, 24.0±0.2 degrees two-theta, and 25.6±0.2 degrees two-theta, which may be in further combination with a fourth peak. Optionally, all five peaks may be present. In a further embodiment, Form A comprises a XRPD peak at an angle of diffraction at about 8.3 degrees two-theta (i 0.2) and at least an, particularly two, more particularly three, even more particularly four, even more particularly five, most particularly six, additional XRPD peak(s) at 11.4 degrees two-theta (0.2), 15.1 degrees two-theta (±0.2), 15.9 degrees two-theta (0.2), 17.0 degrees two-theta (±0.2), 24.0 degrees two-theta (0.2) or 25.6 degrees two-theta (±0.2). In another embodiment, Form A comprises XRPD peaks at an angle of diffraction at about 11.4 degrees two-theta (±02), 15.1 degrees two-theta (0.2) and 25.6 degrees two-theta (i 0.2). In another embodiment, Form A comprises XRPD peaks at an angle of diffraction at about 15.1 degrees two-theta (±0.2), 17.0 degrees two-theta (±0.2) and 25.6 degrees two-theta (0.2). In another embodiment, Fonn A comprises XRPD peaks at an angle of diffraction at about 15.1 degrees two-theta (±0.2), 24.0 degrees two-theta (±0.2) and 25.6 degrees two-theta (±0.2) In a more particular embodiment, Form A comprises XRPD peaks at an angle of diffraction at about 8.3 degrees two-theta (±0.2) and at least an, particularly two, more particularly three, even more particularly four, even more particularly five, most particularly six, additional XRPD peak(s) at 11.4 degrees two-theta (±0.2), 15.1 degrees two-theta (±0.2), 15.9 degrees two-theta (±0.2), 17.0 degrees two-theta (±0.2), 24.0 degrees two-theta (±02) or 25.6 degrees two-theta (±0.2)

A certain embodiment of the invention relates to the crystalline polymorphic Form A of the compound of formula I as described herein, characterized by the X-ray powder diffraction pattern as shown in FIG. 1.

Figure 3:
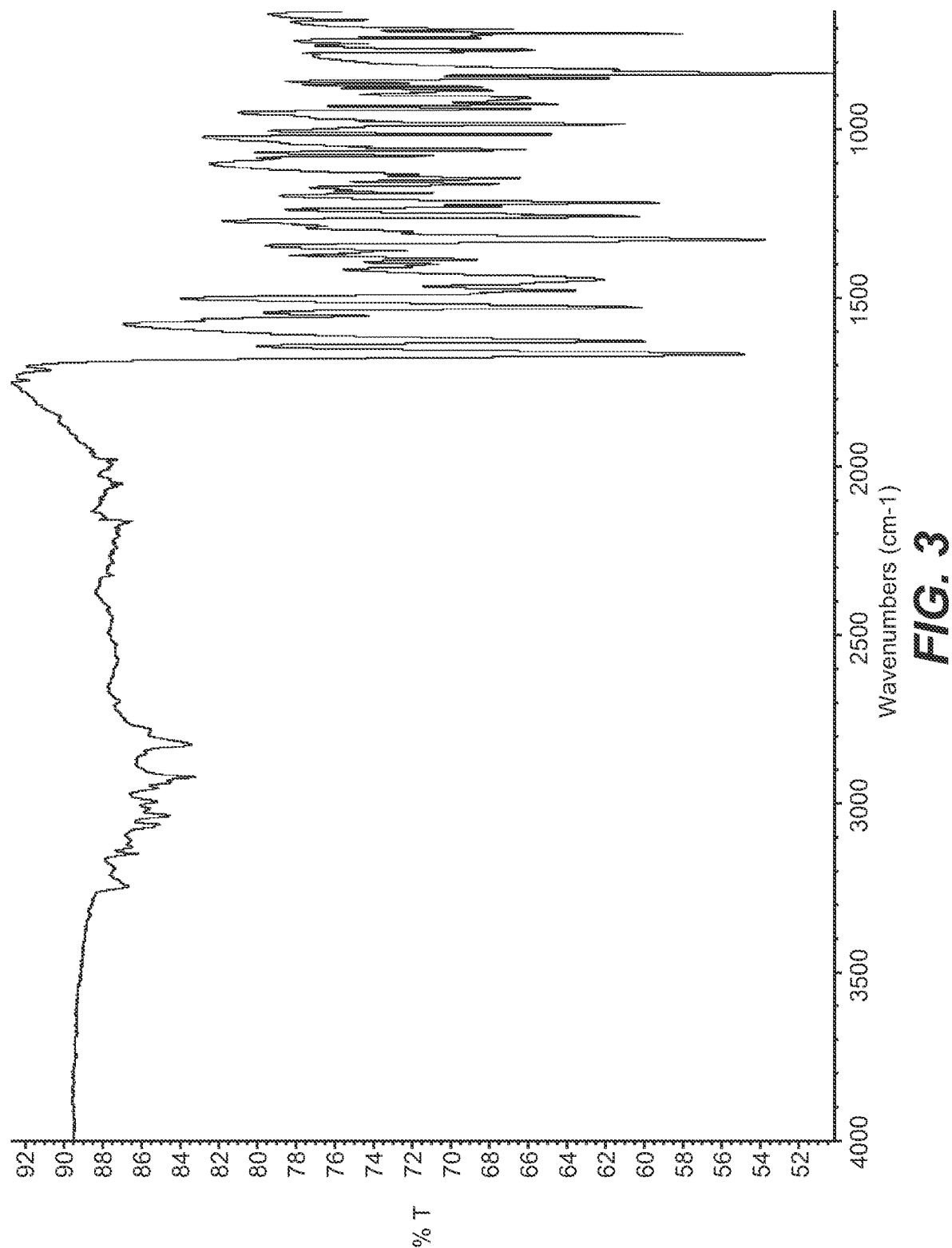
FIG. 3 illustrates an IR spectrum of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form A.

A certain embodiment of the invention relates to the crystalline Form A of the compound of formula I as described herein, characterized by the Infrared spectrum as shown in FIG. 3.

Figure 2:
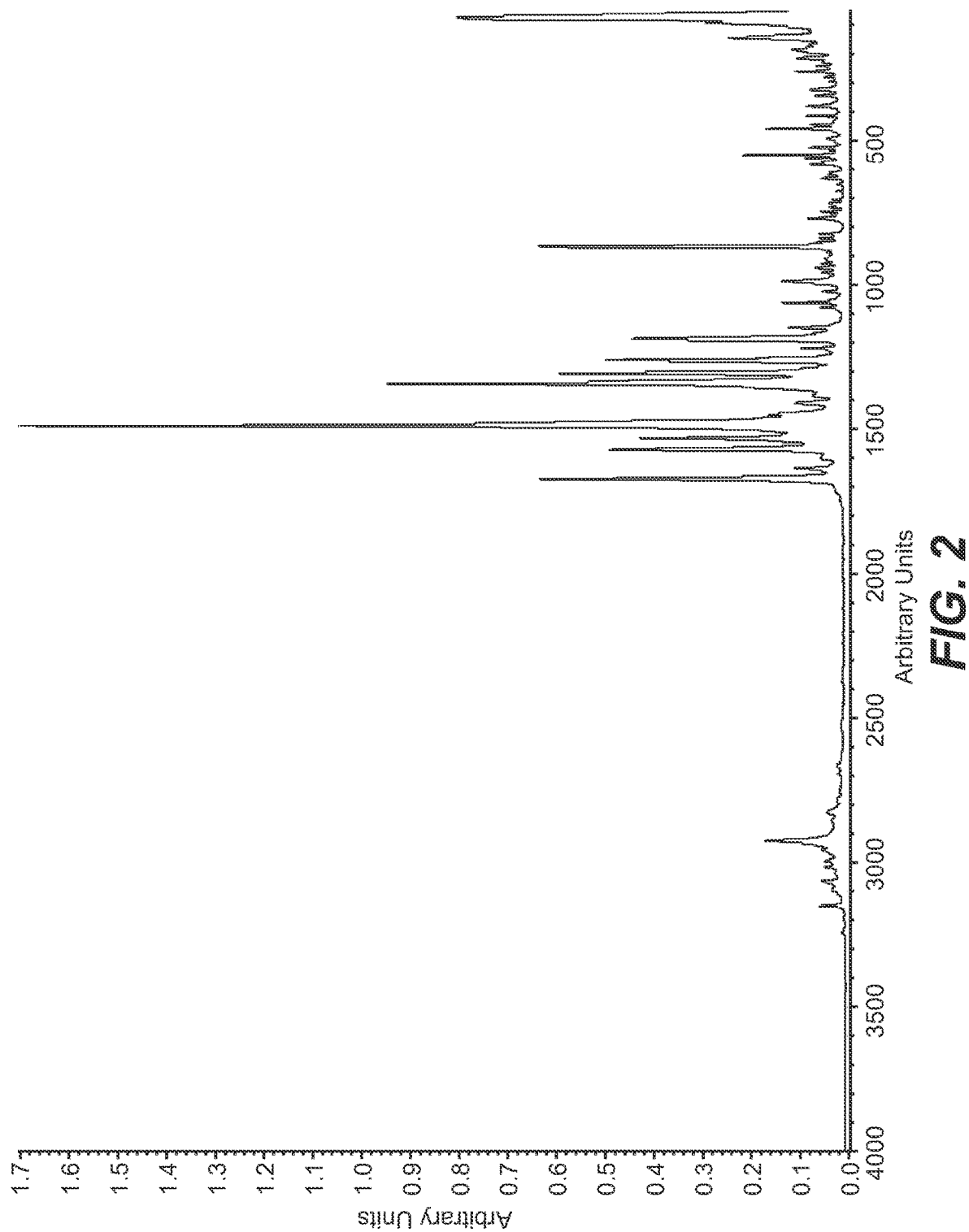
FIG. 2 illustrates a Raman spectrum of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form A.

A certain embodiment of the invention relates to the crystalline Form A of the compound of formula I as described herein, characterized by the Raman spectrum as shown in FIG. 2.

In another embodiment, crystalline polymorphic Form A of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one has a melting point above 298° C., particularly between 298° C. to 302° C., more particularly between 299° C. to 301° C., as determined by DSC using a 10 K/min heating rate and nitrogen flow. In one embodiment, crystalline polymorphic Form A of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one is anhydrous, i.e., free of water bound in the crystal lattice, and non-hygroscopic to slightly hygroscopic (<2% water uptake according to European Pharmacopoeia). In another embodiment, crystalline polymorphic Form A of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-on is substantially free of water and other solvents (in particular with ethanol <5000 ppm; $H_2O$<0.5% % wt).

In one embodiment, crystalline polymorphic Form A of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one as prepared herein is at least 90% pure, particularly at least 95% pure, more particularly at least 97% pure, even more particularly at least 99% pure, furthermore particularly at least 99.5% pure, most particularly at least 99.7% pure. By "pure" means free from contaminants including, e.g., solvents, organic impurities, or inorganic impurities.

In one embodiment, crystalline hydrate Form D of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one, is characterized by: an X-ray powder diffraction pattern which comprises characteristic peaks at one or more of about 8.4 degrees two-theta, about 12.8 degrees two-theta, about 13.9 degrees two-theta, about 19.9 degrees two-theta, about 20.8 degrees two-theta, about 22.0 degrees two-theta, about 22.6 degrees two-theta, about 23.5 degrees two-theta, about 24.4 degrees two-theta, about 25.3 degrees two-theta, about 26.1 degrees two-theta and about 27.2 degrees two-theta. In one embodiment, Form D contains two or more, three or more, four or more, or all five of these characteristic peaks. For example, Form D may contain a combination of X-ray powder diffraction pattern characteristic peaks selected at 8.4 degrees two-theta, about 12.8 degrees two-theta, about 13.9 degrees two-theta, about 19.9 degrees two-theta, about 20.8 degrees two-theta, about 22.0 degrees two-theta, about 22.6 degrees two-theta, about 23.5 degrees two-theta, about 24.4 degrees two-theta, about 25.3 degrees two-theta, about 26.1 degrees two-theta or about 27.2 degrees two-theta. In another example, there may be three characteristic peaks at 8.4±0.2 degrees two-theta, 23.5±0.2 degrees two-theta, 24.4±0.2 degrees two-theta, 25.3±0.2 degrees two-theta, or 27.2±0.2 degrees two-theta, which may be in further combination with a fourth peak. Optionally, all five peaks may be present. For example, crystalline hydrate Form D of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one is characterized by: an X-ray powder diffraction pattern which comprises characteristic peaks at one or more of 8.4±0.2 degrees two-theta, 23.5±0.2 degrees two-theta, 24.4±0.2 degrees two-theta, 25.3±0.2 degrees two-theta, or 27.2±0.2 degrees two-theta. In one embodiment, Form D contains two or more, three or more, four or more, or all five of these peaks. For example, Form D may contain a combination of X-ray powder diffraction pattern characteristic peaks at 8.4±0.2 degrees two-theta, 12.8±0.2 degrees two-theta, 13.9±0.2 degrees two-theta, 19.9±0.2 degrees two-theta, 20.8±0.2 degrees two-theta, 22.0±0.2 degrees two-theta, 22.6±0.2 degrees two-theta, 23.5±0.2 degrees two-theta, 24.4±0.2 degrees two-theta, 25.3±0.2 degrees two-theta, or 26.1±0.2 degrees two-theta and 27.2±0.2 degrees two-theta. In another example, there may be three characteristic peaks at 23.5±0.2 degrees two-theta, 24.4±0.2 degrees two-theta, and 25.3±0.2 degrees two-theta, which may be in further combination with a fourth peak. Optionally, all five peaks may be present.

Figure 4:
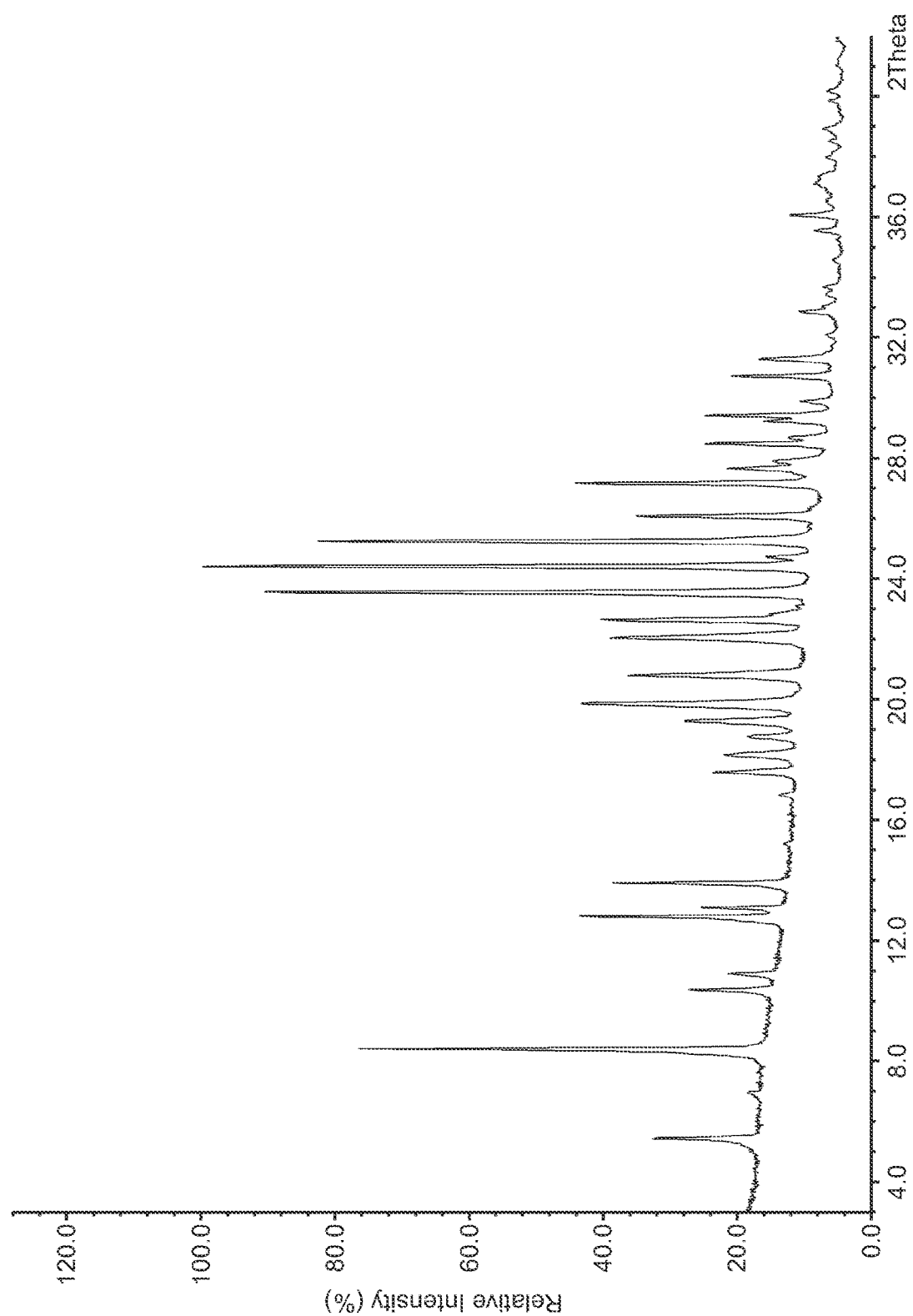
FIG. 4 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form D.

A certain embodiment of the invention relates to the crystalline hydrate Form D of the compound of formula I as described herein, characterized by the X-ray powder diffraction pattern as shown in FIG. 4.

Figure 6:
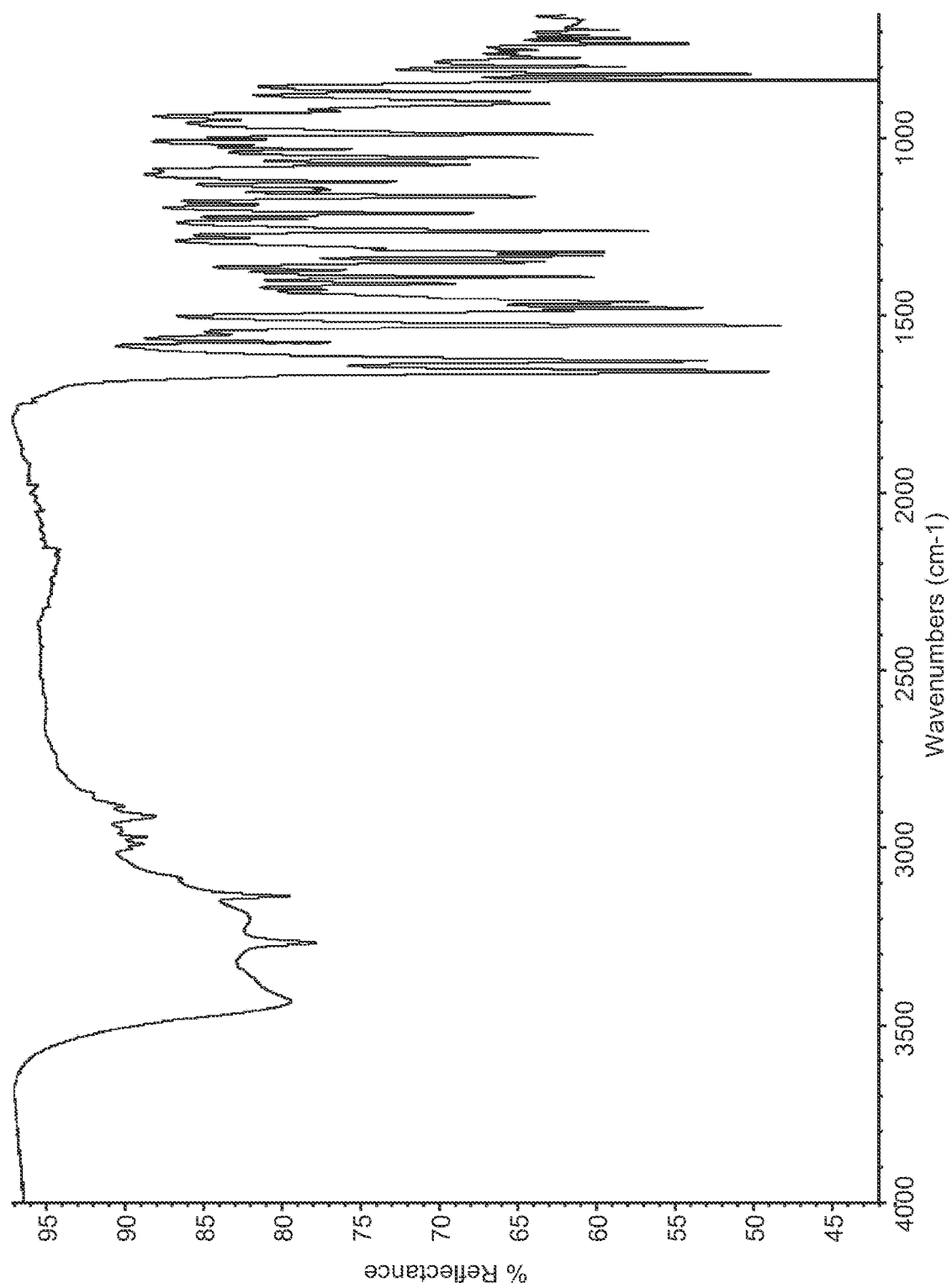
FIG. 6 illustrates an IR spectrum of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form D.
Figure 7:
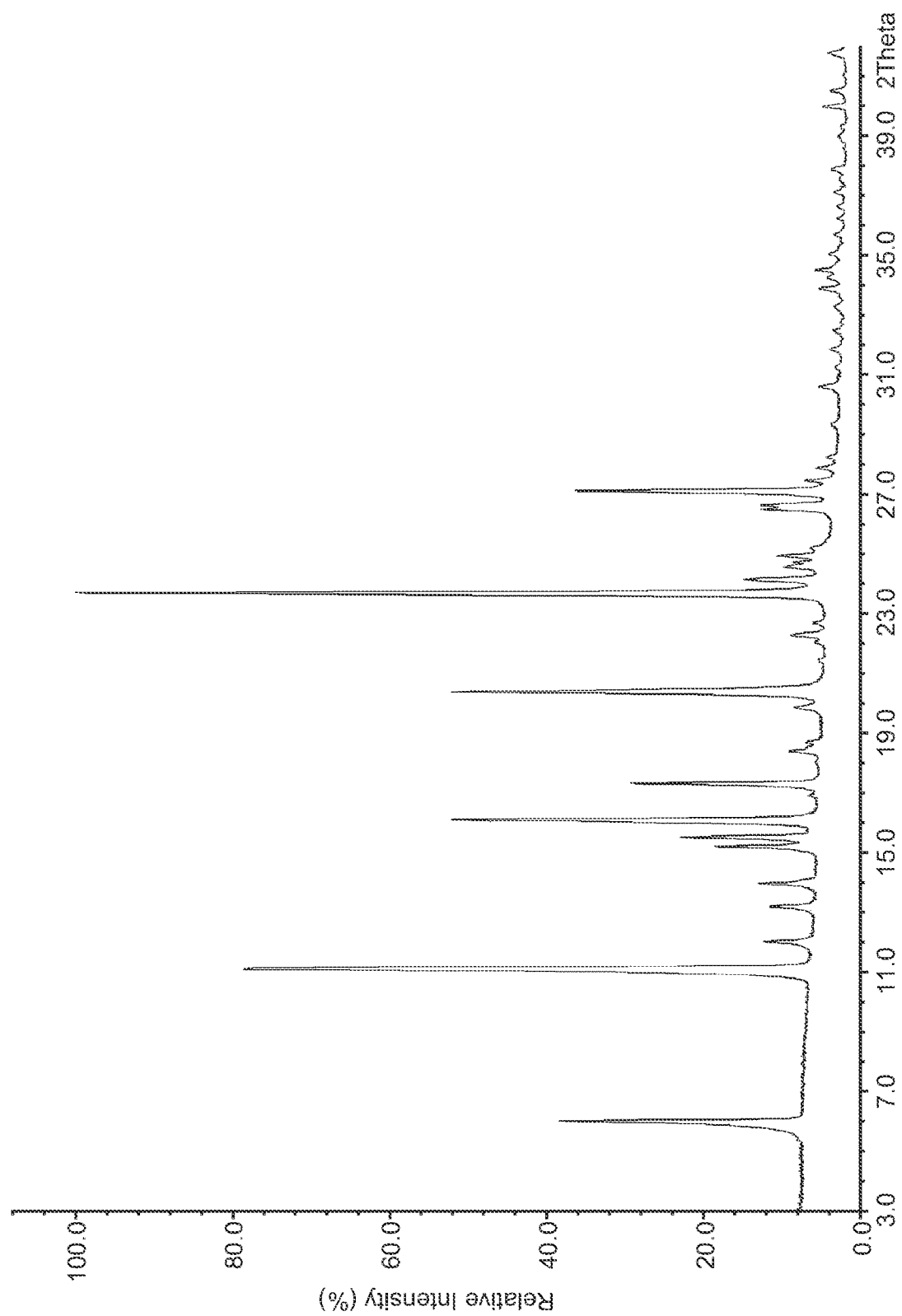
FIG. 7 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form B.
Figure 8:
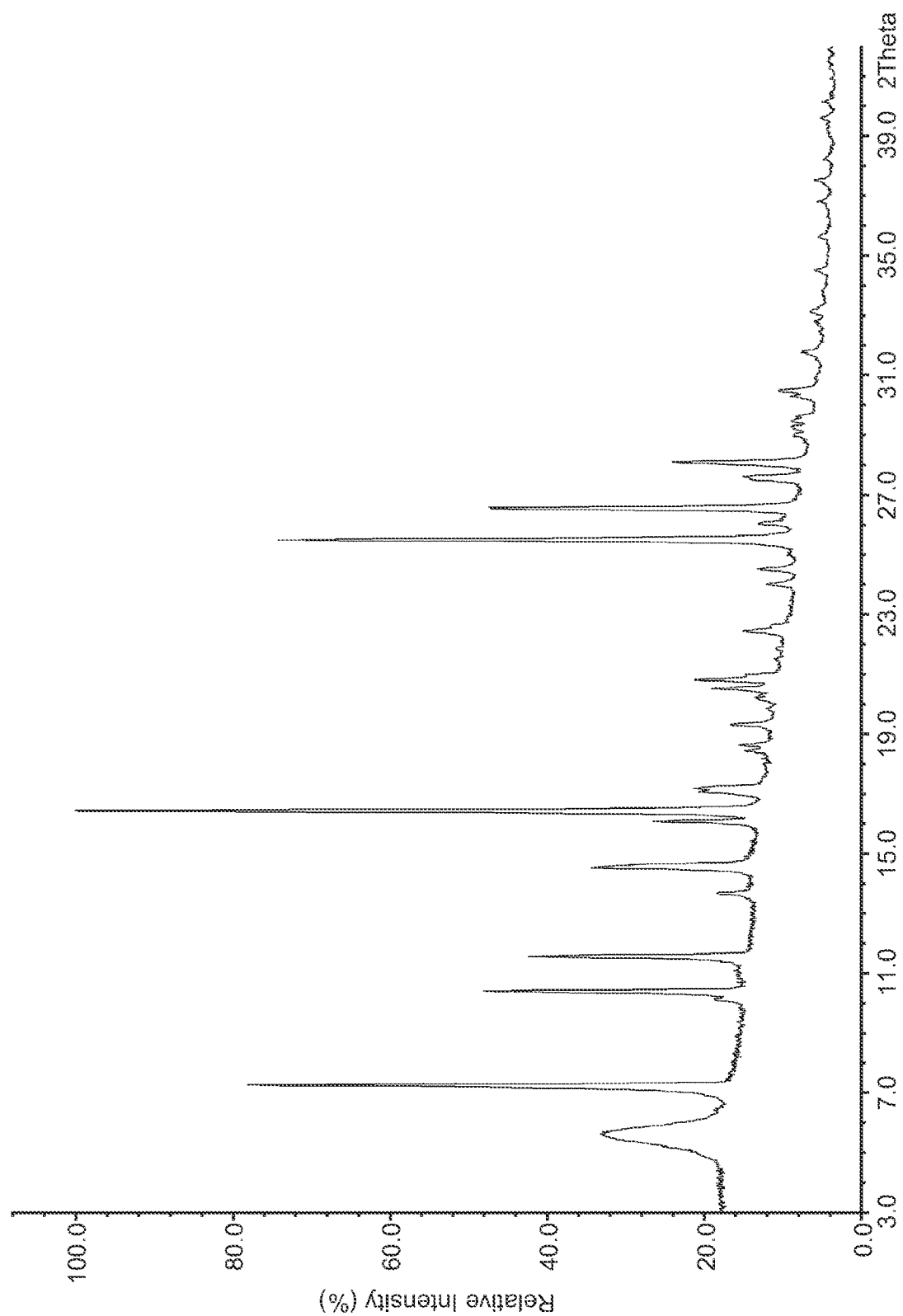
FIG. 8 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form C. The broad signal at 5-6° 2-theta is due to the Kaptonfoil.
Figure 9:
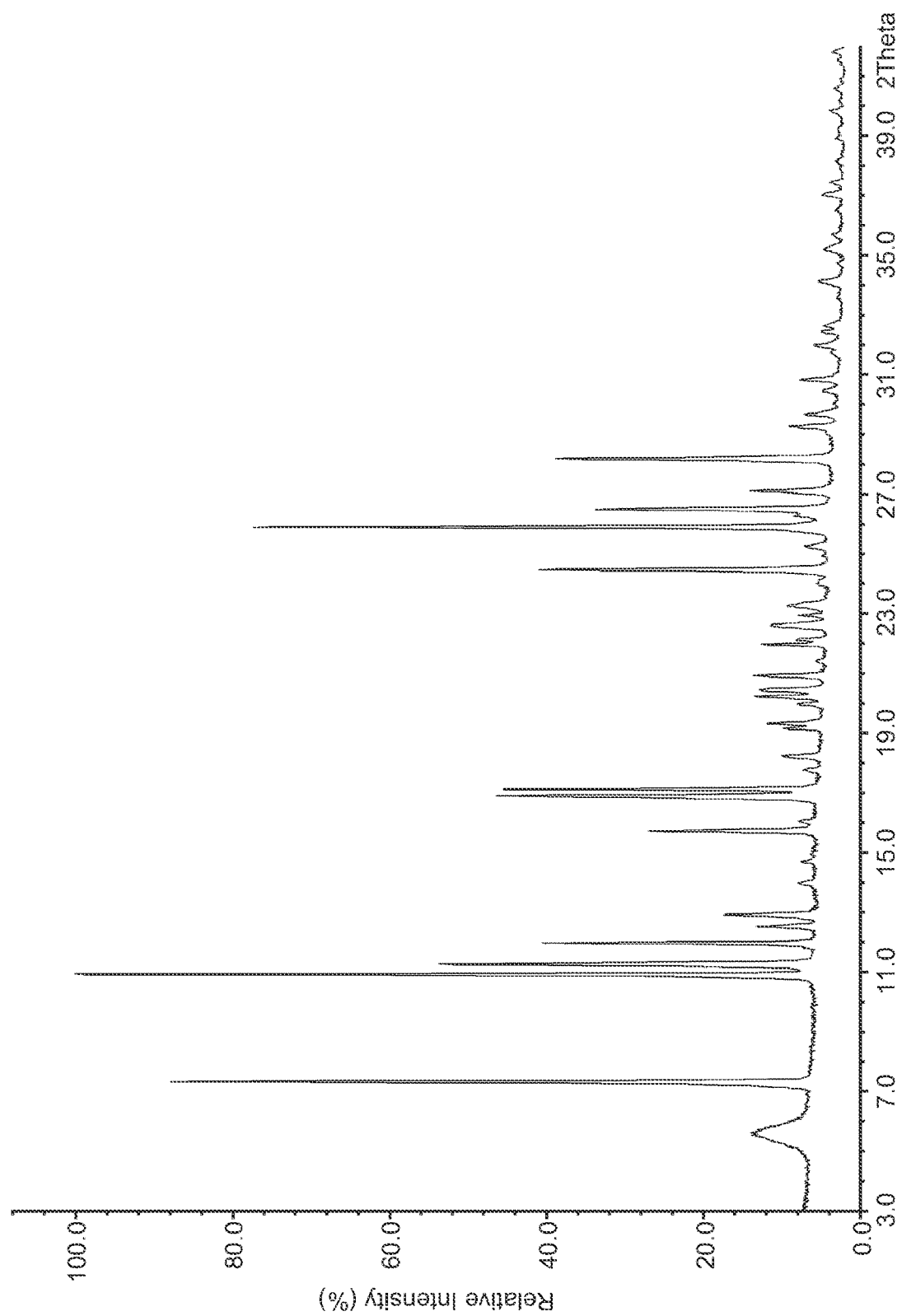
FIG. 9 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form E. The broad signal at 5-6° 2-theta is due to the Kapton foil.
Figure 10:
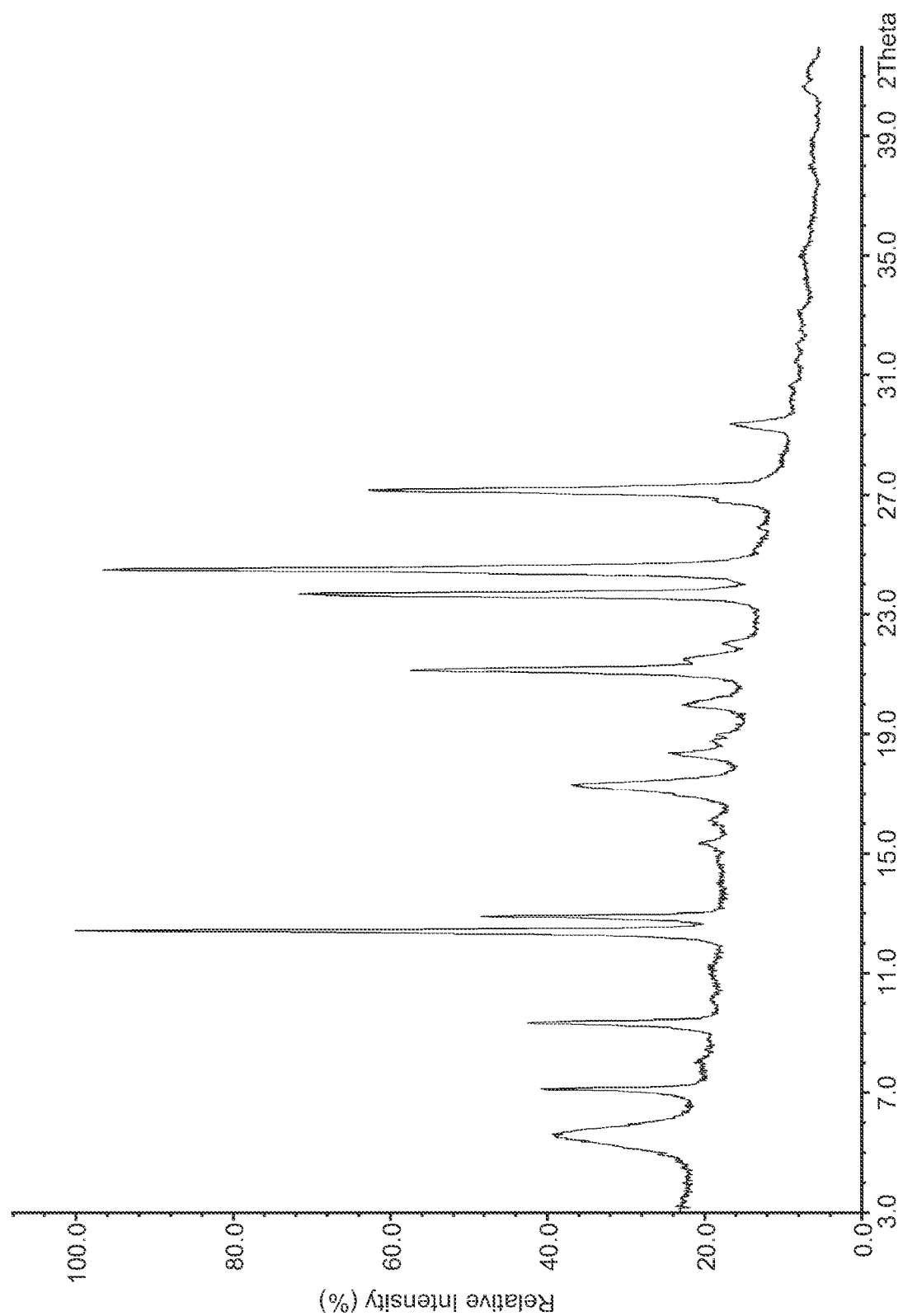
FIG. 10 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form F. The broad signal at 5-6° 2-theta is due to the Kapton foil.
Figure 11:
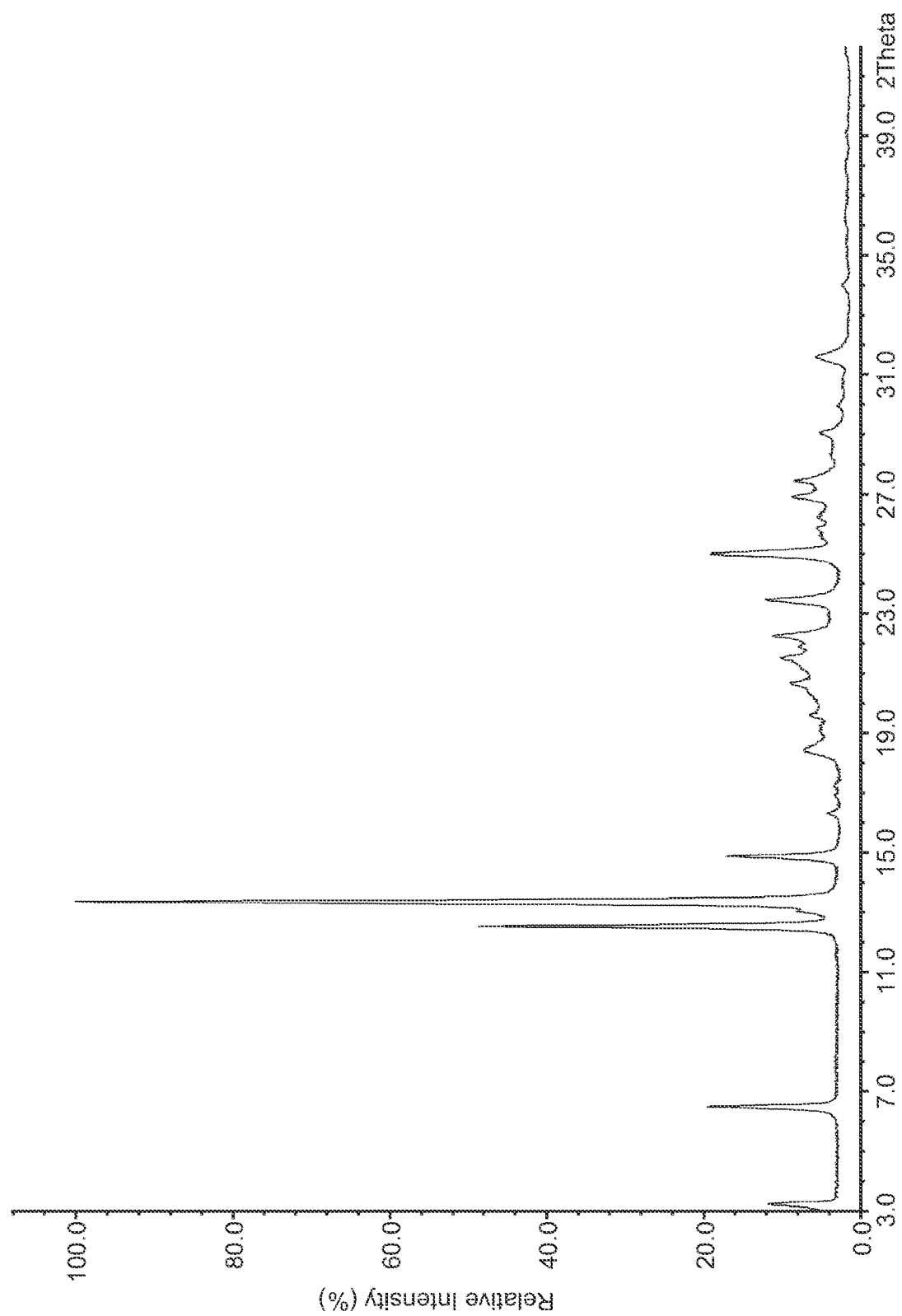
FIG. 11 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form G.
Figure 12:
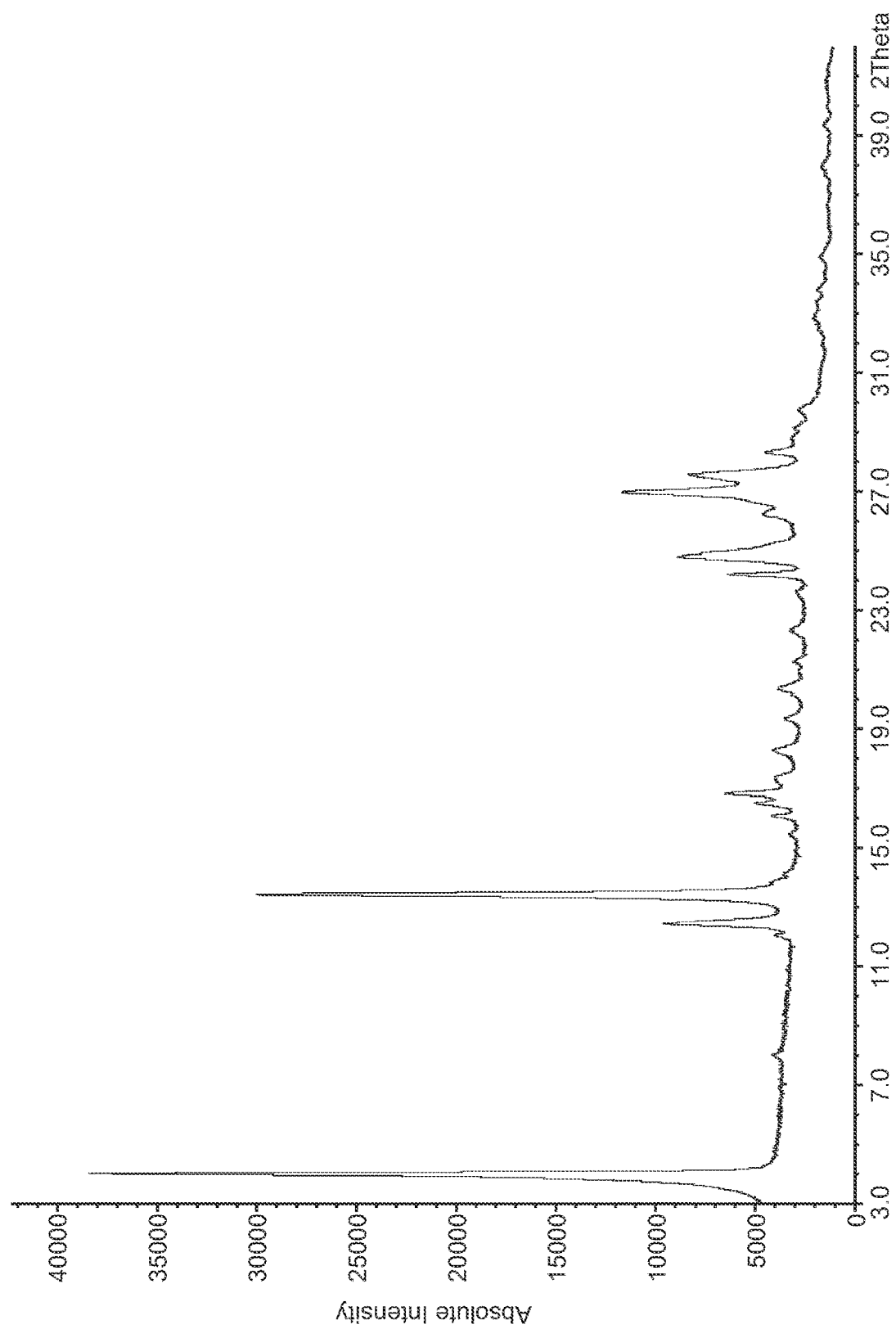
FIG. 12 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one hydrochloric acid salt.
Figure 13:
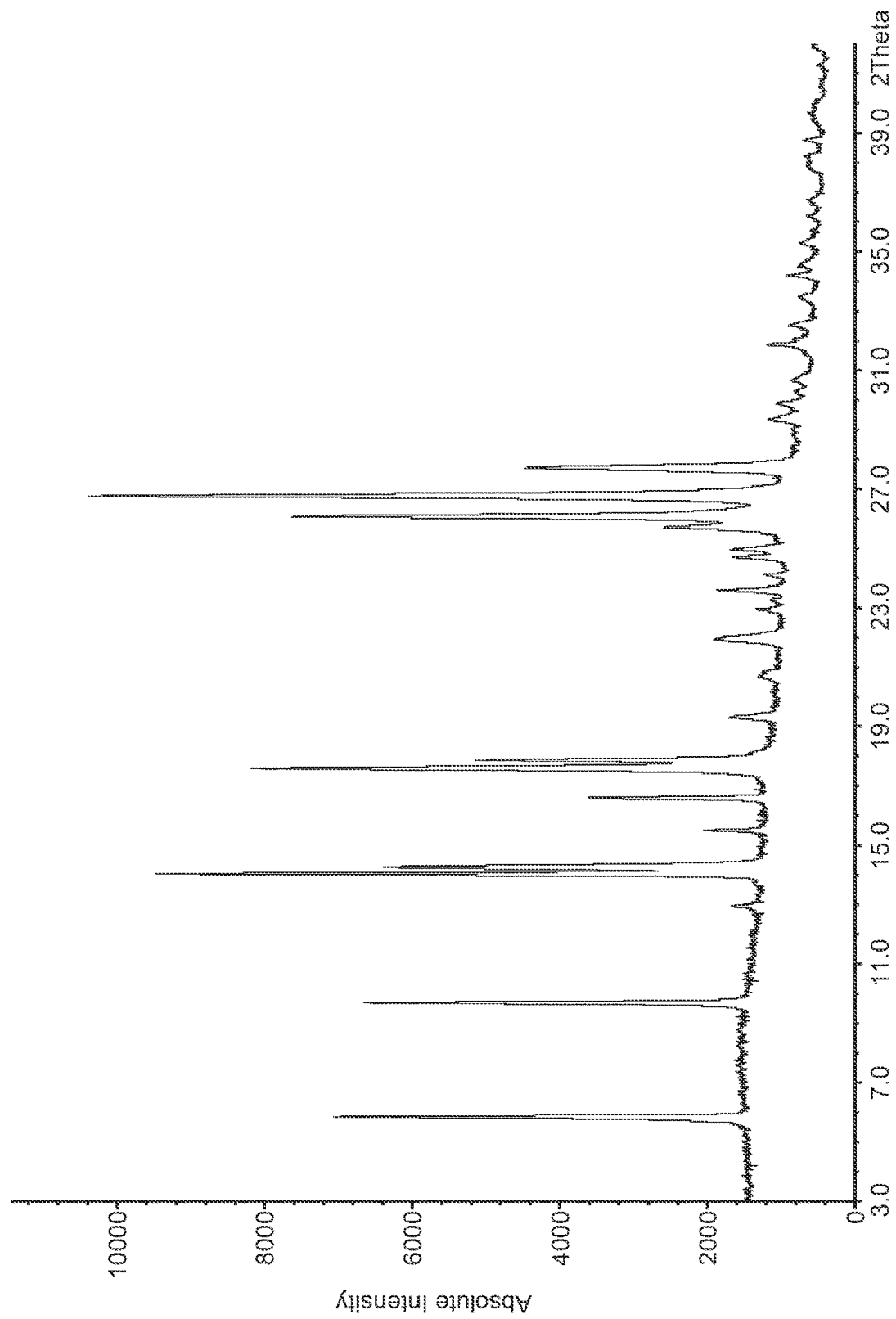
FIG. 13 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one tartaric acid salt.
Figure 14:
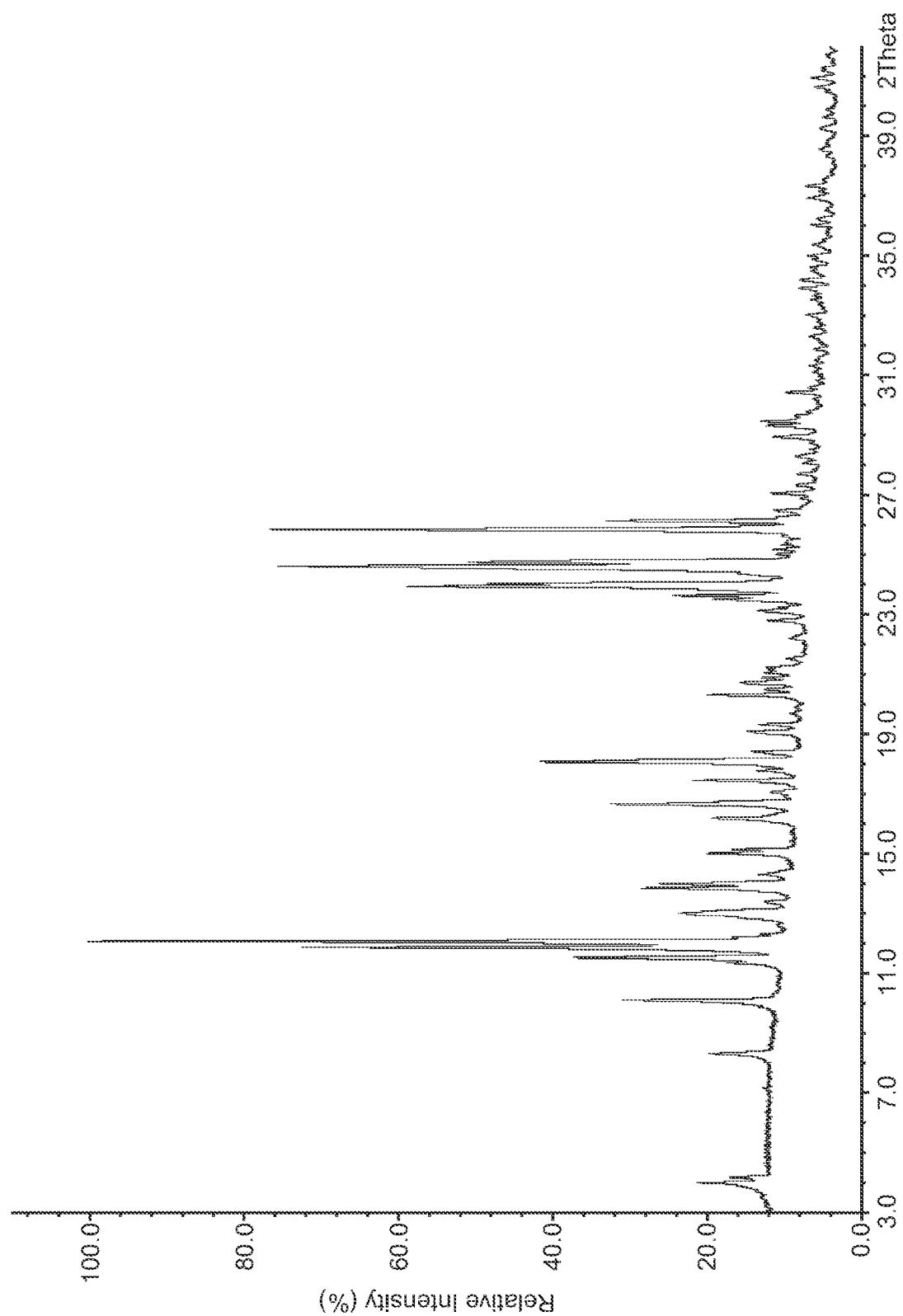
FIG. 14 illustrates an X-ray powder diffraction pattern of 7-(4,7-diazaspiro[2.5]octan-7-yl)-2-(2,8-dimethylimidazo[1,2-b]pyridazin-6-yl)pyrido[1,2-a]pyrimidin-4-one citric acid salt.

A certain embodiment of the invention relates to the crystalline Form D of the compound of formula I as described herein, characterized by the Infrared spectrum shown in as shown in FIG. 6.

Figure 5:
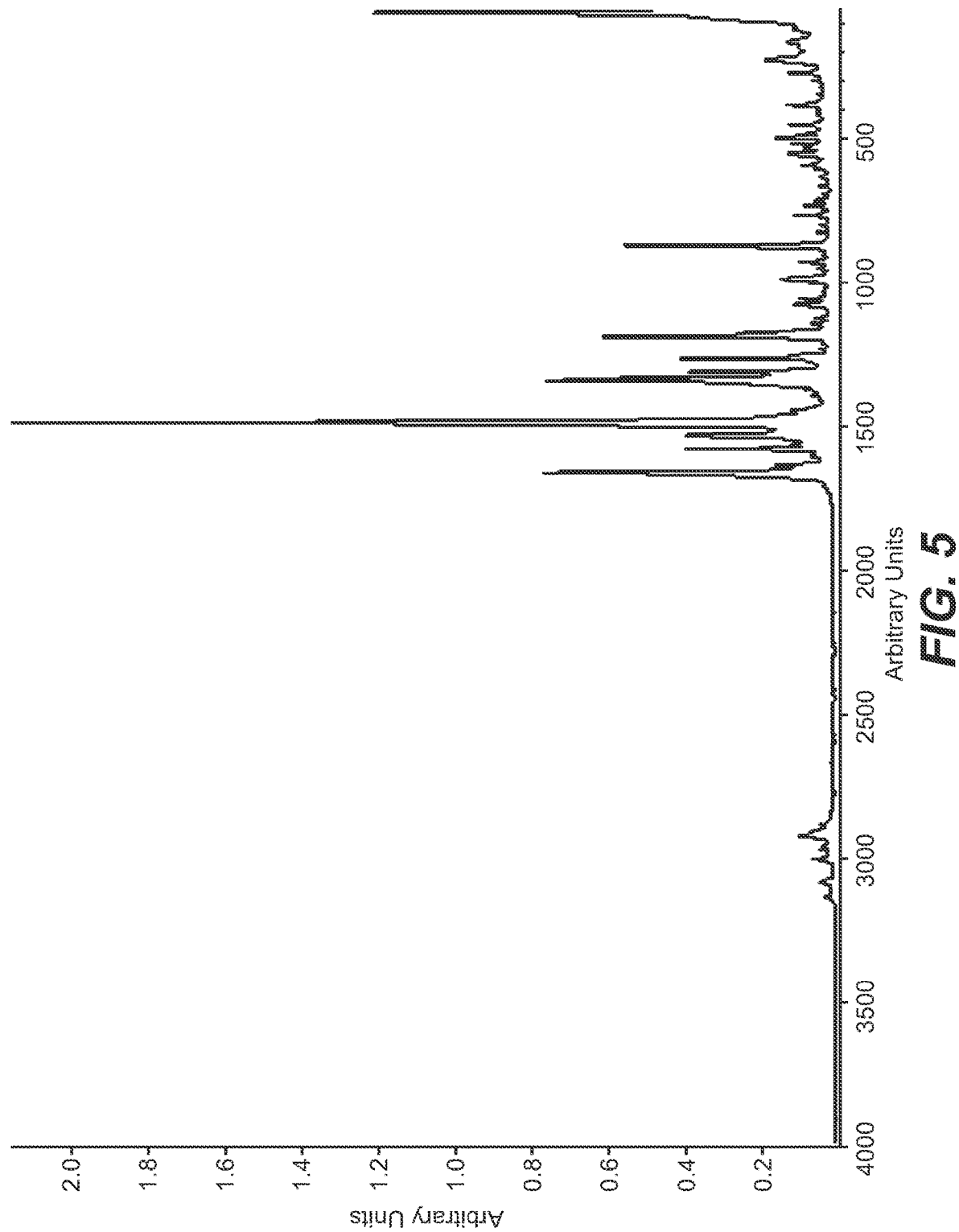
FIG. 5 illustrates a Raman spectrum of 7-(4,7-diazaspiro[2.5]octan-7-yl)-2-(2,8-dimethylimidazo[1,2-b]pyridazin-6-yl)pyrido[1,2-a]pyrimidin-4-one crystalline form, also known as Form D.

A certain embodiment of the invention relates to the crystalline Form D of the compound of formula (I) as described herein, characterized by the Raman spectrum as shown in FIG. 5.

In another embodiment, crystalline hydrate Form D of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one shows an endotherm around 80° C. to 120° C. in a standard Differential Scanning Calorimetry (DSC) run using a 10 K/min heating rate, indicating the loss of hydrate water. Crystalline hydrate Form D of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one is a trihydrate.

In one embodiment, crystalline hydrate Form D of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one as prepared herein is at least 90% pure, at least 95% pure, at least 97% pure, about 98% pure. In a further embodiment the hydrate Form D of compound of formula (I), 7-(4,7-diazaspiro[2.5]octan-7-yl)-2-(2,8-dimethylimidazo[1,2-b]pyridazin-6-yl)pyrido[1,2-a]pyrimidin-4-one as prepared herein contains at most 1% of solvent, in particular of ethanol and 1-propanol.

The present application discloses a process for the preparation of a compound of formula (I):

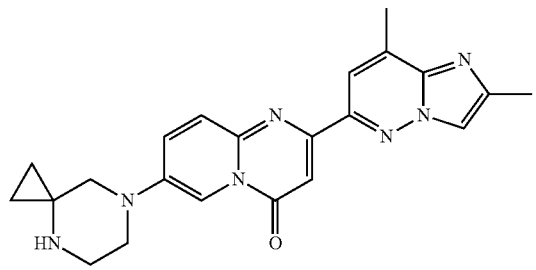

which comprises reacting compound of formula (II):

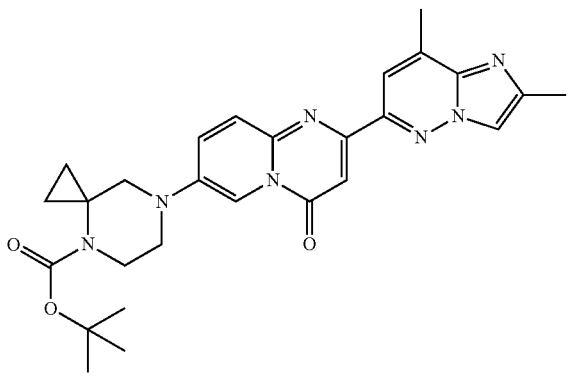

with a strong acid, in particular HCl. The process as disclosed herein, wherein the HCl is made in situ in the presence of 1-propanol and acetyl chloride.

In particular, the preparation of compound of formula (I) is being carried out in a solvent such as an alcohol, an aqueous alcohol, ethyl-acetate, 1-propyl acetate, toluene, acetonitrile, THF or dichloromethane. More preferably the preparation of compound of formula (I) is being carried out in the presence of 1-propanol and toluene.

Furthermore, the present application discloses a process as described herein, wherein 3 to 15 equivalents, more particularly 4 to 8 equivalents, most particularly 5 equivalents of strong acid, in particular wherein the strong acid is HCl, with respect to compound of formula (II) is used.

In particular, the present application discloses a process as described above for the preparation of compound of formula (I), wherein the reaction is carried out at a temperature between 20° C. to 100° C., particularly between 60° C. to 80° C., more particularly at 75° C.

7-(4,7-diazaspiro[2.5]octan-7-yl)-2-(2,8-dimethylimidazo[1,2-b]pyridazin-6-yl)pyrido[1,2-a]pyrimidin-4-one is a valuable pharmaceutical compound as described in WO2015173181. It can be prepared according to WO201573181 as well.

Any open valency appearing on a carbon, oxygen, sulfur or nitrogen atom in the structures herein indicates the presence of a hydrogen, unless indicated otherwise.

The application also discloses further forms of risdiplam that have been identified, such as:

a) Form B as metastable polymorph b) Form C as a monohydrate c) Form E as a trihydrate
d) Form F as a hydrate
e) Form G as a metastable polymorph.

The present application also discloses salt of risdiplam such as hydrochloric acid, tartaric acid and citric acid salt of 7-(4,7-diazaspiro[2.5]octan-7-yl)-2-(2,8-dimethylimidazo[1,2-b]pyridazin-6-yl)pyrido[1,2-a]pyrimidin-4-one.

Unless otherwise stated, the following terms used in the specification and claims have the meanings given below:

"about" or "approximately" refers a range values that fall within 5%, greater or less than the stated reference value. More particularly "about" or "approximately" refers to ±0.2° degrees two-theta or ±0.5° C.

"ambient conditions" refers conditions as experienced in a standard laboratory, e.g. atmospheric pressure, air, ambient temperature between 18° C. and 28° C., humidity between 30% rH and 80% rH.

"Compound of formula (I)" refers to:

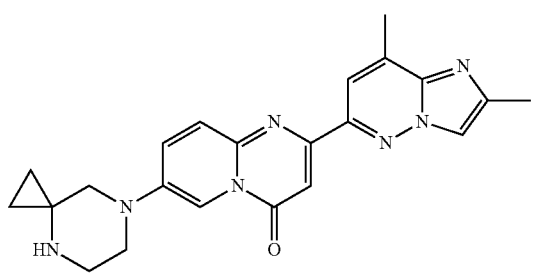

(I)

also known as 7-(4,7-diazaspiro[2.5]octan-7-yl)-2-(2,8-dimethylimidazo[1,2-b]pyridazin-6-yl)pyrido[1,2-a]pyrimidin-4-one or 7-(4,7-diazaspiro[2.5]octan-7-yl)-2-(2,8-dimethylimidazo[1,2-b]pyridazin-6-yl)-4H-pyrido[1,2a]pyrimidin-4-one. Compound of formula (I) is also known as risdiplam, RG7916 or RO7034067. Herein compound of formula (I)'s name or reference can be interchangeably be used.

"Form A" as used herein refers to the crystalline anhydrous polymorphic Form A of 7-(4,7-diazaspiro[2.5]octan-7-yl)-2-(2,8-dimethylimidazo[1,2-b]pyridazin-6-yl)pyrido[1,2-a]pyrimidin-4-one.

"Form D" as used herein refers to the crystalline hydrate Form D of 7-(4,7-diazaspiro[2.5]octan-7-yl)-2-(2,8-dimethylimidazo[1,2-b]pyridazin-6-yl)pyrido[1,2-a]pyrimidin-4-one. Form D contains 3 mol equivalents of water. Form D is a Trihydrate.

"$(C_1-C_8)$alkyl" refers to a branched or straight hydrocarbon chain, such as methyl, ethyl, n-propyl, isopropyl, n-butyl, isobutyl, sec-butyl and t-butyl, pentyl, hexyl, heptyl or octyl. "$(C_1-C_3)$alkyl" refers methyl, ethyl, n-propyl or isopropyl.

"alcohol" refers to a benzyl alcohol, aminoethanol or an $(C_{1-8})$alkyl (more particularly $(C_1-C_3)$alkyl) as defined above substituted by one or two hydroxy groups, more particularly substituted by one hydroxy group. Examples of alcohols include, but are not limited to, methanol, ethanol, isopropanol, 1-propanol, propylenglycol, 1-butanol, 2-butanol, t-butanol, benzyl alcohol, 2-aminoethanol and octanol. Particularly, alcohol refers to methanol, ethanol, 1-propanol or benzyl alcohol, most particularly to 1-propanol.

"ambient conditions" refers to conditions as experienced in a standard laboratory, e.g. atmospheric pressure, air, ambient temperature between 18° C. and 28° C., humidity between 30% rH and 80% rH.

"base" refers to a chemical compound that deprotonates another compound when reacted with it. Suitable bases for use in accordance with this disclosure include but are not limited to, e.g., an organic base and basic alkali metal salts. In particular, an organic base includes nitrogen-containing heterocycle and tertiary amines. Examples of nitrogen-containing heterocycle include pyridine, imidazole and benzimidazole. In some embodiments, the tertiary amines include triethylamine, N-methylmorpholine and diisopropylethylamine. In some embodiments, the basic alkali metal salts include, e.g., sodium carbonate ($Na_2CO_3$), potassium carbonate ($K_2CO_3$), sodium bicarbonate ($NaHCO_3$), sodium hydroxide (NaOH), sodium and potassium alkoxides including, but not limited to, sodium and potassium t-butoxide, 1-propoxide, 2-propoxide, ethoxide, methoxide, and the like, sodium amide ($NaNH_2$), potassium amide ($KNH_2$), and the like.

"crystallization" and "recrystallization" may be used interchangeably; referring to a process wherein a chemical compound that is dissolved or suspended in a solvent system leads to a stable polymorph or crystalline form of a particular chemical compound. For example, the crystallization steps can be done by forming a crystal with a solvent and an anti-solvent.

The terms "halo", "halogen" and "halide", which may be used interchangeably, refer to a substituent chloro, bromo, or iodo.

"strong acid" refers to an acid that dissociates completely in an aqueous solution with a pH≤2. The strong acids include, but are not limited to: sulphuric acid ($H_2SO_4$), hydrohalogenic acid (i.e. HX" wherein X" is I, Br, Cl or F), nitric acid ($HNO_3$), phosphoric acid ($H_3PO_4$) and combinations thereof. Particularly, the strong acid is hydrohalogenic acid, wherein X" is Br or Cl. Most particularly, the strong acid is HCl.

"Nickel catalyst" refers to catalysts comprising nickel or nickel oxides or mixtures thereof. Example of Nickel catalyst is Raney-nickel catalyst (Ra—Ni).

The term "optional" or "optionally" denotes that a subsequently described event or circumstance can but need not occur, and that the description includes instances where the event or circumstance occurs and instances in which it does not.

"palladium catalyst" refers to reagent which is a source of palladium zero (Pd(0)).

Suitable sources of Pd(0) comprises but are not limited to palladium bis(dibenzylideneacetone) ($Pd(dba)_2$), bis(triphenylphosphine)palladium(II) dichloride ($Pd(PPh_3)_2Cl_2$), palladium acetate ($Pd(OAc)_2$), palladium chloride ($PdCl_2$), tetrakis (triphenyl-phosphino) palladium ($Pd(PPh_3)_4$), 1,2 bis(diphenylphosphino) ethane palladium ($Pd(dppe)_2$), 1,3-bis(diphenylphosphino)-propane palladium ($Pd(dppp)_2$), dichloro-1,3-bis(diphenylphosphino)-propane palladium ($PdCl_2(dppp)$),1,4-bis(diphenyl-phosphino) butane palladium, 1,1-bis (diphenylphosphine)-ferrocen dichloro palladium ($PdCl_2(dppf)$), palladium on carbon, $Pd(OH)_2$ on carbon, tris(dibenzylideneacetone)dipalladium(O) ($Pd_2(dba)_3$), bis(acetonitrile)-palladium(II) dichloride ($PdCl_2(CH_3CN)_2$), cyclopentadienyl allyl palladium, allylpalladium(II) chloride dimer ($Pd(allyl)Cl)_2$), (2-butenyl)chloropalladium dimer, (2-methylallyl) palladium(II) chloride dimer, palladium(1-phenylallyl)chloride dimer, di-µ-chlorobis[2'-(amino-N)[1,1'-biphenyl]-2-yl-C]dipalladium(II), di-µ-chlorobis[2-[(dimethylamino)methyl]phenyl-C,N]dipalladium (II) or dichloro[9,9-dimethyl-4,5-bis(diphenylphosphino)

xanthene]palladium (Pd(XantPhos)Cl$_2$). In particular the palladium catalyst refers to Pd(OAc)$_2$, Pd(PPh$_3$)$_4$, Pd(PPh$_3$)$_2$Cl$_2$, Pd$_2$(dba)$_3$, (Pd(XantPhos)Cl$_2$) or PdCl$_2$(dppf)). More particularly the palladium catalyst is Pd(OAc)$_2$, Pd$_2$(dba)$_3$, (Pd(XantPhos)Cl$_2$) or PdCl$_2$(dppf).

"XRPD" refers the analytical method of X-Ray Powder Diffraction. The repeatability of the angular values is in the range of 2Theta±0.2°. The term "approximately" given in combination with an angular value denotes the repeatability which is in the range of 2Theta±0.2°. The relative XRPD peak intensity is dependent upon many factors such as structure factor, temperature factor, crystallinity, polarization factor, multiplicity, and Lorentz factor. Relative intensities may vary considerably from one measurement to another due to preferred orientation effects. According to USP 941 (US Pharmacopoeia, 37th Edition, General Chapter 941), relative intensities between two samples of the same material may vary considerably due to "preferred orientation" effects. Anisotropic materials adopting preferred orientation will lead to anisotropic distribution of properties such as modulus, strength, ductility, toughness, electrical conductivity, thermal expansion, etc., as described e.g. in Kocks U. F. et al. (Texture and Anisotropy: Preferred Orientations in Polycrystals and Their Effect on Materials Properties, Cambridge University Press, 2000). In XRPD but also Raman spectroscopy, preferred orientations cause a change in the intensity distribution. Preferred orientation effects are particularly pronounced with crystalline APIs of relatively large particle size.

"characteristic peak" refers to the presence of the powder X-ray diffraction peak definitively identifies the 7-(4,7-diazaspiro[2.5]octan-7-yl)-2-(2,8-dimethylimidazo[1,2-b]pyridazin-6-yl)pyrido[1,2-a]pyrimidin-4-one as the referenced crystalline form (Form A or Form D). Typically, the powder X-ray diffraction analysis is conducted at ambient conditions in transmission geometry with a STOE STADI P diffractometer (Cu Kai radiation, primary monochromator, silicon strip detector, angular range 3 to 42 degrees two-theta, approximately 30 minutes total measurement time). The samples (approximately 10 to 50 mg) are prepared between thin polymer films and are analyzed without further processing (e.g. grinding or sieving) of the substance.

"Polymorph" refers to crystalline forms having the same chemical composition but different spatial arrangements of the molecules, atoms, and/or ions forming the crystal. In general, reference throughout this specification will be to a polymorph 7-(4,7-diazaspiro[2.5]octan-7-yl)-2-(2,8-dimethylimidazo[1,2-b]pyridazin-6-yl)pyrido[1,2-a]pyrimidin-4-one.

The term "Solvate" refers herein to a molecular complex comprising a compound of formula (I) and a stoichiometric or non-stoichiometric amount of one or more solvent molecules (e.g., ethanol).

"Hydrate" refers herein to a solvate comprising a compound of formula (I) and a stoichiometric or non-stoichiometric amount of water.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

"Transition metal hydrogenation catalyst" refers to a transition metal hydrogenation catalyst, which acts in a different phase than the substrate. Especially the transition metal hydrogenation catalyst is in the solid phase. In particular, while the transition metal hydrogenation catalyst is in the solid phase, the reactants are in the liquid phase. The transition metal hydrogenation catalyst contains a transition metal, which forms one or more stable ions, which have incompletely filled d orbitals (i.e. Pd, Pt, Rh, Au, Ni, Co, Ru, Ir, V, Fe) in particular noble metal, such as Pd, Pt, Rh or Au. In these catalysts the transition metal is in particular "supported", which means that the catalyst is dispersed on a second material that enhances the effectiveness. The "support" can be merely a surface on which the metal is spread to increase the surface area. The supports are porous materials with a high surface area, most commonly alumina or various kinds of carbon. Further examples of supports include, but are not limited to, silicon dioxide, titanium dioxide, calcium carbonate, barium sulfate, diatomaceous earth and clay. The metal itself can also act as a support, if no other support is present. More specifically the term "Transition metal hydrogenation catalyst" includes but is not limited to, a Raney catalyst (e.g. Ra—Ni, Ra—Co) Pd/C, Pd(OH)$_2$/C, Au/TiO$_2$, Rh/C, Ru/Al$_2$O$_3$, Ir/CaCO$_3$, Pt—V/C or Pt/C, in particular Pt—V/C.

"Tertiary amine" refers to an amine of formula R$^a$N(R$^b$)R$^c$ wherein R$^a$, R$^b$ and R$^c$ independently are selected from (C$_1$-C$_6$)alkyl or phenyl. Representative examples include, but are not limited to, triethylamine, tributylamine, di-ethyl-methylamine, dimethyl-ethylamine, di-isopropylethylamine, N,N-dimethylaniline and methylethylbutylamine. Preferably, the tertiary amine is chosen from triethylamine or di-isopropylethylamine. The most preferred tertiary amine is triethylamine.

The term "treating", "contacting" or "reacting" used interchangeably refers to adding, bringing together or mixing two or more chemical substances (referred usually as reagents or reactants), more particularly under appropriate conditions, to produce the indicated and/or the desired product. It should be appreciated that the reaction which produces the indicated and/or the desired product may not necessarily result directly from the combination of two or more reagents which were initially added, i.e., there may be one or more intermediates which are produced in the mixture which ultimately leads to the formation of the indicated and/or the desired product.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The terms "individual" or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The terms "treating" or "treatment" of a disease state include inhibiting the disease state, i.e., arresting the development of the disease state or its clinical symptoms, or relieving the disease state, i.e., causing temporary or permanent regression of the disease state or its clinical symptoms.

The term "spinal muscular atrophy" (or SMA) relates to a disease caused by an inactivating mutation or deletion in the SMN1 gene on both chromosomes, resulting in a loss of SMN1 gene function. Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

The term "treating spinal muscular atrophy (SMA)" or "treatment of spinal muscular atrophy (SMA)" includes one or more of the following effects: (i) reduction or amelioration of the severity of SMA; (ii) delay of the onset of SMA; (iii) inhibition of the progression of SMA; (iv) reduction of hospitalization of a subject; (v) reduction of hospitalization length for a subject; (vi) increase of the survival of a subject; (vii) improvement of the quality of life of a subject; (viii) reduction of the number of symptoms associated with SMA; (ix) reduction of or amelioration of the severity of one or more symptoms associated with SMA; (x) reduction of the duration of a symptom associated with SMA; (xi) prevention of the recurrence of a symptom associated with SMA; (xii) inhibition of the development or onset of a symptom of SMA; and/or (xiii) inhibition of the progression of a symptom associated with SMA.

More particular, the term "treating SMA" denotes one or more of the following beneficial effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In further detail, the term "treating SMA" refers to the functional ability or retention of the functional ability for a human infant or a human toddler to sit up unaided or for a human infant, a human toddler, a human child or a human adult to stand up unaided, to walk unaided, to run unaided, to breathe unaided, to turn during sleep unaided, or to swallow unaided.

A "pharmaceutically acceptable carrier" refers to an ingredient in a pharmaceutical composition, other than an active ingredient, which is nontoxic to a subject. A pharmaceutically acceptable carrier includes, but is not limited to, a buffer or acidifier, excipient, stabilizer, or preservative.

The term "buffer" or "buffer system" denotes a pharmaceutically acceptable excipient or excipient mixture, which stabilizes the pH of a pharmaceutical preparation. Suitable buffers are well known in the art and can be found in the literature. Particular pharmaceutically acceptable buffers comprise citric buffer, malate buffer, maleate buffer, or tartrate buffer, most particularly tartrate buffer. Particular buffer systems of the invention combinations of organic acid and selected salts thereof, e.g. tribasic sodium citrate and citric acid, malic acid and sodium malate, potassium sodium tartrate and tartaric acid, or disodium tartrate and tartaric acid, particularly potassium sodium tartrate and tartaric acid. Alternatively, the organic acid (particularly tartaric acid) can be employed alone as "acidifier" instead of the combination of acid and the corresponding salt. Independently from the buffer used, the pH can be adjusted with an acid or a base known in the art, e.g., hydrochloric acid, acetic acid, phosphoric acid, sulfuric acid and citric acid, sodium hydroxide and potassium hydroxide. Particular acidifier is tartaric acid.

The term "antioxidant" denotes pharmaceutically acceptable excipients, which prevent oxidation of the active pharmaceutical ingredient. Antioxidants comprise ascorbic acid, glutathione, cysteine, methionine, vitamin E TPGS, EDTA.

The term "surfactant" denotes a pharmaceutically acceptable excipient which is used to protect protein compositions against mechanical stresses like agitation and shearing. Examples of pharmaceutically acceptable surfactants include poloxamers, polysorbates, polyoxyethylene alkyl ethers (BRIJ®), alkylphenylpolyoxyethylene ethers (TRITON-X®) or sodium dodecyl sulfate (SDS).

The term "poloxamer" denotes non-ionic triblock copolymers composed of a central hydrophobic chain of poly (propylene oxide) (PPO) flanked by two hydrophilic chains of poly(ethylene oxide) (PEO), each PPO or PEO chain can be of different molecular weights. Poloxamers are also known by the trade name Pluronics. Particular Poloxamer is Poloxamer 188, a poloxamer wherein the PPO chain has a molecular mass of 1800 g/mol and a PEO content of 80% wt.

The term "polysorbate" denotes oleate esters of sorbitol and its anhydrides, typically copolymerized with ethylene oxide. Particular polysorbates are Polysorbate 20 (poly (ethylene oxide) (20) sorbitan monolaurate, TWEEN 20®) or Polysorbate 80 (poly(ethylene oxide) (80) sorbitan monolaurate, TWEEN 80®).

The "hydrophilic-lipophilic balance" (HLB) value denotes the degree of hydrophilicity of a non-ionic surfactant. The HLB value is determined by the ratio between the molecular mass of the hydrophilic portion of the surfactant molecule and its overall molecular mass, as described by Griffin W. C., Journal of the Society of Cosmetic Chemists (1949) 1:311.

The term "hydrophilic" denotes the capacity of a molecule or portion of a molecule to interact with polar solvents, in particular with water, or with other polar moieties driven by hydrogen bonding, dipole-ion interactions and/or dipole-dipole interactions.

The terms "lipophilic" and "hydrophobic" can be used interchangeably and denote the tendency of a molecule or portion of a molecule to dissolve in non-polar environment such as fats, oils, and non-polar solvents driven by London dispersion forces.

The term "mg/ml" according to the pharmaceutical composition of the invention refers to the amount of either compound of formula (I) or the individual excipient according to the formulation in milligram per volume of solvent, in particular wherein the solvent is water, most particularly purified water in the constituted solution in milliliter.

The present application discloses a process for the preparation of a compound of formula (II)

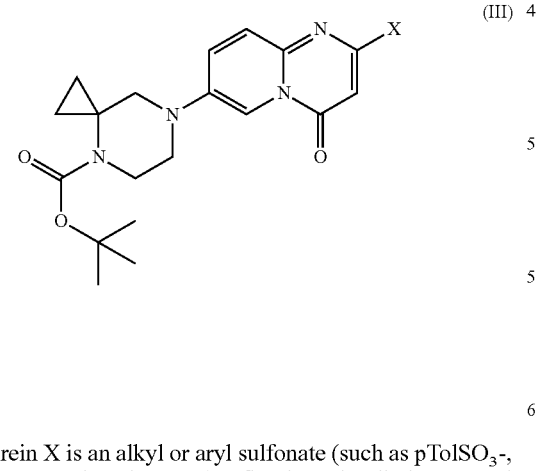
(II)

which comprises reacting a compound of formula (III)

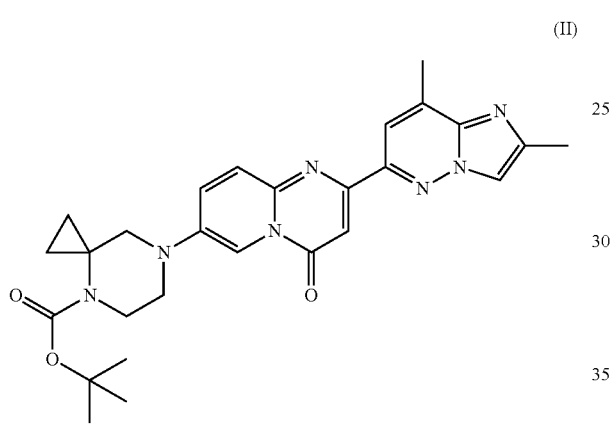
(III)

wherein X is an alkyl or aryl sulfonate (such as pTolSO$_3$-, CH$_3$SO$_3$—, phenyl-SO$_3$—), fluorinated alkyl or aryl sulfonates (such as CF$_3$SO$_3$—, nonaflate), or a halide (such as Cl, Br, or I), with a compound of formula (III'), (III$_a$') or (III$_b$'), in particular with a compound of formula

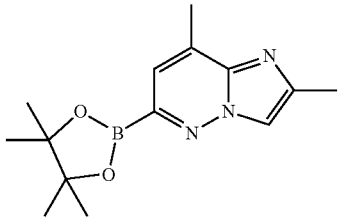
(III')

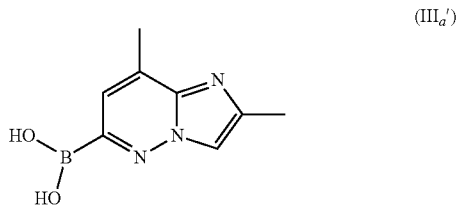
(III$_a$')

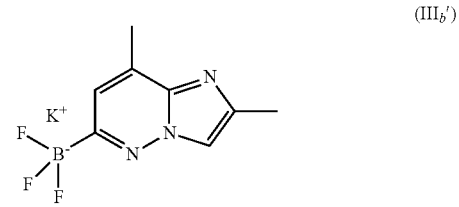
(III$_b$')

in the presence of a palladium catalyst or nickel catalyst, in particular in presence of a palladium catalyst.

More particularly, the present application discloses a process for the preparation of a compound of formula (II)

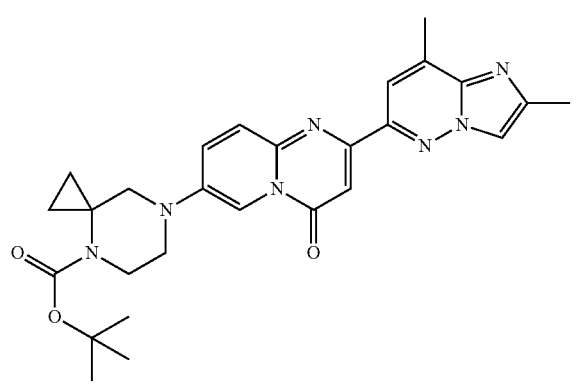
(II)

which comprises reacting a compound of formula (III$_a$)

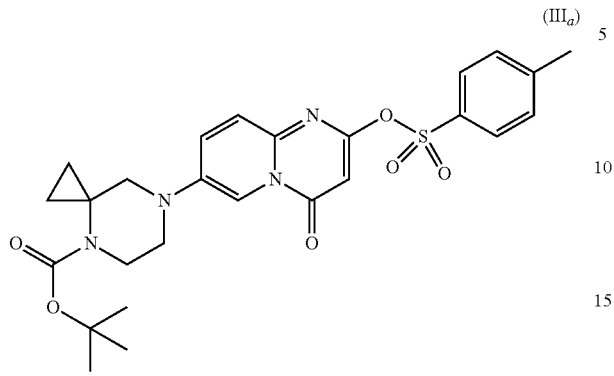

with a compound of formula (III')

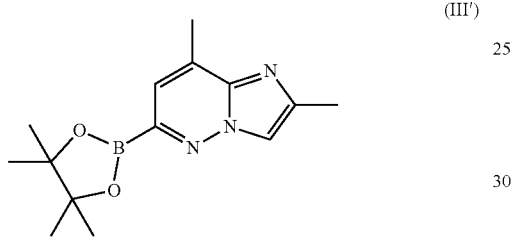

in the presence of a palladium catalyst or nickel catalyst, in particular in presence of a palladium catalyst which further comprises a base, particularly wherein the base is Na$_2$CO$_3$, K$_2$CO$_3$, Cs$_2$CO$_3$, KOAc or KOtBu more particularly wherein the base is K$_2$CO$_3$.

The present application discloses a process for the preparation of a compound of formula (II)

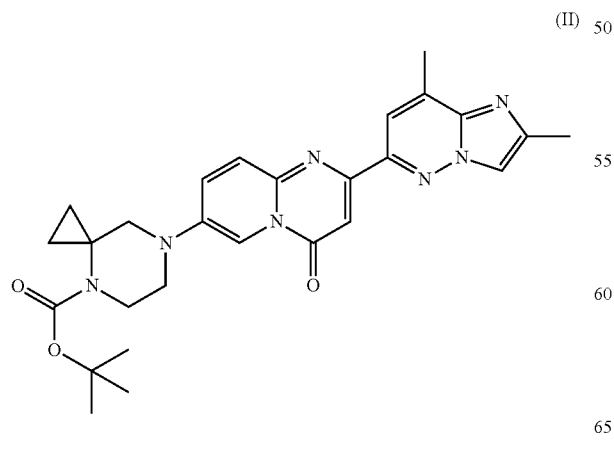

which comprises
a) reacting a compound of formula (III")

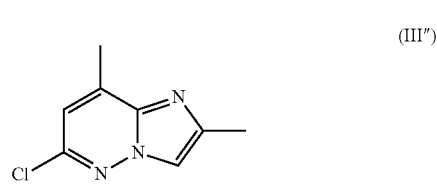

with bis(pinacolato)diboron to obtain a compound of formula (III'):

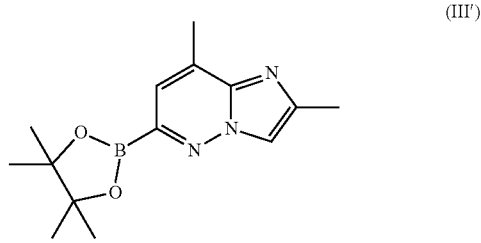

b) reacting a compound of formula (III)

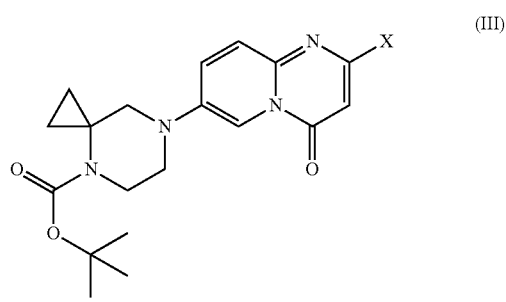

wherein X is an alkyl or aryl sulfonate (such as pTolSO$_3$-, CH$_3$SO$_3$—, phenyl-SO$_3$—), fluorinated alkyl or aryl sulfonates (such as CF$_3$SO$_3$—, nonaflate), or a halide (such as Cl, Br, or I) with a compound of formula (III'), (III$_a$') or (III$_b$'), in particular with a compound of formula (III'),

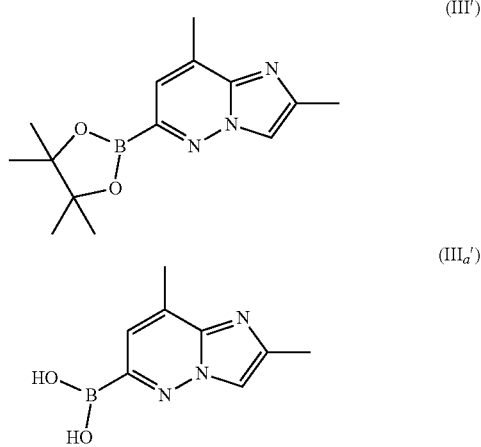

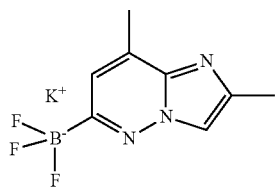

in the presence of a palladium catalyst or nickel catalyst, in particular in presence of a palladium catalyst, to obtain a compound of formula (II).

The present application discloses a process for the preparation of a compound of formula (II)

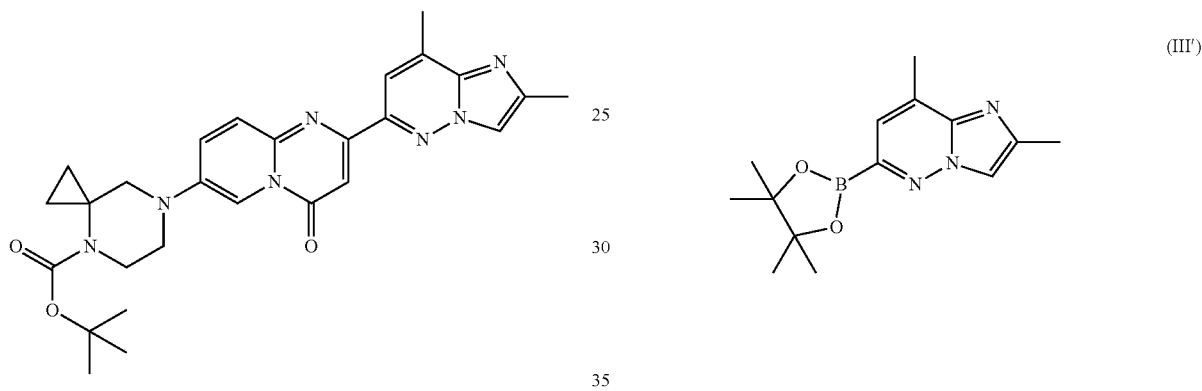

which comprises
a) reacting a compound of formula (III")

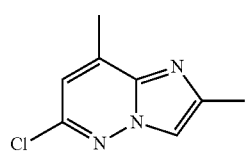

with bis(pinacolato)diboron to obtain a compound of formula (III'):

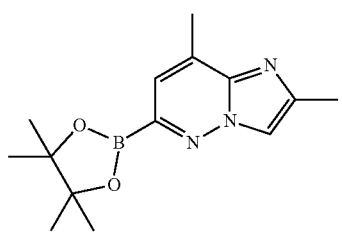

b) reacting a compound of formula (III$_a$)

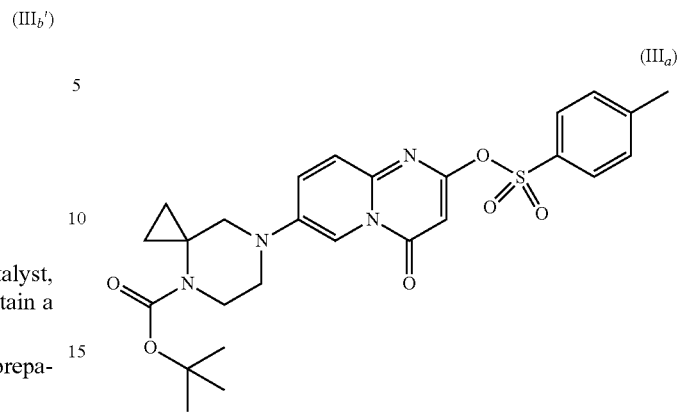

with a compound of formula (III')

in the presence of a palladium catalyst or nickel catalyst, in particular in presence of a palladium catalyst, to obtain a compound of formula (II), wherein the reaction of compound of formulae (III) or (III$_a$) with compound of formulae (III'), (III$_a$') or (III$_b$'), in particular with a compound of formula (III') in the presence of palladium catalyst or nickel catalyst, in particular in presence of a palladium catalyst as defined herein, is carried out in presence of a base, particularly wherein the base is Na$_2$CO$_3$, K$_2$CO$_3$, Cs$_2$CO$_3$, KOAc or KOtBu more particularly wherein the base is K$_2$CO$_3$.

The present application discloses a process for the preparation of a compound of formula (III)

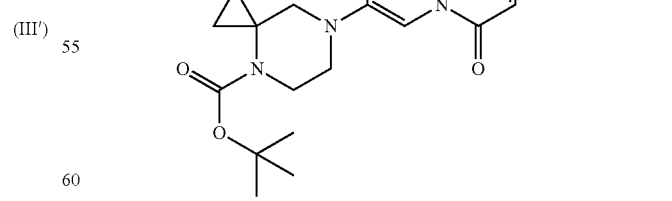

wherein X is an alkyl or aryl sulfonate (such as pTolSO$_3$-, CH$_3$SO$_3$—, phenyl-SO$_3$—), fluorinated alkyl or aryl sulfonates (such as CF$_3$SO$_3$—, nonaflate), or a halide (such as Cl, Br, or I), which comprises reacting a compound of formula (IV)

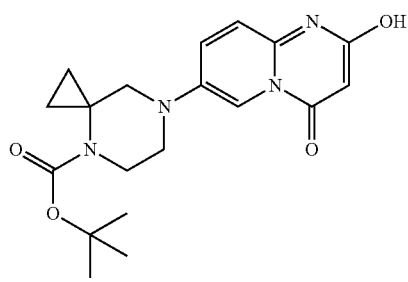

(IV)

with tosyl chloride when X is pTol-SO₃—, methanesulfonyl chloride when X is CH₃SO₃—, triflyl chloride when X is CF₃SO₃— or phenylsulfonylchloride when X is phenyl-SO₃—, and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine;
with POCl₃ when X is Cl;
with POBr₃ when X is Br; or
with, Ph₃PI₂ or POCl₃ followed by NaI or CuI, when X is I.

The present application discloses a process for the preparation of a compound of formula (III$_a$)

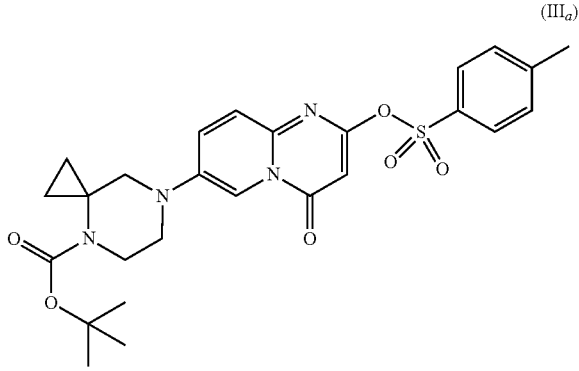 [SMILES: Cc1ccc(S(=O)(=O)Oc2cc(=O)n3cc(N4CCN(C(=O)OC(C)(C)C)C5(CC5)C4)ccc3n2)cc1]

(III$_a$)

which comprises reacting a compound of formula (IV)

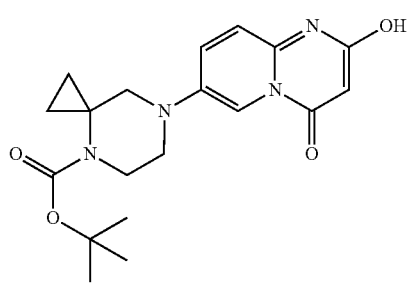

(IV)

with tosyl chloride and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine.

The present application discloses a process for the preparation of a compound of formula (IV)

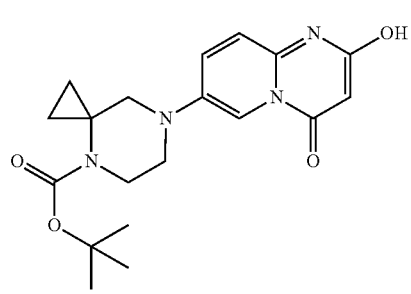

(IV)

which comprises reacting a compound of formula (V)

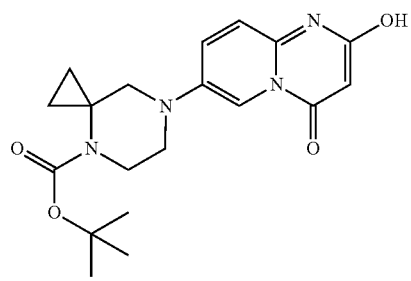

(V)

with di-tert-butyl malonate.

The present application discloses a process for the preparation of a compound of formula (IV)

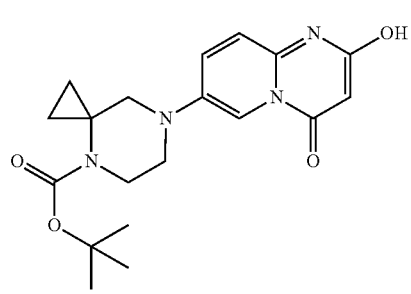

(IV)

which comprises:
a) reduction of a compound of formula (VI)

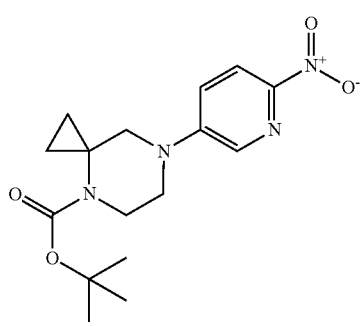

(VI)

to a compound of formula (V)

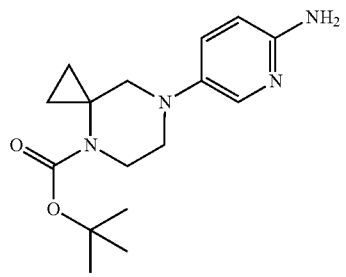

b) reacting a compound of formula (V) with di-tert-butyl malonate to obtain a compound of formula (IV).

The present application discloses a process for the preparation of a compound of formula (IV)

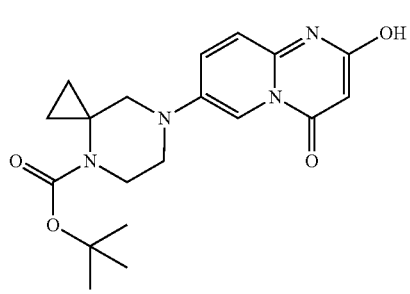

which comprises:
a) reacting a compound of formula (VI)

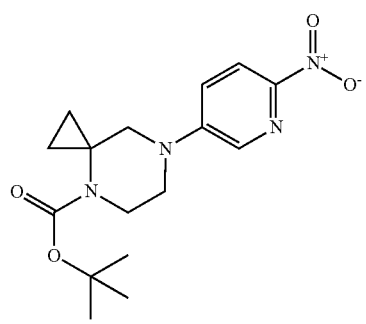

with a transition metal hydrogenation catalyst to obtain a compound of formula (V)

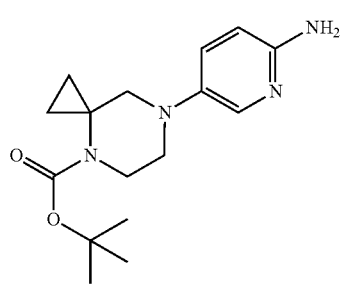

b) reacting a compound of formula (V) with di-tert-butyl malonate to obtain a compound of formula (IV).

In particular, the process for the preparation of a compound of formula (IV) which comprises reacting a compound of formula (V) with di-tert-butyl malonate, is carried out in the presence of xylene, dichlorobenzene, toluene or anisole, in particular in the presence of anisole.

In more particular, the preparation of compound of formula (IV), wherein the transition metal hydrogenation catalyst is Raney catalyst (e.g., Ra—Ni, Ra—Co) Pd/C, Pd(OH)$_2$/C, Au/TiO$_2$, Rh/C, Ru/Al$_2$O$_3$, Ir/CaCO$_3$, Pt—V/C or Pt/C or combination thereof, in particular Pt—V/C, more particularly Pt 1% and V 2% on activated carbon.

The present application discloses the preparation of a compound of formula (VI)

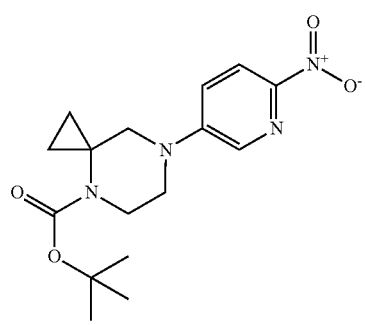

which comprises reacting a compound of formula (VII)

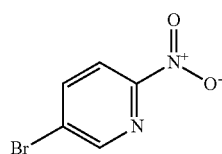

with a compound of formula (VIII)

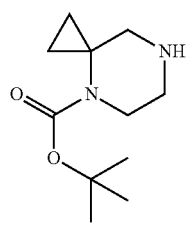

or a salt thereof (in particular the oxalate salt), more particularly wherein salt of the compound of formula (III) is tert-butyl 4,7-diazaspiro[2.5]octane-4-carboxylate oxalate salt.

In particular, the process for the preparation of a compound of formula (VI) which comprises reacting a compound of formula (VII) with a compound of formula (VIII), in the presence of lithium chloride, dimethyl sulfoxide and a base such as tetramethylguanidine, triethylamine, diisopropylethylamine or 1,8-diazabicyclo[5.4.0]undec-7-ene (DBU), most particular with tetramethylguanidine.

In a further embodiment the present application discloses the preparation of a compound of formula (V) in accordance to scheme 1.

23

Scheme 1

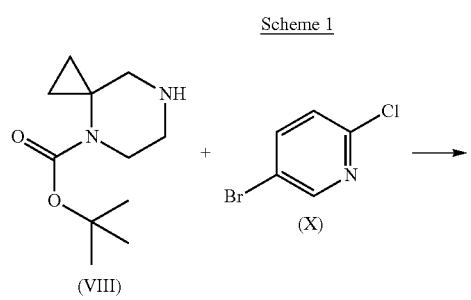

(VIII)     (X)

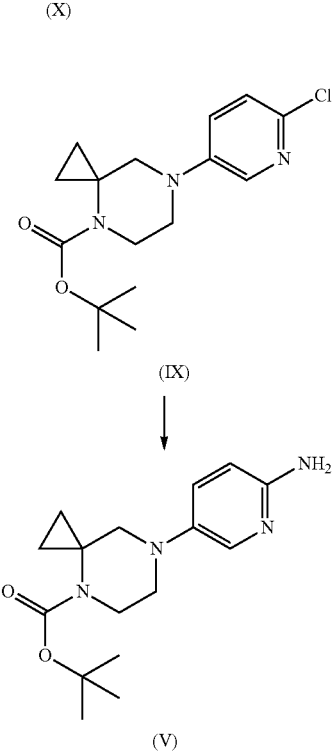

(IX)

↓

(V)

In particular, compound of formula (IX) can be prepared by reacting a compound of formula (X) with a compound of formula (VIII), in the presence of a catalyst (such as but not limited to Pd(PPh$_3$)$_4$, PdCl$_2$, Pd(OAc)$_2$, Pd$_2$(dba)$_3$, Pd(PPh$_3$)$_2$Cl$_2$, PdCl$_2$(dppf), PdCl$_2$(dppf). CH$_2$Cl$_2$, PdCl$_2$(dppp), PdCl$_2$(CH$_3$CN), Cyclopentadienyl allyl palladium, allylpalladium(II) chloride dimer (Pd(allyl)Cl)$_2$, (2-Butenyl)chloropalladium dimer, (2-Methylallyl) palladium(II) chloride dimer, palladium(1-phenylallyl)chloride dimer, di-µ-chlorobis[2'-(amino-N)[1,1'-biphenyl]-2-yl-C]dipalladium(II), Di-µ-chlorobis[2-[(dimethylamino)methyl]phenyl-C,N]dipalladium(II), dichloro[9,9-dimethyl-4,5-bis(diphenylphosphino)xanthene]palladium (Pd(XantPhos)Cl$_2$), in particular in the presence of dichloro[9,9-dimethyl-4,5-bis(diphenylphosphino)xanthene]palladium); and a base (such as Na$_2$CO$_3$, K$_2$CO$_3$, Cs$_2$CO$_3$, KOtBu, NaOtBu ((CH$_3$)$_3$CONa) or KOAc; in particular KOtBu), in particular in 2-methyltetrahydrofurane, THF or dioxane, more particularly in 2-methyltetrahydrofurane. Compound (V) can be prepared by reacting compound (IX) with ammonia (NH$_3$) in the presence of a catalyst such as Pd(PPh$_3$)$_4$, PdCl$_2$, Pd(OAc)$_2$, Pd$_2$(dba)$_3$, Pd(PPh$_3$)$_2$Cl$_2$, PdCl$_2$(dppf), PdCl$_2$(dppf). CH$_2$Cl$_2$, PdCl$_2$(dppp), PdCl$_2$(CH$_3$CN), cyclopentadienyl allyl palladium, allylpalladium(II) chloride dimer (Pd(allyl)Cl)$_2$ (2-butenyl)chloropalladium dimer, (2-methylallyl) palladium(II) chloride dimer, palladium(1-phenylallyl)chloride dimer, di-µ-chlorobis[2'-(amino-N)[1,1'-biphenyl]-2-yl-C]dipalladium(II), Di-µ-chlorobis[2-[(dimethylamino)methyl]

24 phenyl-C,N]dipalladium(II), in particular in the presence of Pd$_2$(dba)$_3$, a base (such as Na$_2$CO$_3$, K$_2$CO$_3$, Cs$_2$CO$_3$, KOtBu, NaOtBu ((CH$_3$)$_3$CONa) or KOAc; in particular KOtBu) and t-Bu Brett Phos.

Preferably this step is carried out in dioxane.

Compound of formula (V) can be also prepared in accordance to scheme 2.

Scheme 2

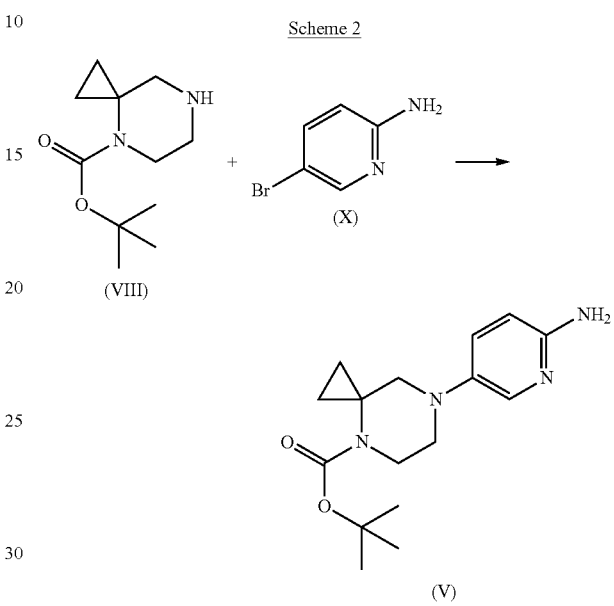

(VIII)     (X)

(V)

In particular, compound of formula (V) can be prepared by reacting a compound of formula (X) with a compound of formula (VIII), in the presence of a catalyst (such as Pd(PPh$_3$)$_4$, Pd(OAc)$_2$, Pd$_2$(dba)$_3$, PdCl$_2$, PdCl$_2$(dppf), PdCl$_2$(dppf). CH$_2$Cl$_2$, PdCl$_2$(dppp), allylpalladium(II) chloride dimer (Pd(allyl)Cl)$_2$ (2-butenyl) chloropalladium dimer, (2-methylallyl)palladium(II) chloride dimer, palladium(1-phenylallyl)chloride dimer, di-µ-chlorobis[2'-(amino-N)[1,1'-biphenyl]-2-yl-C]dipalladium(II), di-µ-chlorobis[2-[(dimethylamino)methyl]phenyl-C,N]dipalladium(II), in particular in the presence of allylpalladium(II) chloride dimer (Pd(allyl)Cl)$_2$ or palladium(1-phenylallyl)chloride dimer; and a ligand (such as 2-dicyclohexylphosphino-2'-(N,N-dimethylamino)biphenyl (DavePhos) or 2-di-tert-butylphosphino-2'-(N,N-dimethylamino)biphenyl (tBuDavePhos), in particular: tBuDavePhos) and a base (such as Na$_2$CO$_3$, K$_2$CO$_3$, Cs$_2$CO$_3$, KOtBu, NaOtBu ((CH$_3$)$_3$CONa), KOAc or lithium-bis(trimethylsilyl)amid; in particular lithium-bis(trimethylsilyl)amid), in particular in tetrahydrofuran.

The present invention takes place in the presence of an organic solvent such as an ether like solvent (e.g., tetrahydrofuran, diisopropyl ether, t-butylmethyl ether, cyclopentyl-methyl-ether or dibutyl ether), chlorinated solvents (e.g., dichloromethane, chloroform) or aromatic solvent (e.g., anisole, toluene or t-butyl-benzene). In particular, the solvent to be used for the preparation of a compound of formula (I) according to aspect 1 is toluene.

The reactions are performed in particular under an inert gas atmosphere, more particularly under argon or nitrogen.

The present application discloses a process for the preparation of a compound of formula (III") in accordance with scheme 3:

Scheme 3

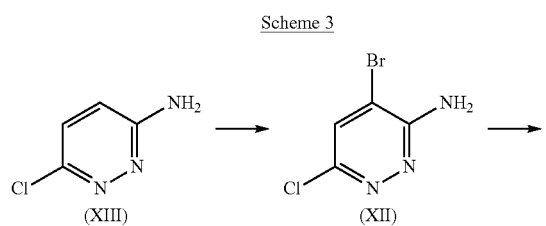

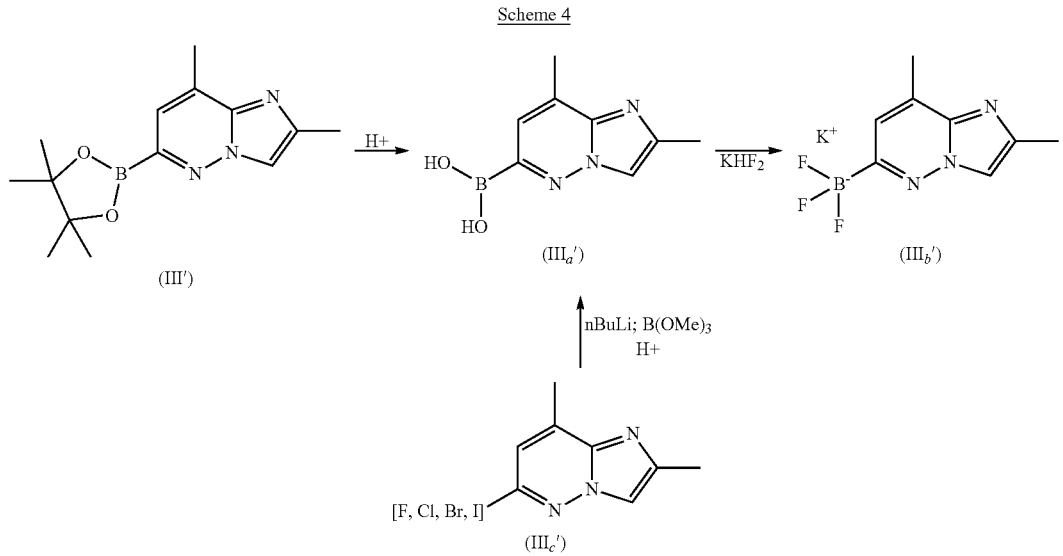

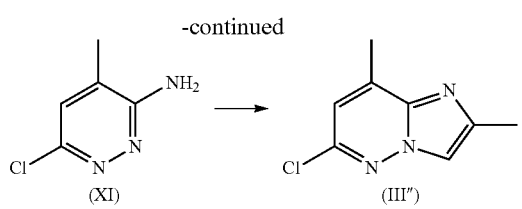

In particular, according to application, a compound of formula (XII) is prepared by reacting a compound of formula (XIII) with 1,3-dibromo-5,5-dimethylhydantoin (DBDMH), N-bromo-succinimide or bromine, optionally with sodium acetate or sodium bicarbonate and in the presence of a solvent such as alcohols (e.g., methanol or ethanol). Furthermore a compound of (XI) is prepared by reacting a compound of formula (XII) with methyl magnesium chloride or bromide, methylboronic acid, methyl borate, dimethylzinc or methyllithium, optionally in the presence of zinc chloride or with dimethylzinc in methyltetrahydrofuran or THF, in the presence of a catalyst (such as $Pd(PPh_3)_4$, $PdCl_2$, $Pd(OAc)_2$, $Pd_2(dba)_3$, $Pd(PPh_3)_2Cl_2$, $PdCl_2(dppf)$, $PdCl_2(dppf) \cdot CH_2Cl_2$, $PdCl_2(dppp)$, cyclopentadienyl allyl palladium, allylpalladium(II) chloride dimer $(Pd(allyl)Cl)_2$ (2-Butenyl)chloropalladium dimer, (2-Methylallyl) palladium(II) chloride dimer, palladium(1-phenylallyl)chloride dimer, di-µ-chlorobis[2'-(amino-N)[1,1'-biphenyl]-2-yl-C]dipalladium(II), di-µ-chlorobis[2-[(dimethylamino)methyl]phenyl-C,N]dipalladium(II), dichloro[9,9-dimethyl-4,5-bis(diphenylphosphino)xanthene]palladium $(Pd(XantPhos)Cl_2)$, in particular in the presence $Pd(PPh_3)_4$). A compound of formula (III") is prepared by reacting chloroacteone with a compound of formula (XI) in the presence of tertiary amine and sodium bromide.

Alternatively compound of formula (III") can be prepared in accordance with the process described in WO2015173181.

The present application further discloses a process for the preparation of compound of formula ($III_a'$) or ($III_b'$) in accordance with scheme 4.

A particular embodiment of the invention also relates to a pharmaceutical composition comprising the compound of formula (I) obtained according to as described herein and at least one pharmaceutically acceptable excipient.

A further particular embodiment of the invention also relates to a compound of formula (I) obtained by the process as described herein for use as therapeutically active substances.

Process for Manufacturing Form A:

Form A of 7-(4,7-diazaspiro[2.5]octan-7-yl)-2-(2,8-dimethylimidazo[1,2-b]pyridazin-6-yl)pyrido[1,2-a]pyrimidin-4-one can be obtained by dissolving 7-(4,7-diazaspiro[2.5]octan-7-yl)-2-(2,8-dimethylimidazo[1,2-b]pyridazin-6-yl)pyrido[1,2-a]pyrimidin-4-one in dioxane at elevated temperature (e.g., above 22° C.), in particular at 80° C. Upon cooling 7-(4,7-diazaspiro[2.5]octan-7-yl)-2-(2,8-dimethylimidazo[1,2-b]pyridazin-6-yl)pyrido[1,2-a]pyrimidin-4-one crystallized spontaneously as Form A.

Alternatively, Form A can be obtained upon equilibration of solid 7-(4,7-diazaspiro[2.5]octan-7-yl)-2-(2,8-dimethylimidazo[1,2-b]pyridazin-6-yl)pyrido[1,2-a]pyrimidin-4-one suspended in organic solvents or a mixture thereof for prolonged time. In particular 7-(4,7-diazaspiro[2.5]octan-7-yl)-2-(2,8-dimethylimidazo[1,2-b]pyridazin-6-yl)pyrido[1,2-a]pyrimidin-4-one can be suspended in ethanol, methyl ethyl ketone, ethyl acetate, or dioxane at ambient temperature or at elevated temperature (e.g. 22 to 65° C.) for 2-3 weeks affording 7-(4,7-diazaspiro[2.5]octan-7-yl)-2-(2,8-dimethylimidazo[1,2-b]pyridazin-6-yl)pyrido[1,2-a]pyrimidin-4-one as Form A.

To obtain Form A, 7-(4,7-diazaspiro[2.5]octan-7-yl)-2-(2,8-dimethylimidazo[1,2-b]pyridazin-6-yl)pyrido[1,2-a]pyrimidin-4-one is dissolved in water with hydrochloric acid as the corresponding hydrochloric acid salt. This solution is added slowly to a solution of sodium hydroxide (molar excess of sodium hydroxide with respect to applied hydrochloric acid) in ethanol at elevated temperature (e.g., above 22° C.), in particular at 60-70° C., more particular at 60° C. A suspension is formed upon spontaneous crystallization comprising a saturated solution and a crystalline solid of Form A. The suspension is cooled, filtered, and washed to remove sodium chloride and dried under vacuum at elevated temperature (e.g., above 22° C., in particular at 60° C.). In order to control the solid Form A the final conditions in suspension must be controlled by controlling the maximum water concentration and a minimum temperature.

Alternatively, Form A can be further obtained upon crystallization with application crystals of Form A being used as seeding crystals. 7-(4,7-diazaspiro[2.5]octan-7-yl)-2-(2,8-dimethylimidazo[1,2-b]pyridazin-6-yl)pyrido[1,2-a]pyrimidin-4-one can be dissolved in water with hydrochloric acid as the corresponding hydrochloric acid salt. Part of this solution is added to a solution of sodium hydroxide (molar excess of sodium hydroxide with respect to applied hydrochloric acid) in ethanol at elevated temperature (between 20 to 70° C., particularly at 60° C.), Crystals of Form A are added to the thus formed solution (either as dry crystals or suspended in organic solvent, e.g., ethanol). A suspension is formed. The remaining hydrochloric acid salt solution is added slowly at elevated temperature. The suspension is cooled, filtered, and washed to remove sodium chloride and dried under vacuum at elevated temperature (e.g., above 22° C., in particular at 60° C.). In order to control the solid Form A the final conditions in suspension must be controlled by controlling the maximum water concentration and a minimum temperature (e.g., not more than 12%-wt of water in ethanol at more than 40° C.).

Process for Preparation of Form D:

Form D can be obtained by equilibration of solid 7-(4,7-diazaspiro[2.5]octan-7-yl)-2-(2,8-dimethylimidazo[1,2-b]pyridazin-6-yl)pyrido[1,2-a]pyrimidin-4-one suspended in water or water containing organic solvents for prolonged time. 7-(4,7-diazaspiro[2.5]octan-7-yl)-2-(2,8-dimethylimidazo[1,2-b]pyridazin-6-yl)pyrido[1,2-a]pyrimidin-4-one can be suspended in water or mixtures of organic solvent and water, in particular in ethanol/water mixtures. In particular, the mixture can be left in equilibration for 2-3 weeks in water or in ethanol/water 20/80 v/v at 65° C. to afford 7-(4,7-diazaspiro[2.5]octan-7-yl)-2-(2,8-dimethylimidazo[1,2-b]pyridazin-6-yl)pyrido[1,2-a]pyrimidin-4-one as Form D. In particular, the mixture can be left in equilibration for 2-3 weeks in water or in ethanol/water 20/80 v/v to 50/50 v/v to 80/20 v/v at approx. 22° C. to afford 7-(4,7-diazaspiro[2.5]octan-7-yl)-2-(2,8-dimethylimidazo[1,2-b]pyridazin-6-yl)pyrido[1,2-a]pyrimidin-4-one as Form D.

A certain embodiment of the invention relates to the crystalline Form A of the compound of formula I as described herein, characterized by the X-ray powder diffraction pattern as shown in FIG. 1.

A certain embodiment of the invention relates to the crystalline Form A of the compound of formula I as described herein, characterized by the Raman spectrum shown in as shown in FIG. 2.

A certain embodiment of the invention relates to the crystalline Form A of the compound of formula I as described herein, characterized by the Infrared spectrum shown in as shown in FIG. 3.

The starting materials and reagents, which do not have their synthetic route explicitly disclosed herein, are generally available from commercial sources or are readily prepared using methods well known to the person skilled in the art.

7-(4,7-diazaspiro[2.5]octan-7-yl)-2-(2,8-dimethylimidazo[1,2-b]pyridazin-6-yl)pyrido[1,2-a]pyrimidin-4-one was found to crystallize in different crystal structures as pure compound (polymorphs). Of these, Form A is the thermodynamic stable polymorph, in particular between 5° C. to 65° C.

In another aspect, 7-(4,7-diazaspiro[2.5]octan-7-yl)-2-(2,8-dimethylimidazo[1,2-b]pyridazin-6-yl)pyrido[1,2-a]pyrimidin-4-one was found to crystallize in different crystal structures as hydrated compound. With sufficiently high water activity, Form D is the stable hydrated form.

In another embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in crystalline Form A or Form D.

In a particular embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in polymorphic Form A characterized by an X-ray powder diffraction pattern (XRPD) having peaks at an angle of diffraction 2-theta at about 12.7°, 15.9°, 24.0°, and 25.6° (±0.2°).

In particular embodiment, Form A is characterized by XRPD diffraction pattern of comprising XRPD peaks at angles of diffraction 2-theta of as denoted in Table 2.

In a particular embodiment, Form A is characterized by the XRPD of FIG. 1.

Table 1 lists the relevant crystal structure data of Form A. The lattice constants, unit cell volume and calculated density are based at ambient temperature data.

TABLE 1

Single Crystal Structural Data of Form A

| Crystal form | | Form A |
|---|---|---|
| Measuring Temperature | | 293(2) K |
| Crystal system | | monoclinic |
| Space group | | P2$_1$/c (No 14) |
| Unit cell dimensions: | a | 21.565(4) Å |
| | b | 5.9670(12) Å |
| | c | 15.717(3) Å |
| | α | 90° |
| | β | 98.87(3)° |
| | γ | 90° |
| Cell volume | | 1998.2(7) Å$^3$ |
| API molecules in unit cell | | 4 |
| Calculated density | | 1.335 g/cm$^3$ |

TABLE 2

XRPD of Form A:
Form A

| Degrees 2 Theta | rel. int./% * |
|---|---|
| 8.3 | 29 |
| 11.4 | 81 |
| 12.7 | 99 |
| 13.0 | 35 |
| 15.1 | 37 |
| 15.4 | 11 |
| 15.9 | 87 |
| 16.7 | 13 |
| 17.0 | 47 |

TABLE 2-continued

XRPD of Form A:
Form A

| Degrees 2 Theta | rel. int./% * |
|---|---|
| 17.5 | 18 |
| 18.7 | 18 |
| 19.4 | 16 |
| 19.7 | 43 |
| 19.8 | 12 |
| 21.3 | 10 |
| 22.4 | 55 |
| 23.6 | 13 |
| 24.0 | 94 |
| 24.7 | 10 |
| 25.6 | 100 |
| 26.7 | 20 |
| 26.8 | 27 |
| 27.4 | 12 |
| 29.3 | 13 |
| 30.7 | 11 |

* Relative intensities may vary considerably from one measurement to another

In a particular embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in polymorphic Form A characterized by infrared (IR) spectrum comprising at least one peak at one of the positions 848 (±2) cm$^{-1}$, 885 (±2) cm$^{-1}$, 939 (±2) cm$^{-1}$, or 1218 (±2) cm$^{-1}$, particularly comprising at least two peaks at positions 848 (±2) cm$^{-1}$, 885 (±2) cm$^{-1}$, 939 (±2) cm$^{-1}$, or 1218 (±2) cm$^{-1}$, more particularly comprising at least three peaks at positions 848 (±2) cm 885 (±2) cm$^{-1}$. 939 (±2) cm$^{-1}$, or 1218 (±2) cm$^{-1}$, most particularly having four peaks at positions 848 (±2) cm$^{-1}$, 885 (±2) cm$^{-1}$, 939 (±2) cm$^{-1}$, and 1218 (±2) cm$^{-1}$.

In a further embodiment, Form A is characterized by IR spectrum comprising IR peaks at positions as denoted in Table 3.

TABLE 3

Infrared peak positions for Form A. The peak positions are stated in cm$^{-1}$ and the error is ±2 cm$^{-1}$.

| |
|---|
| 651 |
| 674 |
| 702 |
| 715 |
| 729 |
| 745 |
| 762 |
| 768 |
| 834 |
| 848 |
| 864 |
| 874 |
| 885 |
| 907 |
| 926 |
| 939 |
| 984 |
| 1014 |
| 1050 |
| 1060 |
| 1078 |
| 1133 |
| 1144 |
| 1161 |
| 1187 |
| 1218 |
| 1228 |
| 1258 |
| 1327 |
| 1358 |
| 1386 |
| 1399 |
| 1445 |
| 1476 |
| 1528 |
| 1553 |
| 1629 |
| 1666 |
| 2823 |
| 2922 |
| 3035 |
| 3062 |
| 3244 |

According to the invention herein described, the ATR FTIR spectra were recorded without any sample preparation using a ThermoNicolet iS5 FTIR spectrometer with an iD5 ATR accessory and DTGS detector. The spectral range is between 4000 cm$^{-1}$ and 650 cm$^{-1}$, resolution 2 cm$^{-1}$ and at least 50 co-added scans were collected. Happ-Genzel apodization was applied.

In a particular embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in polymorphic Form A characterized by Raman spectrum comprising at least one peak at one of the positions 213 (±2) cm$^{-1}$, 257 (±2) cm$^{-1}$, 1061 (±2) cm$^{-1}$, or 1570 (±2) cm$^{-1}$, particularly comprising at least two peaks at positions 213 (±2) cm$^{-1}$, 257 (±2) cm$^{-1}$, 1061 (±2) cm$^{-1}$, or 1570 (±2) cm$^{-1}$, more particularly comprising at least two peaks at positions 213 (±2) cm$^{-1}$, 257 (±2) cm$^{-1}$, 1061 (±2) cm$^{-1}$, or 1570 (±2) cm$^{-1}$, even more particularly comprising at least three peaks at positions 213 (±2) cm$^{-1}$, 257 (±2) cm$^{-1}$, 1061 (±2) cm$^{-1}$, or 1570 (±2) cm$^{-1}$, most particularly having four peaks at positions 213 (±2) cm$^{-1}$ 257 (±2) cm$^{-1}$, 1061 (±2) cm$^{-1}$, or 1570 (±2) cm$_{-1}$.

In a further embodiment, Form A is characterized by Raman spectrum comprising Raman peaks at positions as denoted in Table 4.

TABLE 4

Raman peak positions for Form A. The peak positions are stated in cm$^{-1}$ and the error is ±2 cm$^{-1}$.

| |
|---|
| 72 |
| 142 |
| 183 |
| 213 |
| 257 |
| 321 |
| 343 |
| 379 |
| 412 |
| 459 |
| 524 |
| 548 |
| 560 |
| 581 |
| 770 |
| 865 |
| 987 |
| 1061 |
| 1149 |
| 1187 |
| 1220 |
| 1260 |
| 1305 |

TABLE 4-continued

Raman peak positions for Form A. The peak positions are stated in cm$^{-1}$ and the error is ±2 cm$^{-1}$.

1340
1409
1488
1530
1570
1633
1671
2924
3149

According to the invention herein described, the FT-Raman spectrum collected in the spectral range of 4000-50 cm$^{-1}$ with a Bruker MultiRam FT-Raman spectrometer, equipped with a NdYAG 1064 nm laser and a liquid nitrogen cooled Germanium detector. The laser power at the sample was about 200 mW, 2 cm$^{-1}$ resolution was used and 1024 or 2048 scans were co-added. The apodization used was Blackman-Harris 4-term.

In a particular embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in hydrate Form D characterized by an XRPD having peaks at an angle of diffraction at about 8.4 (±0.2) degrees two-theta, 23.5 (±0.2) degrees two-theta, 24.4 (±0.2) degrees two-theta, and 25.3 (±0.2) degrees two-theta.

In particular embodiment, Form D is characterized by XRPD diffraction pattern of comprising XRPD peaks at angles of diffraction 2-Theta of as denoted in Table 5.

In a particular embodiment, Form D is characterized by the XRPD diffraction pattern of FIG. 4.

TABLE 5

XRPD of Form D:
Form D

| degrees 2-theta/° | rel. int./% * |
|---|---|
| 5.4 | 17 |
| 8.4 | 66 |
| 10.4 | 14 |
| 10.9 | 7 |
| 12.8 | 33 |
| 13.1 | 14 |
| 13.9 | 28 |
| 17.6 | 13 |
| 18.2 | 12 |
| 18.8 | 9 |
| 19.3 | 19 |
| 19.9 | 36 |
| 20.8 | 29 |
| 22.0 | 32 |
| 22.6 | 34 |
| 23.5 | 90 |
| 24.4 | 100 |
| 24.7 | 8 |
| 25.3 | 82 |
| 26.1 | 30 |
| 27.2 | 41 |
| 27.7 | 16 |
| 27.9 | 8 |
| 28.5 | 20 |
| 28.7 | 6 |
| 29.2 | 10 |
| 29.4 | 20 |
| 30.7 | 17 |
| 31.3 | 12 |

* Relative intensities may vary considerably from one measurement to another

In a particular embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in hydrate Form D characterized by infrared (IR) spectrum comprising at least one peak at one of the positions 800 (±2) cm$^{-1}$, 1212 (±2) cm$^{-1}$, 1349 (±2) cm$^{-1}$, or 1577 (±2) cm$^{-1}$, particularly comprising at least two peaks at positions 800 (±2) cm$^{-1}$, 1212 (±2) cm$^{-1}$, 1349 (±2) cm$^{-1}$, or 1577 (±2) cm$^{-1}$, more particularly comprising at least two peaks at positions 800 (±2) cm$^{-1}$, 1212 (±2) cm$^{-1}$, 1349 (±2) m$^{-1}$, or 1577 (±2) cm$^{-1}$, even more particularly comprising at least three peaks at positions 800 (±2) cm$^{-1}$, 1212 (±2) cm$^{-1}$, 1349 (±2) cm$^{-1}$, or 1577 (±2) cm$^{-1}$, most particularly having four peaks at positions 800 (±2) cm$^{-1}$, 1212 (±2) cm$^{-1}$, 1349 (±2) cm$^{-1}$, or 1577 (±2) cm$^{-1}$.

In a further embodiment, Form D is characterized by IR spectrum comprising IR peaks at positions as denoted in Table 6.

TABLE 6

Infrared peak positions for Form D. The peak positions are stated in cm$^{-1}$ and the error is ±2 cm$^{-1}$.

650
695
710
718
733
752
776
800
820
837
869
903
925
949
990
1003
1021
1031
1055
1074
1122
1147
1165
1187
1212
1228
1261
1281
1321
1330
1349
1371
1391
1409
1427
1463
1479
1488
1529
1555
1577
1630
1660
2913
2972
3137
3268
3435

In a particular embodiment, the present invention provides 7-(4,7-diazaspiro[2.5]octan-7-yl)-2-(2,8-dimethylimidazo[1,2-b]pyridazin-6-yl)pyrido[1,2-a]pyrimidin-4-one in hydrate Form D characterized by Raman spectrum comprising at least one peak at one of the positions 452 (±2 cm$^{-1}$) 870 (±2 cm$^{-1}$), 1311 (±2 cm$^{-1}$), or 1578 (±2 cm$^{-1}$), particularly comprising at least two peaks at positions 152 (±2 cm$^{-1}$), 870 (±2 cm$^{-1}$), 1311 (±2 cm$^{-1}$), or 1578 (±2 cm$^{-1}$), more particularly comprising at least two peaks at positions 452 (±2 cm$^{-1}$), 870 (±2 cm$^{-1}$), 1311 (±2 cm$^{-1}$) or 1578 (±2 cm$^{-1}$), even more particularly comprising at least three peaks at positions 452 (±2 cm$^{-1}$), 8710 (±2 cm$^{-1}$), 1311 (±2 cm$^{-1}$), or 1578 (±2 cm$^{-1}$), most particularly having four peaks at positions 452 (±2 cm$^{-1}$), 870 (±2 cm$^{-1}$), 1311 (±2 cm$^{-1}$), or 1578 (±2 cm$^{-1}$).

In a further embodiment, Form D is characterized by Raman spectrum comprising Raman peaks at positions as denoted in Table 7,

TABLE 7

Raman peak positions for Form D. The peak positions are stated in cm$^{-1}$ and the error is ±2 cm$^{-1}$.

| |
|---|
| 59 |
| 160 |
| 224 |
| 269 |
| 383 |
| 452 |
| 480 |
| 496 |
| 519 |
| 552 |
| 593 |
| 719 |
| 735 |
| 768 |
| 824 |
| 870 |
| 928 |
| 986 |
| 1056 |
| 1081 |
| 1123 |
| 1142 |
| 1171 |
| 1187 |
| 1263 |
| 1311 |
| 1332 |
| 1342 |
| 1489 |
| 1532 |
| 1561 |
| 1578 |
| 1635 |
| 1661 |
| 2925 |
| 3005 |
| 3086 |

In another embodiment the present invention relates to a pharmaceutical composition comprising compound of formula (I), in particular 7-(4,7-diazaspiro[2.5]octan-7-yl)-2-(2,8-dimethylimidazo[1,2-b]pyridazin-6-yl)pyrido[1,2-a]pyrimidin-4-one or pharmaceutically acceptable salts thereof, in more particular comprising 7-(4,7-diazaspiro[2.5]octan-7-yl)-2-(2,8-dimethylimidazo[1,2-b]pyridazin-6-yl)pyrido[1,2-a]pyrimidin-4-one Form A; wherein the composition is an oral aqueous solution or a dry powder suitable for constitution of an oral aqueous solution.

The compounds of formula (I) can be formulated as oral aqueous solution by dissolving the drug substance in a buffer system at pH of less than pH 4, particularly less than pH 3.8, more particularly less than pH 3.6, most particularly between pH 3.0 and pH 3.2, in order to provide sufficiently high drug concentration, e.g., citric buffer system, malate buffer system, maleate buffer system, or tartrate buffer system, most particularly tartrate buffer system.

It was found that having a low pH helps improve the efficacy of the preservative of the formulation, and thereby to minimize its concentration according to the invention herein. This refers to the formulation once reconstituted as an aqueous solution.

Long-term stability of formulations of the compounds of formula (I) can be achieved by preparing a dry powder or granulation for constitution of an oral solution. A buffer system can be incorporated into dry formulation by the selection of organic acid and salts thereof as fine powders, e.g., tribasic sodium citrate and citric acid, disodium malate and malic acid, potassium sodium tartrate, and tartaric acid, or disodium tartrate and tartaric acid, particularly potassium sodium tartrate and tartaric acid. Alternatively, the organic acid (particularly tartaric acid) can be employed alone as acidifier instead of the combination of acid and the corresponding salt.

Powders or granules comprising a compound of formula (I) may comprise a diluent, such as sorbitol, isomalt, or particularly mannitol, and combinations thereof, which ensure fast dissolution of the powder blend during constitution of the oral solution. In introduction of a filler the powder blend can be granulated by dry compaction in order to improve the flowability and to ensure robust uniformity.

Ingredients for the constitution of a solvent system for the compounds of formula (I) can be formulated as separate formulation. The constituted solvent can be used for dissolution of the compounds of formula (I) in a bottle at the start of the in-use period of the oral solution.

A particular embodiment of the invention relates to a pharmaceutical composition comprising a compound of formula (I) or a pharmaceutically acceptable salt thereof in powder form for constitution of an oral solution.

In a particular embodiment of the invention, the pharmaceutical composition comprising a compound of formula (I) or a pharmaceutically acceptable salt thereof are filled in a multidose bottle with adapter for use of oral dispensers. It has been found that such multidose bottle with adapter for use of oral dispensers enables high dosing flexibility, e.g., body weight adjusted dosing and provides safe and convenient dose administration.

In a particular embodiment of the invention, the pharmaceutical composition comprising a compound of formula (I) or a pharmaceutically acceptable salt thereof is prepared through dry granulation by roller compaction followed bottle filling. It has been found that such processing is beneficial (particularly for water soluble fillers) to prevent demixing.

A particular embodiment of the invention relates to a pharmaceutical composition comprising a compound of formula (I) or a pharmaceutically acceptable salt thereof wherein the composition is an oral aqueous solution or a dry powder suitable for constitution of an oral aqueous solution.

A particular embodiment of the invention relates to a pharmaceutical composition comprising a compound of formula (I) or a pharmaceutically acceptable salt thereof wherein the composition is an oral aqueous solution not including aerosols or a dry powder suitable for constitution of an oral aqueous solution.

In a particular embodiment of the invention, the pharmaceutical composition comprising a compound of formula (I) or a pharmaceutically acceptable salt thereof is not an aerosol.

In a particular embodiment of the invention, the pharmaceutical composition comprising a compound of formula (I) or a pharmaceutically acceptable salt thereof does not comprise a tonicifier, e.g., a salt such as sodium chloride.

A particular embodiment of the invention relates to a pharmaceutical composition comprising a compound of formula (I) or a pharmaceutically acceptable salt thereof wherein the composition is an oral aqueous solution or a dry powder suitable for constitution of an oral aqueous solution, and wherein the oral aqueous solution has a pH of less than pH4, particularly less than pH3.8, more particularly less than pH 3.6, most particularly between pH 3.0 and pH 3.2.

A particular embodiment of the invention relates to a pharmaceutical composition comprising a compound of formula (I) or a pharmaceutically acceptable salt thereof and a citrate, malate, maleate, or tartrate buffer system, particularly a malate or tartrate buffer system, most particularly a tartrate buffer system; or alternatively the corresponding acid of a buffer system alone as acidifier, particularly tartaric acid; wherein the composition is an oral aqueous solution or a dry powder suitable for constitution of an oral aqueous solution.

A particular embodiment of the invention relates to a pharmaceutical composition comprising a compound of formula (I) or a pharmaceutically acceptable salt thereof wherein the composition is an oral aqueous solution.

A particular embodiment of the invention relates to a pharmaceutical composition comprising a compound of formula (I) or a pharmaceutically acceptable salt thereof wherein the composition is an oral aqueous solution in a buffer system at pH of less than pH4, particularly less than pH3.8, more particularly less than pH 3.6, most particularly between pH 3.0 and pH 3.2.

A particular embodiment of the invention relates to a pharmaceutical composition comprising a compound of formula (I) or a pharmaceutically acceptable salt thereof wherein the composition is an oral aqueous solution in a citrate, malate, maleate, or tartrate buffer system, particularly in a malate or tartrate buffer system, most particularly in a tartrate buffer system; or alternatively the corresponding acid of a buffer system alone as acidifier, particularly tartaric acid.

A particular embodiment of the invention relates to a pharmaceutical composition comprising a compound of formula (I) or a pharmaceutically acceptable salt thereof wherein the composition is dry powder suitable for constitution of an oral aqueous solution.

A particular embodiment of the invention relates to a pharmaceutical composition comprising a compound of formula (I) or a pharmaceutically acceptable salt thereof wherein the composition is dry powder comprising a buffer system suitable for constitution of an oral aqueous solution at pH of less than pH4, particularly less than pH3.8, more particularly less than pH 3.6, most particularly between pH 3.0 and pH 3.2.

A particular embodiment of the invention relates to a pharmaceutical composition comprising a compound of formula (I) or a pharmaceutically acceptable salt thereof wherein the composition is dry powder comprising citrate, malate, maleate, or tartrate buffer system, particularly in a malate or tartrate buffer system, most particularly in a tartrate buffer system; or alternatively the corresponding acid of a buffer system alone as acidifier, particularly tartaric acid; suitable for constitution of an oral aqueous solution.

In one embodiment of the invention, the pharmaceutical composition comprising a compound of formula (I) or a pharmaceutically acceptable salt thereof optionally further comprises an extragranular filler, such as lactose, starch, hydrolyzed starch, maltodextrin, microcrystalline cellulose, mannitol, sorbitol, sucrose, dextrose, Xylitolibasic or combinations thereof.

In a particular embodiment of the invention, the extragranular filler is sorbitol, isomalt, mannitol, or combinations thereof, particularly mannitol, more particularly crystalline mannitol, most particularly crystalline mannitol with mean diameter of 160 μm (Pearlitol® 160 C).

In introduction of a diluent, the powder blend can be granulated by dry compaction in order to improve the flowability and to ensure robust uniformity.

In one embodiment of the invention, the pharmaceutical composition comprising a compound of formula (I) or a pharmaceutically acceptable salt thereof optionally further comprises a diluent, such as lactose, starch, hydrolyzed starch, maltodextrin, microcrystalline cellulose, mannitol, isomalt (E 953, (2ξ)-6-O-α-D-Glucopyranosyl-D-arabino-hexitol), sorbitol, sucrose, dextrose, Xylitolibasic or combinations thereof.

In one embodiment of the invention, the pharmaceutical composition comprising a compound of formula (I) or a pharmaceutically acceptable salt thereof optionally further comprises a diluent, such as lactose, starch, hydrolyzed starch, microcrystalline cellulose, mannitol, sorbitol, sucrose, dextrose, Xylitolibasic or combinations thereof.

In a particular embodiment of the invention, the diluent is mannitol, particularly D-mannitol suitable for direct compression such as Parteck® M100.

In a particular embodiment of the invention, the diluent is a mixture of mannitol and isomalt, particularly D-mannitol and (2ξ)-6-O-α-D-Glucopyranosyl-D-arabino-hexitol).

Isomalt as second diluent has been found by the inventors of present invention to improve the granule properties.

The constituted oral solution of the compounds of formula (I) in a buffer can provide in-use times of more than two weeks by the use of preservatives, stabilizers and antioxidants, such as vitamin A, vitamin C, vitamin E, vitamin E TPGS, retinyl palmitate, selenium, cysteine, methionine, citric acid, sodium citrate, methyl paraben, propyl paraben, sodium benzoate, sorbic acid, potassium sorbate, disodium edetate, butyl hydroxyl toluol, riboflavin, ascorbic acid, or combinations thereof.

The constituted oral solution of the compounds of formula (I) in a buffer can provide in-use times of more than two weeks by the use of preservatives, stabilizers and antioxidants, such as vitamin E TPGS, disodium edetate, butyl hydroxyl toluene, riboflavin, ascorbic acid, or combinations thereof.

In one embodiment of the invention, the pharmaceutical composition comprising a compound of formula (I) or a pharmaceutically acceptable salt thereof optionally further comprises a preservative, antioxidant and/or stabilizer, such as vitamin E TPGS (D-alpha tocopheryl polyethylene glycol 1000 succinate), disodium ethylenediaminetetraacetate (disodium edetate, $Na_2$ EDTA), butyl hydroxyl toluene, riboflavin, ascorbic acid, or combinations thereof. It has been found that a preservative, antioxidant and/or stabilizer can be beneficial for prolonged use time in multidose containers or to improve drug stability in solution over in-use period.

In a particular embodiment of the invention, the preservative is potassium sorbate, sorbic acid or sodium benzoate (E211), particularly sodium benzoate.

In a particular embodiment of the invention, the antioxidant is ascorbic acid ((5R)-[(1S)-1,2-dihydroxyethyl]-3,4-dihydroxyfuran-2(5H)-one).

In a particular embodiment of the invention, the stabilizer is disodium ethylenediaminetetraacetate (disodium edetate, $Na_2$ EDTA).

In one embodiment of the invention, the pharmaceutical composition comprising a compound of formula (I) or a pharmaceutically acceptable salt thereof optionally further comprises a lubricant. It has been found that a lubricant can be used as processing aid for roller compaction. Further a lubricant can be used for water soluble ingredients such as PEG to ensure acceptability of appearance.

In a particular embodiment of the invention, the lubricant is poly(ethylene glycol), particularly poly(ethylene glycol) with number average molar mass $M_n$ 6,000 (PEG 6000).

In one embodiment of the invention, the pharmaceutical composition comprising a compound of formula (I) or a pharmaceutically acceptable salt thereof optionally further comprises a sweetener and/or flavor to improve palatability.

In a particular embodiment of the invention, the flavor is strawberry flavor or vanilla flavor.

In a particular embodiment of the invention, the sweetener is sucralose (1,6-dichloro-1,6-dideoxy-β-D-fructofuranosyl-4-chloro-4-deoxy-α-D-galactopyranoside, E955) or sodium saccharin.

In a particular embodiment of the invention, the compound of formula (I) is 7-(4,7-diazaspiro[2.5]octan-7-yl)-2-(2,8-dimethylimidazo[1,2-b]pyridazin-6-yl)pyrido[1,2-a]pyrimidin-4-one.

In a particular embodiment of the invention, the pharmaceutical composition comprises:
  a compound of formula (I) or a pharmaceutically acceptable salt thereof; and
  a buffer system selected from citrate, malate, maleate, or tartrate, particularly malate or tartrate, most particularly tartrate; or alternatively the corresponding acid of a buffer system alone as acidifier, particularly tartaric acid.

In a particular embodiment of the invention, the pharmaceutical composition comprises:
  a compound of formula (I) or a pharmaceutically acceptable salt thereof;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid; and
  a diluent, particularly mannitol or a mixture of mannitol and isomalt, more particularly mannitol.

In a particular embodiment of the invention, the pharmaceutical composition comprises:
  a compound of formula (I) or a pharmaceutically acceptable salt thereof; and
  a diluent, particularly mannitol or a mixture of mannitol and isomalt, more particularly mannitol.

In a particular embodiment of the invention, the pharmaceutical composition comprises:
  a compound of formula (I) or a pharmaceutically acceptable salt thereof;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
  an antioxidant, particularly ascorbic acid; and
  a stabilizer, particularly disodium edetate.

In a particular embodiment of the invention, the pharmaceutical composition comprises:
  a compound of formula (I) or a pharmaceutically acceptable salt thereof;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
  a diluent, particularly mannitol or a mixture of mannitol and isomalt, more particularly mannitol;
  an antioxidant, particularly ascorbic acid; and
  a stabilizer, particularly disodium edetate.

In a particular embodiment of the invention, the pharmaceutical composition comprises:
  a compound of formula (I) or a pharmaceutically acceptable salt thereof;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
  a diluent, particularly mannitol or a mixture of mannitol and isomalt, more particularly mannitol;
  an antioxidant, particularly ascorbic acid;
  a stabilizer, particularly disodium edetate; and
  a lubricant, particularly PEG6000.

In a particular embodiment of the invention, the pharmaceutical composition comprises:
  a compound of formula (I) or a pharmaceutically acceptable salt thereof;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
  a diluent, particularly mannitol or a mixture of mannitol and isomalt, more particularly mannitol;
  an antioxidant, particularly ascorbic acid;
  a stabilizer, particularly disodium edetate; and
  a lubricant, particularly PEG6000.

In a particular embodiment of the invention, the pharmaceutical composition comprises:
  a compound of formula (I) as Form A or Form D, in particular as Form A;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
  a diluent, particularly mannitol or a mixture of mannitol and isomalt, more particularly mannitol;
  an antioxidant, particularly ascorbic acid;
  a stabilizer, particularly disodium edetate;
  a lubricant, particularly PEG6000;
  optionally a sweetener, particularly sucralose or sodium saccharin, most particularly sucralose; and
  optionally a flavor, particularly strawberry flavor or vanilla flavor.

In a particular embodiment of the invention, the pharmaceutical composition comprises:
  a compound of formula (I) as Form A or Form D, in particular as Form A;
  a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
  a diluent, particularly mannitol or a mixture of mannitol and isomalt, more particularly mannitol;
  an antioxidant, particularly ascorbic acid;
  a stabilizer, particularly disodium edetate;
  a lubricant, particularly PEG6000;

a preservative selected from sorbic acid or sodium benzoate;
optionally a sweetener, particularly sucralose or sodium saccharin, most particularly sucralose; and
optionally a flavor, particularly strawberry flavor or vanilla flavor.

In a particular embodiment of the invention, the pharmaceutical composition comprises:
- a compound of formula (I) as Form A or Form D, in particular as Form A;
- a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000;
- a preservative selected from potassium sorbate or sodium benzoate;
- optionally a sweetener, particularly sucralose or sodium saccharin, most particularly sucralose; and
- optionally a flavor, particularly strawberry flavor or vanilla flavor.

In a particular embodiment of the invention, the pharmaceutical composition comprises:
- 1 to 10% wt of a compound of formula (I) as Form A or Form D, in particular as Form A;
- 2 to 15% wt, in particular 4 to 6% wt of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- 40 to 90% wt of a diluent, particularly mannitol or a mixture of mannitol and isomalt, more particularly mannitol;
- 0.5 to 4% wt of an antioxidant, particularly ascorbic acid;
- 0.2 to 2% wt of a stabilizer, particularly disodium edetate;
- 0.5 to 2% wt of a lubricant, particularly PEG6000;
- 1 to 8% wt, in particular 1 to 4% wt, of a preservative selected from potassium sorbate or sodium benzoate;
- 0 to 3% wt of a sweetener, particularly sucralose or sodium saccharin, most particularly sucralose; and
- 0 to 20% wt of a flavor, particularly strawberry flavor or vanilla flavor;
wherein the total amount of ingredients does not exceed 100% wt.

In a particular embodiment of the invention, the pharmaceutical composition comprises:
- 1 to 10% wt of a compound of formula (I) as Form A or Form D, in particular as Form A;
- 2 to 15% wt of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- 40 to 80% wt of a diluent, particularly mannitol or a mixture of mannitol and isomalt, more particularly mannitol;
- 0.5 to 4% wt of an antioxidant, particularly ascorbic acid;
- 0.2 to 2% wt of a stabilizer, particularly disodium edetate;
- 0.5 to 2% wt of a lubricant, particularly PEG6000;
- 0 to 3% wt of a sweetener, particularly sucralose or sodium saccharin, most particularly sucralose; and
- 0 to 20% wt of a flavor, particularly strawberry flavor or vanilla flavor;
wherein the total amount of ingredients does not exceed 100% wt.

In a particular embodiment of the invention, the pharmaceutical composition comprises:
- 1 to 10% wt of a compound of formula (I) as Form A or Form D, in particular as Form A;
- 2 to 15% wt, in particular 4 to 6% wt of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- 40 to 80% wt of a diluent, particularly mannitol or a mixture of mannitol and isomalt, more particularly mannitol;
- 0.5 to 4% wt of an antioxidant, particularly ascorbic acid;
- 0.2 to 2% wt of a stabilizer, particularly disodium edetate;
- 0.5 to 2% wt of a lubricant, particularly PEG6000;
- 1 to 8% wt, in particular 1 to 4% wt, of a preservative selected from potassium sorbate or sodium benzoate;
- 0 to 3% wt of a sweetener, particularly sucralose or sodium saccharin, most particularly sucralose; and
- 0 to 20% wt of a flavor, particularly strawberry flavor or vanilla flavor;
wherein the total amount of ingredients does not exceed 100% wt.

In a particular embodiment of the invention, the pharmaceutical composition comprises:
- 1 to 10% wt of a compound of formula (I) as Form A or Form D, in particular as Form A;
- 2 to 15% wt, in particular 4 to 6% wt of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- 40 to 80% wt of a diluent, particularly mannitol or a mixture of mannitol and isomalt, more particularly mannitol;
- 0.5 to 4% wt of an antioxidant, particularly ascorbic acid;
- 0.2 to 2% wt of a stabilizer, particularly disodium edetate;
- 0.5 to 2% wt of a lubricant, particularly PEG6000;
- 1 to 8% wt, in particular 1 to 4% wt, of a preservative selected from sorbic acid or sodium benzoate;
- 0 to 3% wt of a sweetener, particularly sucralose or sodium saccharin, most particularly sucralose; and
- 0 to 20% wt of a flavor, particularly strawberry flavor or vanilla flavor;
wherein the total amount of ingredients does not exceed 100% wt.

In a particular embodiment of the invention, the pharmaceutical composition after constitution in water (80 ml) as solvent comprises:
- 0.25 to 2.5 mg/ml, in particular 0.25 to 0.5 mg/ml of a compound of formula (I) as Form A;
- 0.5 to 3.8 mg/ml, in particular 0.9 to 1.4 mg/ml of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;

10.0 to 22.5 mg/ml, in particular 18.0 to 22.0 mg/ml of a diluent, particularly mannitol or a mixture of mannitol and isomalt, more particularly mannitol;

0.1 to 1.0 mg/ml, in particular 0.15 to 0.5 mg/ml of an antioxidant, particularly ascorbic acid;

0.05 to 1.0 mg/ml, in particular 0.05 to 0.5 mg/ml of a stabilizer, particularly disodium edetate;

0.1 to 0.5 mg/ml, in particular 0.2 to 0.3 mg/ml of a lubricant, particularly PEG6000;

0.3 to 1.0 mg/ml, in particular 0.3 to 0.5 mg/ml of a preservative selected from sorbic acid or sodium benzoate;

0.0 to 0.75 mg/ml, in particular 0.1 to 0.4 mg/ml of a sweetener, particularly sucralose or sodium saccharin, most particularly sucralose; and 0.0 to 5.0 mg/ml, in particular 1.0 to 2.1 mg/ml a flavor, particularly strawberry flavor or vanilla flavor.

In a particular embodiment of the invention, the pharmaceutical composition comprises:

1 to 5% wt of 7-(4,7-diazaspiro[2.5]octan-7-yl)-2-(2,8-dimethylimidazo[1,2-b]pyridazin-6-yl)pyrido[1,2-a]pyrimidin-4-one as Form A or Form D, in particular as Form A;

2 to 8% wt of a tartrate buffer system;

60 to 75% wt of a mannitol as first diluent and 8 to 10% wt of isomalt as second diluent;

0.5 to 1.5% wt of ascorbic acid as antioxidant;

0.25 to 0.75% wt of disodium edetate as stabilizer;

0.5 to 2% wt of PEG6000 as lubricant;

0.5 to 1% wt of sucralose as sweetener; and 5 to 10% wt of strawberry flavor;

wherein the total amount of ingredients does not exceed 100% wt.

In a particular embodiment of the invention, the pharmaceutical composition comprises:

1 to 5% wt of 7-(4,7-diazaspiro[2.5]octan-7-yl)-2-(2,8-dimethylimidazo[1,2-b]pyridazin-6-yl)pyrido[1,2-a]pyrimidin-4-one as Form A or Form D, in particular as Form A;

2 to 8% wt, in particular 4 to 6% wt of a tartrate buffer system;

60 to 75% wt of a mannitol as first diluent and 10 to 15% wt of isomalt as second diluent;

0.5 to 1.5% wt of ascorbic acid as antioxidant;

0.25 to 0.75% wt of disodium edetate as stabilizer;

0.5 to 2% wt of PEG6000 as lubricant;

1 to 8% wt, in particular 1 to 4% wt, of sodium benzoate as a preservative;

0.5 to 1% wt of sucralose as sweetener; and 5 to 10% wt of strawberry flavor;

wherein the total amount of ingredients does not exceed 100% wt.

In a particular embodiment of the invention, the pharmaceutical composition after constitution in water (80 ml) as solvent comprises:

0.25 to 1.25 mg/ml, in particular 0.25 to 0.5 mg/ml of 7-(4,7-diazaspiro[2.5]octan-7-yl)-2-(2,8-dimethylimidazo[1,2-b]pyridazin-6-yl)pyrido[1,2-a]pyrimidin-4-one as Form A or Form D, in particular as Form A;

0.5 to 2.0 mg/ml, in particular 0.9 to 1.4 mg/ml of a tartrate buffer system;

15.0 to 18.75 mg/ml of a mannitol as first diluent and 2.0 to 3.75 mg/ml of isomalt as second diluent;

0.18 to 0.53 mg/ml of ascorbic acid as antioxidant;

0.05 to 0.15 mg/ml of disodium edetate as stabilizer;

0.1 to 0.5 mg/ml, in particular 0.2 to 0.3 mg/ml of PEG6000 as lubricant;

0.3 to 0.8 mg/ml of sodium benzoate as a preservative;

0.13 to 0.25 mg/ml of sucralose as sweetener; and 1.25 to 2.5 mg/ml of strawberry flavor.

In a particular embodiment of the invention, the pharmaceutical composition comprises:

1 to 5% wt of 7-(4,7-diazaspiro[2.5]octan-7-yl)-2-(2,8-dimethylimidazo[1,2-b]pyridazin-6-yl)pyrido[1,2-a]pyrimidin-4-one as Form A;

2 to 8% wt, in particular 4 to 6% wt, of a tartaric acid;

60 to 75% wt of a mannitol and 8 to 10% wt of isomalt;

0.5 to 1.5% wt of ascorbic acid;

0.25 to 0.75% wt of disodium edetate;

0.5 to 2% wt of PEG6000 as lubricant;

1 to 8% wt, in particular 1 to 4% wt, of sodium benzoate;

0.5 to 1% wt of sucralose; and 5 to 10% wt of strawberry flavor;

wherein the total amount of ingredients does not exceed 100% wt.

In a particular embodiment of the invention, the pharmaceutical composition after constitution in water (80 ml) as solvent comprises:

0.25 to 1.25 mg/ml, in particular 0.25 to 0.5 mg/ml of 7-(4,7-diazaspiro[2.5]octan-7-yl)-2-(2,8-dimethylimidazo[1,2-b]pyridazin-6-yl)pyrido[1,2-a]pyrimidin-4-one as Form A;

0.5 to 2.0 mg/ml, in particular 0.9 to 1.4 mg/ml of a tartaric acid;

15.0 to 18.75 mg/ml of a mannitol and 2.0 to 3.75 mg/ml of isomalt;

0.18 to 0.53 mg/ml of ascorbic acid;

0.05 to 0.15 mg/ml of disodium edetate;

0.1 to 0.5 mg/ml, in particular 0.2 to 0.3 mg/ml of PEG6000;

0.3 to 0.8 mg/ml of sodium benzoate;

0.13 to 0.25 mg/ml of sucralose; and 1.25 to 2.5 mg/ml of strawberry flavor.

Another embodiment of the invention relates to a kit for the preparation of pharmaceutical compositions comprising a compound of formula (I) or a pharmaceutically acceptable salt thereof, wherein the kit comprises:

a powder blend comprising a compound of formula (I) as Form A or Form D, in particular as Form A, and water as solvent for constitution.

Another embodiment of the invention relates to a kit for the preparation of pharmaceutical compositions comprising a compound of formula (I) or a pharmaceutically acceptable salt thereof, wherein the kit comprises:

a powder blend comprising a compound of formula (I) as Form A, and water as solvent for constitution, in particular with 80 ml.

Another embodiment of the invention relates to a kit for the preparation of pharmaceutical compositions comprising a compound of formula (I) or a pharmaceutically acceptable salt thereof, wherein the kit comprises:

the pharmaceutical composition as described herein comprising a compound of formula (I) as Form A, and water as solvent for constitution, in particular with 80 ml of purified water. Another embodiment of the invention relates to a kit for the preparation of pharmaceutical compositions comprising a compound of formula (I) or a pharmaceutically acceptable salt thereof, wherein the kit comprises:

a compound of formula (I) as Form A or Form D, in particular as Form A, a powder blend as vehicle for constitution, and optionally water as solvent for constitution.

Another embodiment of the invention relates to a kit for the preparation of pharmaceutical compositions comprising a compound of formula (I) or a pharmaceutically acceptable salt thereof, wherein the kit comprises:
- a compound of formula (I) as Form A,
- a powder blend as vehicle for constitution, and
- optionally water as solvent for constitution, in particular with 80 ml of purified water.

Another embodiment relates to a powder blend as vehicle suitable for constitution of a compound of formula (I) as Form A or Form D, in particular as Form A, as described herein comprising:
- a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid; and
- a diluent, particularly mannitol or a mixture of mannitol and isomalt, more particularly mannitol.

Another embodiment relates to a powder blend as vehicle suitable for constitution of a compound of formula (I) as described herein or a pharmaceutically acceptable salt thereof, comprising:
- a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate; and
- a lubricant, particularly PEG6000.

Another embodiment relates to a powder blend as vehicle suitable for constitution of a compound of formula (I) as Form A or Form D, in particular as Form A, as described herein comprising:
- a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000;
- optionally a sweetener, particularly sucralose or sodium saccharin, most particularly sucralose; and
- optionally a flavor, particularly strawberry flavor or vanilla flavor.

Another embodiment relates to a powder blend as vehicle suitable for constitution of a compound of formula (I) as Form A or Form D, in particular as Form A, as described herein, comprising:
- 3 to 15% wt of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- 40 to 80% wt of a diluent, particularly mannitol or a mixture of mannitol and isomalt, more particularly mannitol;
- 1 to 4% wt of an antioxidant, particularly ascorbic acid;
- 0.2 to 2% wt of a stabilizer, particularly disodium edetate;
- 0.5 to 2% wt of a lubricant, particularly PEG6000;
- 0 to 3% wt of a sweetener, particularly sucralose or sodium saccharin, most particularly sucralose; and
- 0 to 20% wt of a flavor, particularly strawberry flavor or vanilla flavor;

wherein the total amount of ingredients does not exceed 100% wt.

Another embodiment relates to a powder blend as vehicle suitable for constitution of a compound of formula (I) as Form A or Form D, in particular as Form A, as described herein, comprising:
- 3 to 15% wt of a buffer system, particularly a buffer system selected from citrate, malate, maleate, or tartrate, more particularly malate or tartrate, most particularly tartrate; or alternatively the corresponding acid of a buffer system alone as acidifier, particularly tartaric acid;
- 40 to 90% wt, in particular 40 to 80% wt, of a diluent, particularly mannitol or a mixture of mannitol and isomalt, more particularly mannitol;
- 1 to 4% wt of an antioxidant, particularly ascorbic acid;
- 0.2 to 2% wt of a stabilizer, particularly disodium edetate;
- 0.5 to 2% wt of a lubricant, particularly PEG6000;
- 1 to 8% wt, in particular 1 to 4% wt, of a preservative, particularly sodium benzoate;
- 0 to 3% wt of a sweetener, particularly sucralose or sodium saccharin, most particularly sucralose; and
- 0 to 20% wt of a flavor, particularly strawberry flavor or vanilla flavor;

wherein the total amount of ingredients does not exceed 100% wt.

Another embodiment relates to a powder blend as vehicle suitable for constitution of a compound of formula (I) as Form A or Form D, in particular as Form A, as described herein, comprising:
- 3 to 7% wt of a tartaric acid;
- 60 to 75% wt of a mannitol as first diluent and 10 to 15% wt of isomalt as second diluent;
- 0.5 to 1.0% wt of ascorbic acid as antioxidant;
- 0.3 to 0.7% wt of disodium edetate as stabilizer;
- 0.5 to 2% wt of PEG6000 as lubricant;
- 0.6 to 1.0% wt of sucralose as sweetener; and
- 5 to 10% wt of strawberry flavor;

wherein the total amount of ingredients does not exceed 100% wt.

Another embodiment relates to a powder blend as vehicle suitable for constitution of a compound of formula (I) as Form A or Form D, in particular as Form A, as described herein, comprising:
- 3 to 7% wt, in particular 4 to 6% wt of a tartaric acid;
- 60 to 75% wt of a mannitol as first diluent and 10 to 15% wt of isomalt as second diluent;
- 0.5 to 1.0% wt of ascorbic acid as antioxidant;
- 0.3 to 0.7% wt of disodium edetate as stabilizer;
- 0.5 to 2% wt of PEG6000 as lubricant;
- 1 to 8% wt of sodium benzoate as a preservative, in particular 1 to 4% wt of sodium benzoate as a preservative;
- 0.6 to 1.0% wt of sucralose as sweetener; and
- 5 to 10% wt of strawberry flavor;

wherein the total amount of ingredients does not exceed 100% wt.

Another embodiment relates to a powder blend as vehicle suitable for constitution of a compound of formula (I) as Form A or Form D, in particular as Form A, as described herein, comprising:
- 3 to 7% wt, in particular 4 to 6% wt of a tartaric acid;
- 60 to 75% wt of a mannitol and 10 to 15% wt of isomalt;

0.5 to 1.0% wt of ascorbic acid;
0.3 to 0.7% wt of disodium edetate;
0.5 to 2% wt of PEG6000;
1 to 8% wt of sodium benzoate, in particular 1 to 4% wt of sodium benzoate;
0.6 to 1.0% wt of sucralose; and
5 to 10% wt of strawberry flavor;
wherein the total amount of ingredients does not exceed 100% wt.

Another embodiment relates to a powder blend as vehicle suitable for constitution of a compound of formula (I) as Form A, as described herein, wherein after constitution in water (80 ml) as solvent comprising:

the pharmaceutical composition after constitution in water (80 ml) as solvent comprises:
  0.25 to 1.25 mg/ml, in particular 0.25 to 0.5 mg/ml of 7-(4,7-diazaspiro[2.5]octan-7-yl)-2-(2,8-dimethylimidazo[1,2-b]pyridazin-6-yl)pyrido[1,2-a]pyrimidin-4-one as Form A;
  0.5 to 2.0 mg/ml, in particular 0.9 to 1.4 mg/ml of a tartaric acid;
  15.0 to 18.75 mg/ml of a mannitol and 2.0 to 3.75 mg/ml of isomalt;
  0.18 to 0.53 mg/ml of ascorbic acid;
  0.05 to 0.15 mg/ml of disodium edetate;
  0.1 to 0.5 mg/ml, in particular 0.2 to 0.3 mg/ml of PEG6000;
  0.3 to 0.8 mg/ml of sodium benzoate;
  0.13 to 0.25 mg/ml of sucralose; and
  1.25 to 2.5 mg/ml of strawberry flavor.

The compound of formula (I) possess valuable pharmacological properties and has been found to enhance inclusion of exon 7 of SMN1 and/or SMN2 into mRNA transcribed from the SMN1 and/or SMN2 gene, thereby increasing expression of SMN protein in a human subject in need thereof.

The compounds of the present invention can be used, either alone or in combination with other drugs, for the treatment, prevention, delaying progression and/or amelioration of diseases caused by an inactivating mutation or deletion in the SMN1 gene and/or associated with loss or defect of SMN1 gene function. These diseases include, but are not limited to spinal muscular atrophy (SMA).

A particular embodiment of the present invention relates to a pharmaceutical composition comprising a compound of formula (I), in particular as Form A as defined above and one or more pharmaceutically acceptable excipients for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of SMA.

A particular embodiment of the present invention relates to a pharmaceutical composition comprising a compound of formula (I), in particular as Form A, as defined above for use as therapeutically active substances, especially for use as therapeutically active substances for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of spinal muscular atrophy (SMA).

A particular embodiment of the present invention relates to a pharmaceutical composition comprising a compound of formula (I), in particular as Form A, as defined above for the use in the treatment, prevention, delaying progression and/or amelioration of diseases caused by an inactivating mutation or deletion in the SMN1 gene and/or associated with loss or defect of SMN1 gene function, particularly for use in the treatment, prevention, delaying progression and/or amelioration of spinal muscular atrophy (SMA).

A particular embodiment of the present invention relates to a method for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of spinal muscular atrophy (SMA), which method comprises administering a pharmaceutical composition comprising a compound of formula (I), in particular as Form A, as defined above to a subject.

A particular embodiment of the present invention relates to the use of a pharmaceutical composition comprising a compound of formula (I), in particular as Form A, as defined above for the treatment, prevention, delaying progression and/or amelioration of diseases caused by an inactivating mutation or deletion in the SMN1 gene and/or associated with loss or defect of SMN1 gene, particularly for the treatment, prevention, delaying progression and/or amelioration of spinal muscular atrophy (SMA).

A particular embodiment of the present invention relates to the use of a pharmaceutical composition comprising a compound of formula (I), in particular as Form A, for the preparation of medicaments for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of spinal muscular atrophy (SMA). Such medicaments comprise compounds of formula (I), in particular as Form A as defined above.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

The following examples are provided for the purpose of further illustration and are not intended to limit the scope of the claimed invention.

In the present application, the following abbreviations and definitions are used: br (broad); BuLi (butyllithium); CDCl$_3$ (deuterated chloroform); d (doublet); eq. (equivalent); g (gram); GC (gas chromatography); h (hour); HCl (hydrochloric acid); H$_2$O (water); HPLC (High-Performance Liquid Chromatography); ISP (Isotopic Spin Population); KOH (Potassium Hydroxide); L (liter); LDA (Lithium Diisopropylamide); LCMS (Liquid chromatography-mass spectrometry); M (Molar); m (multiplet); MS (Mass Spectroscopy); mL (milliliter); NaOH (sodium hydroxide); NMR (nuclear magnetic resonance); Pd(dba)$_3$ (tris(dibenzylideneacetone) dipalladium(0)); Pd(Xantphos)Cl$_2$ (Dichloro[9,9-dimethyl-4,5-bis(diphenylphosphino)-xanthene]palladium(II)); s (singlet); sec (second); t (triplet); t-Bu Brett Phos (2-(Di-tert-butylphosphino)-2',4',6'-triisopropyl-3,6-dimethoxy-1,1'-biphenyl); THF (tetrahydrofuran);

Example 1: 7-(4,7-diazaspiro[2.5]octan-7-yl)-2-(2,8-dimethylimidazo[1,2-b]pyridazin-6-yl)pyrido[1,2-a]pyrimidin-4-one (Form A without seeds)

7-(4,7-diazaspiro[2.5]octan-7-yl)-2-(2,8-dimethylimidazo[1,2-b]pyridazin-6-yl)pyrido[1,2-a]pyrimidin-4-one (5.81 g, 13.71 mmol) was dissolved in water (28 g) and aqueous hydrochloric acid (37%, 2.61 g, 26.49 mmol) at 30-33° C. The hydrochloric acid salt solution was added to the solution of NaOH (1.15 g, 28.75 mmol) in ethanol (220 g) at 60° C. within 100 minutes upon which spontaneous crystallization occurred. The equipment for the hydrochloric acid salt solution was rinsed with water (1.2 g) which was added to the suspension. The suspension was cooled to 40° C. and stirred overnight. The precipitate was filtered off, washed with a mixture of water/ethanol 88:12 (16.5 g) three times followed by ethanol (16.5 g) and dried under high vacuum at 60° C. for 21 hours to afford Form A of 7-(4,7-diazaspiro[2.5]octan-7-yl)-2-(2,8-dimethylimidazo[1,2-b]pyridazin-6-yl)pyrido[1,2-a]pyrimidin-4-one (4.95 g, 90.0%).

Example 2: 7-(4,7-diazaspiro[2.5]octan-7-yl)-2-(2,8-dimethylimidazo[1,2-b]pyridazin-6-yl)pyrido[1,2-a]pyrimidin-4-one (Form A)

7-(4,7-diazaspiro[2.5]octan-7-yl)-2-(2,8-dimethylimidazo[1,2-b]pyridazin-6-yl)pyrido[1,2-a]pyrimidin-4-one (5.81 g, 13.71 mmol) was dissolved in water (28 g) and aqueous hydrochloric acid (37%, 2.57 g, 26.08 mmol) at 30-33° C. A first portion of the hydrochloric acid salt solution (3.64 g) was added to the solution of NaOH (1.12 g, 28.00 mmol) in ethanol (220 g) at 60° C. Seeding was performed by addition of a suspension of Form A crystals (0.055 g, 0.01 mmol) in ethanol (1.7 g). The remaining part of the hydrochloric acid salt solution was added to the solution of NaOH at 60° C. within 87 minutes. The equipment for the hydrochloric acid salt solution was rinsed with water (1.2 g) which was added to the suspension. The suspension was cooled to 40° C. and stirred overnight. The precipitate was filtered off, washed with a mixture of water/ethanol 88:12 (16.5 g) four times followed by ethanol (16.5 g) and dried under high vacuum at 60° C. for 21 hours to afford Form A of 7-(4,7-diazaspiro[2.5]octan-7-yl)-2-(2,8-dimethylimidazo[1,2-b]pyridazin-6-yl)pyrido[1,2-a]pyrimidin-4-one (5.06 g, 91.1%).

Example 3: 7-(4,7-diazaspiro[2.5]octan-7-yl)-2-(2,8-dimethylimidazo[1,2-b]pyridazin-6-yl)pyrido[1,2-a]pyrimidin-4-one (Form D)

Form A of 7-(4,7-diazaspiro[2.5]octan-7-yl)-2-(2,8-dimethylimidazo[1,2-b]pyridazin-6-yl)pyrido[1,2-a]pyrimidin-4-one (0.5 g, 1.23 mmol) was suspended in a mixture of ethanol/water 4:1 weight/weight (2.1 g). The suspension was stirred at 35° C. for 4 days. The solids were isolated and dried under vacuum (200 mbar at 30° C. for 4 hours, or 100 mbar at 40° C. for 2 hours) to afford Form D of 7-(4,7-diazaspiro[2.5]octan-7-yl)-2-(2,8-dimethylimidazo[1,2-b]pyridazin-6-yl)pyrido[1,2-a]pyrimidin-4-one.

Example 4: Oral Solutions Comprising 7-(4,7-diazaspiro[2.5]octan-7-yl)-2-(2,8-dimethylimidazo[1,2-b]pyridazin-6-yl)pyrido[1,2-a]pyrimidin-4-one 7-(4,7-diazaspiro[2.5]octan-7-yl)-2-(2,8-dimethylimidazo[1,2-b]pyridazin-6-yl)pyrido[1,2-a]pyrimidin-4-one, can be formulated as oral aqueous solution by dissolving the drug substance in a buffer system at pH of less than pH 4, particularly between pH 3.0 and pH 3.2, in order to provide sufficiently high drug concentration, e.g., citric buffer, malate, maleate, or tartrate buffer, more particularly malate or tartrate, most particularly tartrate buffer.

Long-term stability of formulations of 7-(4,7-diazaspiro[2.5]octan-7-yl)-2-(2,8-dimethylimidazo[1,2-b]pyridazin-6-yl)pyrido[1,2-a]pyrimidin-4-one can be achieved by preparing a dry powder or granulation for constitution of an oral solution. Buffer system can be incorporated into dry formulation by the selection of organic acid and salts thereof as fine crystalline powders, e.g., tribasic sodium citrate dihydrate and citric acid anhydrous, sodium malate, and malic acid, or preferably potassium sodium tartrate and tartaric acid.

Powders or granules comprising 7-(4,7-diazaspiro[2.5]octan-7-yl)-2-(2,8-dimethylimidazo[1,2-b]pyridazin-6-yl)pyrido[1,2-a]pyrimidin-4-one may comprise a extragranular filler, such as sorbitol, isomalt, or mannitol, and combinations thereof, which ensure fast dissolution of the powder blend during constitution of the oral solution. In introduction of a diluent the powder blend can be granulated by dry compaction in order to improve the flowability and to ensure robust uniformity.

Ingredients for the constitution of a solvent system for 7-(4,7-diazaspiro[2.5]octan-7-yl)-2-(2,8-dimethylimidazo[1,2-b]pyridazin-6-yl)pyrido[1,2-a]pyrimidin-4-one, more particularly as Form A, can be formulated as separate formulation. The constituted solvent can be used for dissolution of 7-(4,7-diazaspiro[2.5]octan-7-yl)-2-(2,8-dimethylimidazo[1,2-b]pyridazin-6-yl)pyrido[1,2-a]pyrimidin-4-one, more particularly as Form A, in a bottle at the start of the in-use period of the oral solution.

The constituted oral solution of 7-(4,7-diazaspiro[2.5]octan-7-yl)-2-(2,8-dimethylimidazo[1,2-b]pyridazin-6-yl)pyrido[1,2-a]pyrimidin-4-one, more particularly as Form A, in a buffer can be can provide in-use times of more than 2 weeks by the use of stabilizers and antioxidants, such as vitamin E TPGS, disodium edetate, butyl hydroxyl toluol, riboflavin, or preferably ascorbic acid, and in combinations thereof.

Table 8 provides a number of oral solutions providing stability in solution of more than 2 weeks.

TABLE 8

Oral solutions of 7-(4,7-diazaspiro[2.5]octan-7-yl)-2-(2,8-dimethylimidazo[1,2-b]pyridazin-6-yl)pyrido[1,2-a]pyrimidin-4-one at concentration of 0.1 mg/ml, 1.0 mg/ml and 3.0 mg/ml.

| Ingredients | Composition 1A 0.1 mg/ml (mg) | Composition 1B 1.0 mg/ml (mg) | Composition 1C 3.0 mg/ml (mg) | Composition 1D 1.0 mg/ml (mg) |
|---|---|---|---|---|
| 7-(4,7-diazaspiro[2.5]octan-7-yl)-2-(2,8-dimethylimidazo[1,2-b]pyridazin-6-yl)pyrido[1,2-a]pyrimidin-4-one | 20.0 | 200.0 | 600.0 | 200 |

TABLE 8-continued

Oral solutions of 7-(4,7-diazaspiro[2.5]octan-7-yl)-2-(2,8-dimethylimidazo[1,2-b]pyridazin-6-yl)pyrido[1,2-a]pyrimidin-4-one at concentration of 0.1 mg/ml, 1.0 mg/ml and 3.0 mg/ml.

| Ingredients | Composition 1A 0.1 mg/ml (mg) | Composition 1B 1.0 mg/ml (mg) | Composition 1C 3.0 mg/ml (mg) | Composition 1D 1.0 mg/ml (mg) |
| --- | --- | --- | --- | --- |
| Citric acid anhydrous | 1077.2 | 1077.2 | 1921.2 | — |
| Sodium citrate dihydrate | 115.6 | 115.6 | 0.0 | — |
| Tartaric acid anhydrous | — | — | — | 1274.0 |
| Potassium Sodium tartrate x4H$_2$O | — | — | — | 347.6 |
| Ascorbic acid | 70.5 | 70.5 | 211.5 | 70.5 |
| Disodium edetate | 33.6 | 33.6 | 100.8 | 33.6 |
| Water for injection | ad 200.0 ml | ad 200.0 ml | ad 200.0 ml | ad 200.0 ml |

Example 5 Powder Blends as Vehicles for Constitution of Oral Solutions of 7-(4,7-diazaspiro[2.5]octan-7-yl)-2-(2,8-dimethylimidazo[1,2-b]pyridazin-6-yl)pyrido[1,2-a]pyrimidin-4-one Table 9 represents a granulated powder blend for the constitution of a solvent, which is suitable to dissolve 7-(4,7-diazaspiro[2.5]octan-7-yl)-2-(2,8-dimethylimidazo[1,2-b]pyridazin-6-yl)pyrido[1,2-a]pyrimidin-4-one, and to obtain an oral solution at pH3.4 which is stable for more than 2 weeks. The blend contains polyethylene glycol 6000 as water soluble lubricant, sodium benzoate as preservative, sucralose as sweetener, and strawberry flavor for the purpose of improving the taste, particularly for use in pediatric patients.

The compositions of Table 9 together with 79 ml water provide constitution solvents suitable for the dissolution of 7-(4,7-diazaspiro[2.5]octan-7-yl)-2-(2,8-dimethylimidazo[1,2-b]pyridazin-6-yl)pyrido[1,2-a]pyrimidin-4-one (20 mg and 60 mg respectively).

TABLE 9

Powder blend of a vehicle for constitution of an oral solution of 7-(4,7-diazaspiro[2.5]octan-7-yl)-2-(2,8-dimethylimidazo[1,2-b]pyridazin-6-yl)pyrido[1,2-a]pyrimidin-4-one at pH 3.4 with API concentrations of 0.25 and 1.5 mg/ml.

| Dedicated to concentration of 7-(4,7-diazaspiro[2.5]octan-7-yl)-2-(2,8-dimethylimidazo[1,2-b]pyridazin-6-yl)pyrido[1,2-a]pyrimidin-4-one in solution: | Composition 2A 0.25 mg/ml (mg) | Composition 2B 1.5 mg/ml (mg) |
| --- | --- | --- |
| intragranular: | | |
| Mannitol | 2019.93 | 1948.63 |
| Tartaric Acid | 92.00 | 163.30 |
| Sodium Benzoate micronized | 64.00 | 64.00 |
| Ascorbic Acid fine powder | 28.18 | 28.18 |
| PEG 6000 | 25.00 | 25.00 |
| Disodium Edetate | 14.89 | 14.89 |
| Sucralose | 16.00 | 16.00 |
| Total intragranular: | 2260.0 | 2260.0 |
| extragranular: | | |
| Strawberry flavor | 240.0 | 240.0 |
| Total: | 2'500.0 | 2'500.0 |

Example 6: Powder Blends Comprising 7-(4,7-diazaspiro[2.5]octan-7-yl)-2-(2,8-dimethylimidazo[1,2-b]pyridazin-6-yl)pyrido[1,2-a]pyrimidin-4-One for Constitution of Oral Solutions Table 10 represents an oral solutions comprising 7-(4,7-diazaspiro[2.5]octan-7-yl)-2-(2,8-dimethylimidazo[1,2-b]pyridazin-6-yl)pyrido[1,2-a]pyrimidin-4-one which have been constituted by the use of constituted vehicle solution from example 4 for the dissolution of the active compound. The vehicle is suitable for constitution of an oral solution at pH 3.4 which is stable for more than 2 weeks. The compositions of Table 9 together with 79 ml of water provide oral solutions comprising 1 mg/ml, 3 mg/ml of 7-(4,7-diazaspiro[2.5]octan-7-yl)-2-(2,8-dim ethylimidazo[1,2-b]pyridazin-6-yl)pyri do[1,2-a]pyrimidin-4-one.

TABLE 10

Oral solution constitution of an oral solution comprising 7-(4,7-diazaspiro[2.5]octan-7-yl)-2-(2,8-dimethylimidazo[1,2-b]pyridazin-6-yl)pyrido[1,2-a]pyrimidin-4-one at pH 3.5 with API concentrations of 1.0 and 3.0 mg/ml.

| | Composition 2A 1 mg/ml (mg) | Composition 2B 3 mg/ml (mg) |
| --- | --- | --- |
| 7-(4,7-diazaspiro[2.5]octan-7-yl)-2-(2,8-dimethylimidazo[1,2-b]pyridazin-6-yl)pyrido[1,2-a]pyrimidin-4-one | 80 | 240 |
| Mannitol | 1'525.78 | 1'554.58 |
| Tartaric acid | 148.00 | 180.00 |
| Potassium Sodium tartrate *4H$_2$O | 173.60 | 112.80 |
| Sodium benzoate micronized | 80.00 | 80.00 |
| Ascorbic acid fine powder | 28.18 | 28.18 |
| Disodium edetate | 13.44 | 13.44 |
| PEG 6000 | 25.00 | 25.00 |
| Sucralose | 16.00 | 16.00 |
| Mannitol 160C | 250.00 | 250.00 |
| Strawberry flavor | 240.00 | 240.00 |
| Water | ad 80 ml | ad 80 ml |
| Total: | 80 ml | 80 ml |

Example 7: Powder blends of 7-(4,7-diazaspiro[2.5]octan-7-yl)-2-(2,8-dimethylimidazo[1,2-b]pyridazin-6-yl)pyrido[1,2-a]pyrimidin-4-one for constitution of oral solutions Table 11 provides powder blends comprising 7-(4,7-diazaspiro[2.5]octan-7-yl)-2-(2,8-dimethylimidazo[1,2-b]pyridazin-6-yl)pyrido[1,2-a]pyrimidin-4-one which may be used to constitute oral solutions together with 90 ml water. The compositions of Table 10 may also be constituted from solvent prepared from a vehicle powder blend (similar to example 4) followed by dissolution of API.

TABLE 11

Oral solutions of 7-(4,7-diazaspiro[2.5]octan-7-yl)-2-(2,8-dimethylimidazo[1,2-b]pyridazin-6-yl)pyrido[1,2-a]pyrimidin-4-one at concentration of 1.0 mg/ml in a bottle containing 90 ml solution.

| | Composition 3A (mg) | Composition 3B (mg) |
|---|---|---|
| 7-(4,7-diazaspiro[2.5]octan-7-yl)-2-(2,8-dimethylimidazo[1,2-b]pyridazin-6-yl)pyrido[1,2-a]pyrimidin-4-one | 90.0 | 90.0 |
| Mannitol | 1200.0 | 1200.0 |
| Maltodextrin | — | 450.0 |
| Lactose | 450.0 | — |
| D-L tartaric acid | 573.3 | 573.3 |
| Disodium tartrate dihydrate | 156.4 | 156.4 |
| Ascorbic acid | 31.7 | 31.7 |
| Disodium edetate | 15.1 | 15.1 |
| Sucralose | 18.0 | — |
| Sodium saccharin | — | 18.0 |
| Sodium benzoate | 90.0 | — |
| Sorbic acid | — | 90.0 |
| PEG 6000 | 18.0 | — |
| Strawberry flavor | 180.0 | — |
| Vanilla flavor | — | 180.0 |
| Total per bottle (mg): | 2822.5 | 2804.5 |

Example 8: Powder blends of 7-(4,7-diazaspiro[2.5]octan-7-yl)-2-(2,8-dimethylimidazo[1,2-b]pyridazin-6-yl)pyrido[1,2-a]pyrimidin-4-one for constitution of oral solutions Table 12 provides powder blends comprising 7-(4,7-diazaspiro[2.5]octan-7-yl)-2-(2,8-dimethylimidazo[1,2-b]pyridazin-6-yl)pyrido[1,2-a]pyrimidin-4-one which may be used to constitute oral solutions together with water to obtain 80 ml solution. The compositions of Table 11 may also be constituted from solvent prepared from a vehicle powder blend (similar to example 5) followed by dissolution of API.

TABLE 12

Powder blend for the preparation of an oral solution of 7-(4,7-diazaspiro[2.5]octan-7-yl)-2-(2,8-dimethylimidazo[1,2-b]pyridazin-6-yl)pyrido[1,2-a]pyrimidin-4-one at concentration of 1 mg/ml in a bottle containing 80 ml solution.

| | Quantity per bottle (mg) | Percentage solids (% wt) |
|---|---|---|
| intragranular: | | |
| 7-(4,7-diazaspiro[2.5]octan-7-yl)-2-(2,8-dimethylimidazo[1,2-b]pyridazin-6-yl)pyrido[1,2-a]pyrimidin-4-one | 80.00 | 3.20 |
| Mannitol (Parteck M100) | 1445.94 | 57.84 |
| D-L tartaric acid | 147.68 | 5.91 |
| Potassium sodium tartrate*4H$_2$O | 173.76 | 6.95 |
| Sodium benzoate | 80.00 | 3.20 |
| Ascorbic acid | 28.18 | 1.13 |
| Disodium edetate | 13.44 | 0.54 |
| Sucralose | 16.00 | 0.64 |
| PEG 6000 | 25.00 | 1.00 |
| Total Dry: extragranular: | 2010.00 | 80.40 |
| Strawberry flavor PHS-180152 | 240.00 | 10.00 |
| Mannitol 160C | 250.00 | 9.60 |
| Total per bottle (mg): | 2500.00 | 100.00 |

Example 9: Powder blends of 7-(4,7-diazaspiro[2.5]octan-7-yl)-2-(2,8-dimethylimidazo[1,2-b]pyridazin-6-yl)pyrido[1,2-a]pyrimidin-4-one for constitution of oral solutions Table 13 provides powder blends comprising 7-(4,7-diazaspiro[2.5]octan-7-yl)-2-(2,8-dimethylimidazo[1,2-b]pyridazin-6-yl)pyrido[1,2-a]pyrimidin-4-one which may be used to constitute oral solutions with water to obtain 80 mL solution. The compositions of Table 12 may also be constituted from solvent prepared from a vehicle powderblend (similar to example 4) followed by dissolution of API.

TABLE 13

Powder blend for the preparation of an oral solution of 7-(4,7-diazaspiro[2.5]octan-7-yl)-2-(2,8-dimethylimidazo[1,2-b]pyridazin-6-yl)pyrido[1,2-a]pyrimidin-4-one at concentration of 0.25 and 0.75 mg/ml in a bottle containing 80 ml solution.

| | Quantity per bottle (mg) | percentage solids (% wt) | Quantity per bottle (mg) | percentage solids (% wt) |
|---|---|---|---|---|
| intragranular: | | | | |
| 7-(4,7-diazaspiro[2.5]octan-7-yl)-2-(2,8-dimethylimidazo[1,2-b]pyridazin-6-yl)pyrido[1,2-a]pyrimidin-4-one | 20.00 | 1.00 | 60.00 | 3.00 |
| Mannitol (Parteck M100) | 1402.85 | 70.14 | 1344.70 | 67.24 |
| D-L tartaric acid | 92.00 | 4.60 | 120.50 | 6.03 |
| Isomalt 801 | 247.60 | 12.38 | 237.25 | 11.86 |
| Sodium benzoate | 30.00 | 1.50 | 30.00 | 1.50 |
| Ascorbic acid | 14.10 | 0.71 | 14.10 | 0.71 |
| Disodium edetate dihydrate | 7.45 | 0.37 | 7.45 | 0.37 |
| Sucralose | 16.00 | 0.80 | 16.00 | 0.80 |
| PEG 6000 | 20.00 | 1.00 | 20.00 | 1.00 |
| Total Dry: extragranular: | 1850.0 | 92.5 | 1850.0 | 92.5 |
| Strawberry flavor PHS-180152 | 150.00 | 7.50 | 150.00 | 7.50 |
| Total per bottle (mg): | 2000.0 | 100.0 | 2000.0 | 100.0 |

What is claimed is:

1. A solid form of a compound of formula (I)

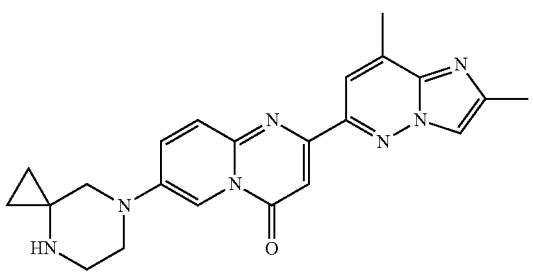

wherein the solid form is crystalline Form A having an x-ray powder diffraction (XRPD) pattern comprising at least two XRPD peaks selected from the group consisting of 8.3 (±0.2) degrees two-theta, 11.4 (±0.2) degrees two-theta, 15.1 (±0.2) degrees two-theta, 15.9 (±0.2) degrees two-theta, 17.0 (±0.2) degrees two-theta. 24.0 (±0.2) degrees two-theta, and 25.6 (±0.2) degrees two-theta angle of diffraction.

2. The solid form of claim 1, wherein said solid form is crystalline Form A having an XRPD pattern comprising at least three XRPD peaks selected from the group consisting of 8.3 (±0.2) degrees two-theta, 11.4 (±0.2) degrees two-theta, 15.1 (±0.2) degrees two-theta, 15.9 (±0.2) degrees two-theta, 17.0 (±0.2) degrees two-theta, 24.0 (±0.2) degrees two-theta, and 25.6 (±0.2) degrees two-theta angle of diffraction.

3. The solid form of claim 1, wherein the x-ray powder diffraction pattern is obtained from a Cu Kα source.

4. The solid form of claim 1, wherein said solid form is crystalline Form A having an XRPD pattern comprising XRPD peaks at 8.3 (±0.2) degrees two-theta, 11.4 (±0.2) degrees two-theta, 12.7 (±0.2) degrees two-theta, 13.0 (±0.2) degrees two-theta, 15.1 (±0.2) degrees two-theta, 15.9 (±0.2) degrees two-theta, 17.0 (±0.2) degrees two-theta, 19.7 (±0.2) degrees two-theta, 22.4 (±0.2) degrees two-theta, 24.0 (±0.2) degrees two-theta, and 25.6 (±0.2) degrees two-theta angle of diffraction.

5. The solid form of claim 1, wherein said solid form is crystalline Form A having an XRPD pattern comprising XRPD peaks at 8.3 (±0.2) degrees two-theta, 11.4 (±0.2) degrees two-theta, 12.7 (±0.2) degrees two-theta, 13.0 (±0.2) degrees two-theta, 15.1 (±0.2) degrees two-theta, 15.4 (±0.2) degrees two-theta, 15.9 (±0.2) degrees two-theta, 16.7 (±0.2) degrees two-theta, 17.0 (±0.2) degrees two-theta, 17.5 (±0.2) degrees two-theta, 18.7 (±0.2) degrees two-theta, 19.4 (±0.2) degrees two-theta, 19.7 (±0.2) degrees two-theta, 19.8 (±0.2) degrees two-theta, 21.3 (±0.2) degrees two-theta, 22.4 (±0.2) degrees two-theta, 23.6 (±0.2) degrees two-theta, 24.0 (±0.2) degrees two-theta, 24.7 (±0.2) degrees two-theta, 25.6 (±0.2) degrees two-theta, 26.7 (±0.2) degrees two-theta, 26.8 (±0.2) degrees two-theta, 27.4 (±0.2) degrees two-theta, 29.3 (±0.2) degrees two-theta, and 30.7 (±0.2) degrees two-theta angle of diffraction.

6. The solid form of claim 1, wherein said solid form is crystalline Form A having an IR spectrum comprising at least one peak at a position selected from the group consisting of 848 (±2) cm$^{-1}$, 885 (±2) cm$^{-1}$, 939 (±2) cm$^{-1}$, and 1218 (±2) cm$^{-1}$.

7. The solid form of claim 1, wherein said solid form is crystalline Form A having a Raman spectrum comprising at least one peak at a position selected from the group consisting of 213 (±2) cm$^{1}$, 257 (±2) cm$^{-1}$, 1061 (±2) cm$^{-1}$, and 1570 (±2) cm–$^{1}$.

8. The solid form of claim 1, wherein said solid form is crystalline Form A having a melting point above 298° C. using DSC with a heating rate of 10 K/min.

9. A pharmaceutical composition comprising the solid form of claim 1, and a pharmaceutically acceptable excipient.

10. The pharmaceutical composition of claim 9, wherein the pharmaceutical composition is in a powder form.

11. A kit comprising the pharmaceutical composition of claim 9, and water as solvent for constitution of said pharmaceutical composition into an oral aqueous solution.

12. The solid form of claim 1, wherein the solid form is crystalline Form A having an XRPD pattern comprising:
an XRPD peak at 8.3 degrees two-theta (±0.2) angle of diffraction; and
at least two XRPD peaks selected from the group consisting of 11.4 (±0.2) degrees two-theta, 15.1 (±0.2) degrees two-theta, 15.9 (±0.2) degrees two-theta, 17.0 (±0.2) degrees two-theta, 24.0 (±0.2) degrees two-theta, and 25.6 (±0.2) degrees two-theta angle of diffraction.

13. The solid form of claim 1, wherein the solid form is crystalline Form A having an XRPD pattern comprising:
an XRPD peak at 8.3 degrees two-theta (±0.2) angle of diffraction; and
at least three XRPD peaks selected from the group consisting of 11.4 (±0.2) degrees two-theta, 15.1 (±0.2) degrees two-theta, 15.9 (±0.2) degrees two-theta, 17.0 (±0.2) degrees two-theta, 24.0 (±0.2) degrees two-theta, and 25.6 (±0.2) degrees two-theta angle of diffraction.

14. The solid form of claim 1, wherein the solid form is crystalline Form A having an XRPD pattern comprising:
an XRPD peak at 8.3 degrees two-theta (±0.2) angle of diffraction; and
at least four XRPD peaks selected from the group consisting of 11.4 (±0.2) degrees two-theta, 15.1 (±0.2) degrees two-theta, 15.9 (±0.2) degrees two-theta, 17.0 (±0.2) degrees two-theta, 24.0 (±0.2) degrees two-theta, and 25.6 (±0.2) degrees two-theta angle of diffraction.

15. The solid form of claim 1, wherein the solid form is crystalline Form A having an XRPD pattern comprising:
an XRPD peak at 8.3 degrees two-theta (±0.2); and
at least five XRPD peaks selected from the group consisting of 11.4 (±0.2) degrees two-theta, 15.1 (±0.2) degrees two-theta, 15.9 (±0.2) degrees two-theta, 17.0 (±0.2) degrees two-theta, 24.0 (±0.2) degrees two-theta, and 25.6 (±0.2) degrees two-theta angle of diffraction.

16. The solid form of claim 1, wherein said solid form is crystalline Form A having an XRPD pattern comprising XRPD peaks at 12.7 (±0.2) degrees two-theta, 24.0 (±0.2) degrees two-theta, and 25.6 (±0.2) degrees two-theta angle of diffraction.

17. The solid form of claim 1, wherein said solid form is crystalline Form A having an XRPD pattern comprising XRPD peaks at 11.4 (±0.2) degrees two-theta, 12.7 (±0.2) degrees two-theta, 15.9 (±0.2) degrees two-theta, 24.0 (±0.2) degrees two-theta, and 25.6 (±0.2) degrees two-theta angle of diffraction.

18. The solid form of claim 1, wherein said solid form is crystalline Form A having an XRPD pattern comprising XRPD peaks at 11.4 (±0.2) degrees two-theta, 15.1 (±0.2) degrees two-theta, and 25.6 (±0.2) degrees two-theta angle of diffraction.

19. The solid form of claim 1, wherein said solid form is crystalline Form A having an XRPD pattern comprising XRPD peaks at 15.1 (±0.2) degrees two-theta, 17.0 (±0.2) degrees two-theta, 25.6 (±0.2) degrees two-theta angle of diffraction.

20. The solid form of claim 1, wherein said solid form is crystalline Form A having an XRPD pattern comprising XRPD peaks at 15.1 (±0.2) degrees two-theta, 24.0 (±0.2) degrees two-theta, 25.6 (±0.2) degrees two-theta angle of diffraction.

21. The solid form of claim 1, wherein said solid form is crystalline Form A having an XRPD pattern comprising XRPD peaks at 8.3 (±0.2) degrees two-theta and 11.4 (±0.2) degrees two-theta; 8.3 (±0.2) degrees two-theta and 15.1 (±0.2) degrees two-theta, 8.3 (±0.2) degrees two-theta and 15.9 (±0.2) degrees two-theta; or 8.3 (±0.2) degrees two-theta and 17.0 (±0.2) degrees two-theta angle of diffraction.

22. The solid form of claim 14, wherein the x-ray powder diffraction pattern is obtained from a Cu Ka source.

23. The solid form of claim 21, wherein the x-ray powder diffraction pattern is obtained from a Cu Ka source.

24. A pharmaceutical composition comprising the solid form of claim 2, and a pharmaceutically acceptable excipient.

25. A pharmaceutical composition comprising the solid form of claim 12, and a pharmaceutically acceptable excipient.

26. A pharmaceutical composition comprising the solid form of claim 13, and a pharmaceutically acceptable excipient.

27. A pharmaceutical composition comprising the solid form of claim 14, and a pharmaceutically acceptable excipient.

28. A pharmaceutical composition comprising the solid form of claim 15, and a pharmaceutically acceptable excipient.

29. A pharmaceutical composition comprising the solid form of claim 21, and a pharmaceutically acceptable excipient.

30. The solid form of claim 1, wherein said solid form is crystalline Form A, having an IR spectrum comprising at least three peaks at positions selected from the group consisting of 848 (±2) $cm^{-1}$, 885 (±2) $cm^{-1}$, 939 (±2) $cm^{1}$, and 1218 (±2) $cm^{-1}$.

31. The solid form of claim 1, wherein said solid form is crystalline Form A having a Raman spectrum comprising at least three peaks at positions selected from the group consisting of 213 (±2) $cm^{-1}$, 257 (±2) $cm^{-1}$, 1061 (±2) $cm^{-1}$, and 1570 (±2) $cm^{-1}$.

* * * * *